United States Patent
Freeman et al.

(10) Patent No.: US 12,258,409 B2
(45) Date of Patent: Mar. 25, 2025

(54) METHOD OF ASSESSING THE EFFICACY OF A TEST AGENT FOR MODULATING PROGRAMMED DEATH 1 (PD-1) SIGNALING BY USING ANTI-PHOSPHOTYROSINYLATED PD-1 MONOCLONAL ANTIBODIES

(71) Applicants: Dana-Farber Cancer Institute, Inc., Boston, MA (US); Beth Israel Deaconess Medical Center, Boston, MA (US); President and Fellows of Harvard College, Cambridge, MA (US)

(72) Inventors: Gordon J. Freeman, Brookline, MA (US); Vassiliki A. Boussiotis, Brookline, MA (US); Xia Bu, Brookline, MA (US); Vikram R. Juneja, Boston, MA (US); Arlene H. Sharpe, Brookline, MA (US); Nikolaos Patsoukis, Boston, MA (US); Jessica Weaver, Brighton, MA (US); Laura Strauss, Boston, MA (US)

(73) Assignees: Dana-Farber Cancer Institute, Inc., Boston, MA (US); Beth Israel Deaconess Medical Center, Boston, MA (US); President and Fellows of Harvard College, Cambridge, MA (US)

( * ) Notice: Subject to any disclaimer, the term of this patent is extended or adjusted under 35 U.S.C. 154(b) by 65 days.

(21) Appl. No.: 17/934,441

(22) Filed: Sep. 22, 2022

(65) Prior Publication Data
US 2023/0331847 A1   Oct. 19, 2023

Related U.S. Application Data

(62) Division of application No. 16/603,894, filed as application No. PCT/US2018/028581 on Apr. 20, 2018, now Pat. No. 11,492,403.

(60) Provisional application No. 62/487,808, filed on Apr. 20, 2017.

(51) Int. Cl.
| | |
|---|---|
| C07K 16/44 | (2006.01) |
| C07K 16/28 | (2006.01) |
| G01N 33/50 | (2006.01) |
| G01N 33/574 | (2006.01) |

(52) U.S. Cl.
CPC .......... *C07K 16/2818* (2013.01); *C07K 16/44* (2013.01); *G01N 33/5011* (2013.01); *G01N 33/57492* (2013.01); *C07K 2317/33* (2013.01); *C07K 2317/34* (2013.01); *C07K 2317/76* (2013.01); *C07K 2317/92* (2013.01); *G01N 2333/70596* (2013.01); *G01N 2440/14* (2013.01); *G01N 2500/04* (2013.01); *G01N 2500/10* (2013.01); *G01N 2500/20* (2013.01); *G01N 2800/52* (2013.01)

(58) Field of Classification Search
CPC ..... G01N 33/5011; G01N 2333/70596; G01N 2440/14; G01N 2500/04; G01N 2500/10; G01N 2500/20; G01N 2800/52; C07K 2317/33; C07K 2317/34; C07K 2317/76
See application file for complete search history.

(56) References Cited

U.S. PATENT DOCUMENTS

| | | |
|---|---|---|
| 11,492,403 B2 | 11/2022 | Freeman et al. |
| 2015/0210769 A1 | 7/2015 | Freeman et al. |
| 2020/0115452 A1 | 4/2020 | Freeman et al. |

FOREIGN PATENT DOCUMENTS

| | | |
|---|---|---|
| WO | WO-2015/035606 A1 | 3/2015 |
| WO | WO-2016/014688 A2 | 1/2016 |
| WO | WO-2017/055443 A1 | 4/2017 |
| WO | WO-2018/231339 A2 | 12/2018 |

OTHER PUBLICATIONS

Boussiatis VA. (Nov. 3, 2016) New Engl J Med. 375(18):1767-1778. (doi: 10.1056/NEJMra1514296).*
Chemnitz JM, et al. (2004) J Immunol. 173(2):945-954. (https://doi.org/10.4049/jimmunol.173.2.945).*
Colman, "Effects of amino acid sequence changes on antibody-antigen interactions," Research in Immunology, 145(1):33-36 (1994).
International Preliminary Report on Patentability for International Application No. PCT/US2018/028581 dated Oct. 22, 2019.
International Search Report and Written Opinion for International Application No. PCT/US2018/028581 dated Feb. 27, 2019.
Mandell. "Phosphorylation state-specific antibodies: applications in investigative and diagnostic pathology," The American journal of pathology, 163(5):1687-1698 (2003).
Paul, "Fundamental Immunology, 3rd Edition," 292-295 (1993).
Riley et al., "PD-1 signaling in primary T cells," Immunological reviews, 229(1):114-125 (2009).
Rudikoff et al., "Single amino acid substitution altering antigen-binding specificity," PNAS, 79:1979-1983 (1982).

* cited by examiner

*Primary Examiner* — Robert S Landsman
(74) *Attorney, Agent, or Firm* — Foley Hoag LLP

(57) ABSTRACT

The present invention is based, in part, on the discovery of monoclonal and polyclonal antibodies that specifically bind to phosphorylated PD-1, as well as immunoglobulins, polypeptides, nucleic acids thereof, and methods of using such antibodies for diagnostic, prognostic, and therapeutic purposes.

18 Claims, 47 Drawing Sheets
Specification includes a Sequence Listing.

Jurkat-hPD-1 Cells, intracellular staining and analysis by flow cytometry

———— Untreated, mIgG2a (1)   ———— Untreated, 407.6G12 (2)

········· Pervanadate treated, mIgG2a (3)   ········· Pervanadate treated, 407.6G12 (4)

Note: pervanadate treatment inhibits dephosphorylation and thus stabilizes tyrosine phosphorylation

- hIgG treated (1)
- Tetramer treated (2)
- isotype control stain (3)

- hIgG treated
- Tetramer treated

FIG. 8A

MQIPQAPWPVVWAVLQLGWRPGWFLDSPDRPWNPPTFSPALLVVTEGDNATFTCSFSNTS
1                                                         60

ESFVLNWYRMSPSNQTDKLAAFPEDRSQPGQDCRFRVTQLPNGRDFHMSVVRARRNDSGT
                                                          120

YLCGAISLAPKAQIKESLRAELRVTERRAEVPTAHPSPSPRPAGQFQTLVVGVVGGLLGS
                                                          180

LVLLVWVLAVIGSRAARGTIGARRTGQPLKEDPSAVPVFSVDYGELDFQWREKTPEPPVP
            223                                           240

CVPEQTEYATIVFPSGMGTSSPARRGSADGPRSAQPLRPEDGHCSWPL   SEQ ID NO: 136
     248

FIG. 8B

ITSM (human): VPEQTE(pY)ATIVF    SEQ ID NO: 146
ITSM (mouse): ACVHTE(pY)ATIVF    SEQ ID NO: 147

FIG. 8C

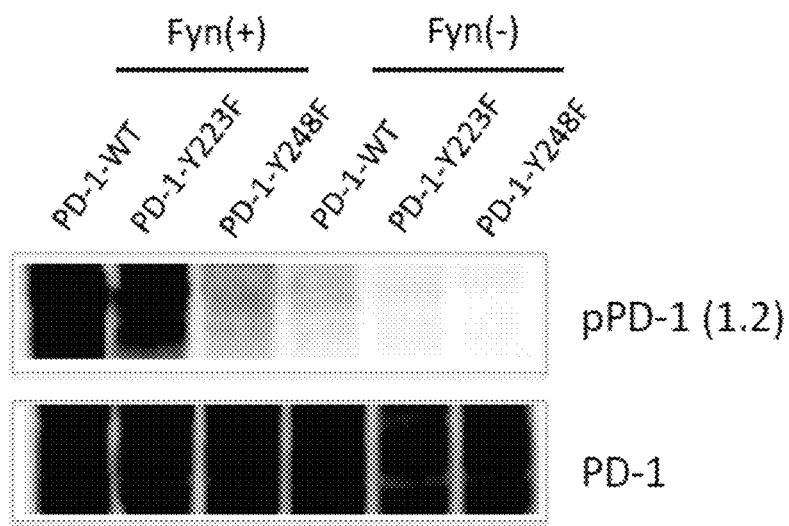

Residues 20-138 of SEQ ID NO: 46 and Nucleotides 58-413 of SEQ ID NO: 45

```
        <-----------------------FR1-IMGT----------------------><----CDR1-IMGT
    Q   V   Q   L   V   E   S   G   G   D   L   V   K   P   G   A   S   L   T   L   T   C   K   A   S   G   F   S   F   S   G
CAGGTGCAGCTGGTGGAGTCCGGGGGAGACCTGGTCAAGCCTGGGGCATCCCTGACACTCACCTGCAAAGCCTCTGGATTCTCCTTCAGTGGC    137                        226
    ---><-----FR2-IMGT-----><-----CDR2-IMGT
    S   Y   H   M   C   W   V   R   Q   A   P   G   K   G   L   E   W   I   A   H   I   Y   V   G   S   G   G   T   Y
AGCTACCACATGTGCTGGGTCCGCCAGGCTCCAGGGAAGGGGCTGGAATGGATCGCACACATCTATGTTGGTAGTGGTGGCACTTAC          227                        316
    ----><------------------FR3-IMGT
    Y   A   S   W   A   K   G   R   F   A   I   S   K   T   S   S   T   V   T   L   Q   M   T   S   L   T   A   A
TACGCGAGCTGGGCAAAGGGCCGATTCGCCATCTCCAAA---ACCTCGTCGACCGTGACTCTGCAAATGACCAGTCTGACAGCCGCG           317                        403
    -----><--------------CDR3-IMGT-------->
    D   T   A   T   Y   F   C   A   R   R   D   T   G   S   A   V   A   L   W   G   Q   G   T   L   V   T   V   S
GACACGGCCACCTATTTCTGTGCGAGAAGGGATACTGGTTCGGCGGTACTGTTATGCCTTGTGGGGCCAGGGCACCCTGGTCACCGTCTC         404                        492
```

2K4;

Residues 23-132 of SEQ ID NO: 28 and Nucleotides 67-396 of SEQ ID NO: 27

```
        <----------------------FR1-IMGT------------------------><----CDR1-IMGT
    D   V   V   M   T   Q   T   P   S   S   A   S   E   P   V   G   G   T   V   T   I   K   C   Q   A   S   Q   S   V   S
GATGTTGTGATGACCCAAACTCCATCTCCGCTGTCTGCATCTGAACCTGTGGGAGGCACAGTCACCATCAAGTGCCAGGCCAGTCAAAGTGTTAGT    147                        236
    ---><-----FR2-IMGT-----><----CDR2-IMGT
    S   R   L   A   W   Y   Q   Q   K   P   G   Q   P   P   K   L   L   I   Y   K   A   S   T   L   A   S   G   V   P   S
AGTAGATTAGCCTGGTATCAGCAAAAACCAGGGCAGCCTCCCAAGCTCCTGATCTACAAGGCATCCACTCTGGCATCTGGGGTCCCATCG          237                        326
    ----><------------------FR3-IMGT
    R   F   K   G   S   G   Y   G   T   X   F   T   L   T   I   S   D   L   E   C   A   D   A   A   T   Y   Y   C   Q   Q
CGGTTCAAAGGCAGTGGATATGGGACAGAGTTCACTCTCACAATCAGCGACCTGGAGTGTGCCGATGCTGCCACTTACTACTGTCAATGT         327                        416
    -----><----------CDR3-IMGT----------->
    T   Y   I   D   S   T   Y   G   N   F   G   G   G   T   E   V   V   K
ACTTATATTGATAGTACTTATGGAAATAATTCGGCGGGGGGGACCGAGGTGGTGGTCAAAG                                    477
```

Residues 20-135 of SEQ ID NO: 82 and Nucleotides 58-404 of SEQ ID NO: 81

```
<-------------------FR1-IMGT---------------------><---CDR1-IMGT--
 Q  S  V  E  E  S  G  G  R  L  V  T  P  G  T  P  L  T  C  T  V  S  G  I  D  L  N  Y
CAGTCGGTGGAGGAGTCCGGGGGTCGCCTGGTCACCCCTGGGACACCCCTGACACTGCACCTCACCTGCACAGTCTCCACACTCGACCTCAATTAC  225
                                                                                     136
-----><---------FR2-IMGT----------><----CDR2-IMGT----><-----
  Y  A  M  G  W  V  R  Q  A  P  G  K  G  L  E  Y  I  G  W  I  K  S  G  S  A  Y  Y  A  R
TATGCAATGGGCTGGGTCCGCCAGGCTCCAGGGAAGGGGCTGGAATACATCGGATGGATTAAAAGTGGTAGCGCATACTACGCGAGG  315
                                                                           226
            FR3-IMGT
  W  V  N  G  R  F  T  I  S  K  T  S  S  T  T  V  D  L  K  M  T  S  P  T  T  E  D  T  A  T
TGGGTGAATGGTCGATTCACCATCTCCAAAACCTCGTCGACCACCGTGGATCTGAAAATGACCAGTCCGACAACCGAGGACACGGCCACC  405
                                                                                     316
----><-------------CDR3-IMGT------------->
  Y  F  C  A  R  D  G  H  N  I  I  E  Y  Y  D  L  W  G  Q  G  T  L  V  T  V  S
TATTTCTGTGCCAGAGATGGCCACAATATAATTGAATATTACGATTTGTGGCCAGGGCACCCTGGTCACCGTCTCC  482
                                                                 406
```

6K2

Residues 23-132 of SEQ ID NO: 64 and Nucleotides 67-396 of SEQ ID NO: 63

```
<-------------------FR1-IMGT--------------------------><---CDR1-IM
 A  I  K  M  T  Q  T  P  S  S  A  E  A  A  V  G  G  T  I  T  I  N  C  Q  A  S  Q  S  I  S
GCCATCAAAATGACCCAGACTCCATCCTCCGCGGAGGCAGCTGTGGGAGGCACAATCACCATCAATTGTCAGGCAGTCAGAGCATTAGT  549
                                                                                   460
GT----><---------FR2-IMGT-----------><---CDR2-IM><----
  S  S  L  A  W  Y  Q  Q  K  P  G  Q  F  P  K  L  L  I  Y  K  A  S  T  L  A  S  G  V  P  S
AGTAGCTTAGCCTGGTATCAGCAGAAACCAGGGCAGCCTCCCAAACTCCTGATCTACAAGGCTTCCACTCTGGCATCTGGGGTCCCGTCG  639
                                                                            550
  FR3-IMGT
  R  F  S  G  S  R  S  G  T  Q  F  T  L  T  I  S  G  V  Q  C  D  D  A  A  T  Y  Y  C  Q  Q
CGGTTCAGTGGCAGTAGATCTGGGACACAGTTCACTCTCACCATCAGCGGCGTGCAGTGTGACGATGCTGCCACTTACTACTGTCAACAG  729
                                                                            640
-------CDR3-IMGT-------->
  G  W  S  G  D  N  V  D  N  I  F  G  G  G  T  E  V  V  V  K
GGTTGGAGTGGTGATAATGTTGATAATATTTTTGGCGGAGGGACCGAGTGGTGGTGGTCAAAG  790
```

Residues 20-139 of SEQ ID NO: 118 and Nucleotides 58-416 of SEQ ID NO: 117

```
<----------------------------FR1-IMGT----------------------------><----CDR1-I
 Q  E  Q  L  V  E  S  G  G  D  L  V  R  P  G  A  S  L  T  L  T  C  T  A  S  G  F  S  F  X
CAGGAGCAGCTGGTGGAGTCCGGGGGAGACCTGGTCAGGCCTGGGGCATCCCTGACACTCACCTGCACAGCCTCTGGATTCTCCTTCANT  226

MGT----><----FR2-IMGT----------------------><----CDR2-IMGT------>
 S  S  Y  H  M  C  W  V  R  Q  A  P  G  K  G  L  E  W  I  A  Y  I  Y  A  G  N  S  G  T
AGCAGCTACCACATGTGCTGGGTCCGCCAGGCTCCAGGGAAGGGGCTGGAGTGGATCGCATACATTTATGCTGGTAATAGCGGTGGCACT  316

<---------------FR3-IMGT-------------------
 Y  Y  A  S  W  A  K  G  R  F  T  I  S  K  A  S  S  T  T  V  T  L  Q  M  T  S  L  T  A  A
TACTACGCGAGTTGGGCGAAAGGCCGATTCACCATCTCCAAAGCCTCGTCGACCACGGTGACTCTGCAAATGACCAGTCTGACAGCCGCG  406

------------------------><------CDR3-IMGT---------------->
 D  T  A  T  Y  F  C  A  R  R  D  T  G  G  T  S  A  Y  A  L  W  G  Q  G  T  L  V  T  V  S
GACACGGCCACCTATTTCTGTGCGAGAAGGGATACTGGTGGCACCAGTGCTTATGCCTTGTGGGGCCAGGGCACCCTGGTCACCGTCTC  496
```

7K1

Residues 26-132 of SEQ ID NO: 100 and Nucleotides 75-396 of SEQ ID NO: 99

```
<----------------------------FR1-IMGT-----------------------------><-----CDR1-IMGT----><
 M  T  Q  T  P  A  S  V  S  E  P  V  G  G  T  V  T  I  K  C  Q  A  S  E  S  I  S  S  R  L
GATGACCCAAACTCCAGCCTCCGTGTCTGAACCTGTGGGAGGCACAGTCACCATCAAGTGCCAGGCCAGTGAGAGCATTAGTAGTAGATT  243

----FR2-IMGT------------------><-----CDR2-IMGT--><-
 A  W  Y  Q  Q  K  P  G  Q  P  P  K  L  L  I  Y  K  A  S  T  L  A  S  G  V  P  S  R  F  K
AGCCTGGTATCAGCAAAACCAGGGCAGCCTCCCAAGCTCCTGATCTACAAGGCATCCACTCTGGCATCTGGGGTCCCATCGCGGTTCAAA  333

-----------FR3-IMGT-----------------------------><
 G  S  G  Y  G  T  E  F  T  L  T  I  S  D  L  E  C  A  D  A  A  T  Y  Y  C  Q  C  T  Y  I
GGCAGTGGATATGGGACAGAGTTCACTCTCACCATCAGCGACCTGGAGTGTGCCGATGCTGCCACTTACTACTGTCAATGTACTTATAT  423

-----CDR3-IMGT----->
 A  S  Y  G  M  N  F  G  G  G  T  E  V  V  V  K
TGCTAGTAGTTATGGAAATAATTTCGGCGGAGGGACCGAGGTGGTGGTCAAA  475
```

METHOD OF ASSESSING THE EFFICACY OF A TEST AGENT FOR MODULATING PROGRAMMED DEATH 1 (PD-1) SIGNALING BY USING ANTI-PHOSPHOTYROSINYLATED PD-1 MONOCLONAL ANTIBODIES

CROSS-REFERENCE TO RELATED APPLICATIONS

This application is a divisional of U.S. application Ser. No. 16/603,894, filed on 9 Oct. 2019 and now U.S. Pat. No. 11,492,403, which is the U.S. national phase of International Patent Application No. PCT/US2018/028581, filed on 20 Apr. 2018 and which claims the benefit of priority to U.S. Provisional Application Ser. No. 62/487,808, filed on 20 Apr. 2017; the entire contents of each of said applications are incorporated herein in their entirety by this reference.

STATEMENT OF RIGHTS

This invention was made with government support under grant numbers P50 CA206963, P01 AI054456, P01 AI056299, P01 AI080192, P50 CA101942, U19 AI082630, and RO1 CA183605 awarded by the National Institutes of Health and grant number W81XWH-15-1-0687 awarded by the Department of Defense. The government has certain rights in the invention.

SEQUENCE LISTING

The present specification makes reference to a Sequence Listing (submitted electronically as a .xml file named "DFS-180.02_Sequence_Listing.xml" on Sep. 22, 2022). The .xml file was generated on Sep. 20, 2022 and is 197 kilobytes in size. The entire contents of the Sequence Listing are herein incorporated by reference.

BACKGROUND OF THE INVENTION

Antibodies blocking the programmed death (PD)-1 pathway have shown remarkable clinical efficacy across multiple cancers in recent years (Mahoney et al. (2015) *Nat. Rev. Drug Discov.* 14:561-584). However, not all patients receiving these therapies have durable, objective responses. Unlike conventional chemotherapies, it can take weeks or months for beneficial clinical effects to become apparent in patients who respond (Postow et al. (2015) *J. Clin. Oncol.* 33:1974-1982). Although PD-L1 expression in the tumor microenvironment has been shown to correlate with a higher response to PD-1 pathway blockade (Taube et al. (2014) *Clin. Cancer Res.* 20:5064-5074), patients whose tumors do not express PD-L1 can respond to PD-1 pathway blockade. This highlights the need for biomarkers that can be used to assess the efficacy of PD-1 immunotherapies before or early during treatment (Herbst et al. (2014) *Nature* 515:563-567).

A major challenge in achieving this goal is the complexity of the PD-1 pathway. Effector T cells express PD-1 upon activation, as do B cells, NK cells, and some myeloid cells (Francisco et al. (2010) *Immunol. Rev.* 236:219-242). In addition to its expression on many cell subsets, PD-1 may have various effects within different cell types upon interaction with its ligands. In activated T cells, PD-1 ligation diminishes TCR signaling, resulting in attenuated effector T cell responses (e.g., proliferation, cytokine production, cytotoxicity). In contrast, PD-1 ligation on regulatory T cells (Tregs), which can express PD-1 under resting conditions, may impact Treg homeostasis and function, although the role of PD-1 on Tregs is not well understood. Further, PD-1 expression has been described on myeloid and NK cells, yet its functionality on these cell types is unclear. The ligands for PD-1 (e.g., PD-L1 and PD-L2) are expressed on multiple cell types. PD-L1 is broadly expressed on hematopoietic and non-hematopoietic cells, whereas PD-L2 is generally restricted to expression on antigen-presenting cells and airway epithelia (Baumeister et al. (2016) *Annu. Rev. Immunol.* 34:539-573). Both ligands can be expressed by tumor cells, either alone or together (Baumeister et al. (2016), supra). Due to the complex function of PD-1 on various cell subsets and the broad expression of its ligands, it is difficult to accurately determine where and when PD-1 pathway blockade alters T cell function. Accordingly, there is a need in the art to identify new anti-PD-1 antibodies having a specificity and sensitivity for phosphorylated PD-1 to better assess the efficacy of PD-1 pathway blockade in a cell-specific manner.

SUMMARY OF THE INVENTION

The present invention is based, at least in part, on the discovery of new anti-PD-1 monoclonal and polyclonal antibodies (e.g., mAbs 6G12, 2H2/2K4, 6H2/6K2, and 7H5/7K1, and polyclonal antibodies 1.2 and 2.2) that can bind to and detect phosphorylated PD-1 at, e.g., the phosphorylation sites (e.g., Y248) in the immunoreceptor tyrosine-based switch motif (ITSM) of the intracellular tail of both human and mouse PD-1. Moreover, such antibodies provide an unexpectedly superior ability to detect phosphorylated PD-1 polypeptides in detection assays. Such antibodies may be useful in diagnosing and/or prognosing of diseases and disorders (e.g., cancers) in response to PD-1 blockade or combination therapy. For example, the antibodies can be used to quantitate the number of T cells in which the PD-1 pathway is activated and thus serve as an easily assayable marker for PD-1 pathway activation in an assay of peripheral blood cells from a patient with cancer, a chronic infection like HIV/AIDS or hepatitis, and the like. This knowledge can be used to identify the tumor antigens recognized by these T cells, as well as to use such antibodies for diagnostic, prognostic, and therapeutic purposes.

In one aspect, a monoclonal antibody, or antigen-binding fragment thereof, wherein the monoclonal antibody specifically binds to a phosphorylation site of PD-1, is provided.

In another aspect, a polyclonal antibody, or antigen-binding fragment thereof, wherein the polyclonal antibody specifically binds to a phosphorylation site of PD-1, is provided.

Numerous embodiments are further provided that can be applied to any aspect of the present invention and/or combined with any other embodiment described herein. For example, in one embodiment, the monoclonal and/or polyclonal antibody or antigen-binding fragment thereof specifically binds to PD-1 of at least two species. In another embodiment, the monoclonal and/or polyclonal antibody or antigen-binding fragment thereof specifically binds to human and mouse PD-1. In still another embodiment, the monoclonal and/or polyclonal antibody or antigen-binding fragment thereof specifically binds to a PD-1 phosphorylated at the phosphorylation site. For example, such PD-1 may be phosphorylated at the phosphorylation site upon PD-L1 ligation. In one embodiment, the phosphorylation site of PD-1 is in the intracellular tail of PD-1. In another embodiment, the phosphorylation site of PD-1 is in the immunotyrosine switch motif (ITSM) of PD-1. In still another embodiment, the phosphorylation site of PD-1 is tyrosine residue 223 and/or tyrosine residue 248 of human PD-1, or an orthologous phosphorylation site in an ortholog of human PD-1. In yet another embodiment, the phosphorylation site of PD-1 is tyrosine residue 248 of human PD-1, or an orthologous phosphorylation site in an ortholog of human PD-1.

In another embodiment, the PD-1 described herein comprises an amino acid sequence: i) with at least 70% identity to at least one heavy chain sequence and/or light chain sequence selected from the sequences listed in Table 1, such as at least one sequence selected from SEQ ID NOs: 28 and 30; ii) with at least 80% identity to at least one heavy chain sequence and/or light chain sequence selected from the sequences listed in Table 1; iii) with at least 90% identity to at least one heavy chain sequence and/or light chain sequence selected from the sequences listed in Table 1; iv) with at least 95% identity to at least one heavy chain sequence and/or light chain sequence selected from the sequences listed in Table 1; v) with at least 99% identity to at least one heavy chain sequence and/or light chain sequence selected from the sequences listed in Table 1; or vi) selected from at least one heavy chain sequence and/or light chain sequence selected from the sequences listed in Table 1. In still another embodiment, the PD-1 described herein is encoded by a polynucleotide comprising a nucleic acid sequence i) with at least 70% identity to at least one heavy chain sequence and/or light chain sequence selected from the sequences listed in Table 1, such as at least one sequence selected from SEQ ID NO: 27 and 29; ii) with at least 80% identity to at least one heavy chain sequence and/or light chain sequence selected from the sequences listed in Table 1; iii) with at least 90% identity to at least one heavy chain sequence and/or light chain sequence selected from the sequences listed in Table 1; iv) with at least 95% identity to at least one heavy chain sequence and/or light chain sequence selected from the sequences listed in Table 1; v) with at least 99% identity to at least one heavy chain sequence and/or light chain sequence selected from the sequences listed in Table 1; vi) selected from at least one heavy chain sequence and/or light chain sequence selected from the sequences listed in Table 1; or vii) hybridizing, under stringent conditions, with the complement of a nucleic acid sequence selected from at least one heavy chain sequence and/or light chain sequence selected from the sequences listed in Table 1, such as SEQ ID NOs: 27 and 29. In yet another embodiment, the monoclonal and/or the polyclonal antibody described herein comprises: a) a heavy chain sequence with at least about 95% identity to a heavy chain sequence selected from the group consisting of the sequences listed in Table 1; and/or b) a light chain sequence with at least about 95% identity to a light chain sequence selected from the group consisting of the sequences listed in Table 1. In another embodiment, the monoclonal antibody and/or the polyclonal antibody described herein comprises: a) a heavy chain CDR sequence with at least about 95% identity to a heavy chain CDR sequence selected from the group consisting of the sequences listed in Table 1; and/or b) a light chain CDR sequence with at least about 95% identity to a light chain CDR sequence selected from the group consisting of the sequences listed in Table 1. In still another embodiment, the monoclonal antibody and/or the polyclonal antibody described herein comprises: a) a heavy chain sequence selected from the group consisting of the sequences listed in Table 1; and/or b) a light chain sequence selected from the sequences listed in Table 1. In yet another embodiment, the monoclonal antibody and/or the polyclonal antibody described herein comprises: a) a heavy chain CDR sequence selected from the group consisting of the sequences listed in Table 1; and/or b) a light chain CDR sequence selected from the group consisting the sequences listed in Table 1. In one embodiment, the monoclonal antibody or antigen-binding fragment thereof described herein is chimeric, humanized, composite, murine, or human. In another embodiment, the polyclonal antibody or antigen-binding fragment thereof described herein comprises a monoclonal antibody which is chimeric, humanized, composite, murine, or human. In another embodiment, the monoclonal antibody, or antigen-binding fragment thereof, described herein is detectably labeled, comprises an effector domain, comprises an Fc domain, and/or is selected from the group consisting of Fv, Fav, F (ab') 2), Fab', dsFv, scFv, sc (Fv) 2, and diabodies fragments. In still another embodiment, the polyclonal antibody or antigen-binding fragment thereof described herein comprises a monoclonal antibody, or antigen-binding fragment thereof, which is detectably labeled, comprises an effector domain, comprises an Fc domain, and/or is selected from the group consisting of Fv, Fav, F (ab') 2), Fab', dsFv, scFv, sc (Fv) 2, and diabodies fragments. In still one embodiment, the monoclonal antibody or antigen-binding fragment thereof described herein inhibits the binding of commercial antibody to PD-1. In yet another embodiment, the polyclonal antibody or antigen-binding fragment thereof described herein comprises a monoclonal antibody, or antigen-binding fragment thereof, which inhibits the binding of commercial antibody to PD-1.

In another aspect, an immunoglobulin heavy and/or light chain selected from the group consisting of the sequences listed in Table 1, is provided.

In still another aspect, an isolated nucleic acid molecule that hybridizes, under stringent conditions, with the complement of a nucleic acid encoding a polypeptide selected from the group consisting of the sequences listed in Table 1, or a sequence with at least about 95% homology to a nucleic acid encoding a polypeptide selected from the group consisting of the sequences listed in Table 1, is provided.

In yet another aspect, a vector comprising the isolated nucleic acid described herein, is provided.

In another aspect, a host cell which comprises the isolated nucleic acid described herein, comprises the vector described herein, expresses the antibody or antigen-binding fragment thereof described herein is provided.

In still another aspect, a device or kit comprising at least one monoclonal and/or polyclonal antibody, or antigen-binding fragment thereof, described herein, said device or kit optionally comprising a label to detect the at least one monoclonal and/or polyclonal antibody or antigen-binding fragment thereof, or a complex comprising the monoclonal and/or polyclonal antibody or antigen-binding fragment thereof, is provided.

In yet another aspect, a method of producing at least one monoclonal and/or polyclonal antibody, or antigen-binding fragment thereof, described herein, is provided, the method comprising the steps of: (i) culturing a transformed host cell which has been transformed by a nucleic acid comprising a sequence encoding a monoclonal and/or polyclonal antibody described herein under conditions suitable to allow expression of said antibody, or antigen-binding fragment thereof; and (ii) recovering the expressed antibody, or antigen-binding fragment thereof.

In another aspect, a method of detecting the presence or level of a phosphorylated PD-1 polypeptide, comprising obtaining a sample and detecting said polypeptide in the sample by use of at least one monoclonal and/or polyclonal antibody, or antigen-binding fragment thereof, described herein, is provided. For example, the at least one monoclonal and/or polyclonal antibody, or antigen-binding fragment thereof, may form a complex with a phosphorylated PD-1 polypeptide and the complex may be detected in the form of an enzyme linked immunosorbent assay (ELISA), radioimmune assay (RIA), immunochemically, Western blot, or using an intracellular flow assay.

In still another aspect, a method for monitoring the progression of a disorder associated with aberrant PD-1 in a subject is provided, the method comprising: a) detecting in a subject sample at a first point in time the level of phosphorylated PD-1 using at least one monoclonal and/or polyclonal antibody, or antigen-binding fragment thereof, described herein; b) repeating step a) at a subsequent point in time; and c) comparing the level of phosphorylated PD-1 detected in steps a) and b) to monitor the progression of the disorder in the subject. For example, between the first point in time and the subsequent point in time, the subject may have undergone treatment to ameliorate the disorder.

In yet another aspect, a method for predicting the clinical outcome of a subject afflicted with a disorder associated with aberrant PD-1 is provided, the method comprising: a) determining the level of phosphorylated PD-1 in a subject sample using at least one monoclonal and/or polyclonal antibody, or antigen-binding fragment thereof, described herein; b) determining the level of phosphorylated PD-1 in a sample from a control subject having a good clinical outcome using at least one monoclonal and/or polyclonal antibody, or antigen-binding fragment thereof, described herein; and c) comparing the level of phosphorylated PD-1 in the subject sample and in the sample from the control subject, wherein a significantly higher level of phosphorylated PD-1 in the subject sample as compared to the level in the sample from the control subject is an indication that the subject has a poor clinical outcome.

In another aspect, a method of assessing the efficacy of a therapy for a disorder associated with aberrant PD-1 in a subject is provided, the method comprising: a) determining the level of phosphorylated PD-1 using at least one monoclonal and/or polyclonal antibody, or antigen-binding fragment thereof, described herein, in a first sample obtained from the subject prior to providing at least a portion of the therapy to the subject, and b) determining the level of phosphorylated PD-1 in a second sample obtained from the subject following provision of the portion of the therapy, wherein a significantly lower level of phosphorylated PD-1 in the second sample, relative to the first sample, is an indication that the therapy is efficacious for inhibiting the disorder in the subject.

In still another aspect, a method of assessing the efficacy of a test compound for inhibiting a disorder associated with aberrant PD-1 in a subject is provided, the method comprising: a) determining the level of phosphorylated PD-1 using at least one monoclonal and/or polyclonal antibody, or antigen-binding fragment thereof, described herein, in a first sample obtained from the subject and exposed to the test compound; and b) determining the level of phosphorylated PD-1 in a second sample obtained from the subject, wherein the second sample is not exposed to the test compound, and a significantly lower level of phosphorylated PD-1, relative to the second sample, is an indication that the test compound is efficacious for inhibiting the disorder in the subject.

As described above, numerous embodiments are further provided that can be applied to any aspect of the present invention and/or combined with any other embodiment described herein. For example, in one embodiment, the first and second samples are portions of a single sample obtained from the subject or portions of pooled samples obtained from the subject. In another embodiment, the disorder is a cancer. In still another embodiment, the sample comprises cells, serum, peritumoral tissue, and/or intratumoral tissue obtained from the subject. In yet another embodiment, said significantly higher level of phosphorylated PD-1 comprises an at least twenty percent increase between the level of phosphorylated PD-1 in the subject sample relative to the normal level of phosphorylated PD-1 in the sample from the control subject. In another embodiment, said significantly lower level of phosphorylated PD-1 comprises an at least twenty percent decrease of the level of phosphorylated PD-1. In still another embodiment, the subject described herein is a human. In yet another embodiment, the subject has a PD-1 protein capable of phosphorylation on Y248 of human PD-1, or an orthologous phosphorylation site in an ortholog of human PD-1. In another embodiment, the subject has a PD-1 protein without a mutation, substitution, and/or insertion abrogating phosphorylation on Y248 of human PD-1, or an orthologous phosphorylation site in an ortholog of human PD-1.

In another aspect, a method of assessing the efficacy of a test agent for modulating PD-1 signaling, the method comprising a) contacting PD-1 with a test agent and b) determining the ability of the test agent to modulate the level of phosphorylated PD-1 using at least one monoclonal or polyclonal antibody, or antigen-binding fragment thereof, wherein a modulated level of phosphorylated PD-1 resulting from contacting with the test agent identifies the test agent as a modulator of PD-1 signaling, is provided. In one embodiment, contacting PD-1 with the test agent occurs within a cell or in a cell-free environment.

BRIEF DESCRIPTION OF FIGURES

FIG. 3A shows the results of CD8$^+$ TILs from WT mice (left) or PD-1$^{-/-}$ mice (right) evaluated for expression of cell surface PD-1 and levels of phosphorylated PD-1. CD8$^+$ TILs from WT mice were also stained with isotype control antibody (center). Geometric mean fluorescence intensity (MFI) of phospho-PD-1 in both PD-1$^+$ and PD-1$^-$ CD8$^+$ T cells from dLN and tumor of WT mice on days 7, 10, and 20 is compared in FIG. 3B. CD8$^+$ T cells from PD-1$^{-/-}$ mice were also evaluated on day 10. The dotted line shows levels of isotype control stain on CD8$^+$ PD-1$^+$ T cells from tumor of WT mice. CD4$^+$ FoxP3$^{GFP+}$ Tregs from the dLN (left) or tumor (center) were evaluated for intracellular levels of phospho-PD-1 and compared to isotype control from WT mice on day 20 (FIG. 3C). Staining of Tregs in the tumor vs dLN was compared (right). MFI of phospho-PD-1 in PD-1$^+$ and PD-1$^-$ Tregs from dLN (left) or tumor (right) of WT mice on day 20 is compared in FIG. 3D. All data shown are representative of at least 2 independent experiments (n≥4 mice per group).

FIG. 4A shows the results of CD8$^+$ TILs from WT mice evaluated for surface expression of PD-1 and TIM-3 on day 20. Phospho-PD-1 levels in TIM-3$^-$ versus TIM-3$^+$ PD-1$^+$ TILs were compared in FIG. 4B. Quantification of phospho-PD-1 levels in PD-1$^+$ TIM-3$^-$ versus PD-1$^+$ TIM-3$^+$ CD8+ and Treg TILs is shown in FIG. 4C and FIG. 4D. Blocking antibodies against PD-1 (200 µg, 1A12) were administered on days 7, 10, and 13, and T cells from tumors and dLN were assayed for phospho-PD-1 expression on day 14 (FIG. 4E and FIG. 4F). Geometric mean fluorescence intensity of phospho-PD-1 from (FIG. 4E) all CD8$^+$ T cells (left), and on PD-1$^+$ TIM-3$^+$ CD8$^+$ T cells (right), and (FIG. 4F) all CD4$^+$FoxP3$^{GFP+}$ T cells (left) and on PD-1$^+$ TIM-3$^+$ CD4$^+$FoxP3$^{GFP+}$ T cells (right) is shown. All data shown representative of at least 2 independent experiments (n≥4 mice per group).

FIG. 5A depicts the separation of purified CD3+CD4+vs. CD3+CD8+ T cells from human PBMCs. The expression of PD-1, PD-L1, phospho-PD-1, and CD80 were detected with corresponding antibodies in CD3+ T cells purified from human PBMC, which were not stimulated (FIG. 5B) or stimulated (FIG. 5C) with CD3/CD28, or either not stimulated (FIG. 5D) or stimulated (FIG. 5E) but treated with PD-L1, after culturing for 24 hours. FIG. 5F compares the expression of phospho-PD-1 in CD3+ cells purified from human PBMC, not stimulated with CD3/CD28, with or without PD-L1 treatment. FIG. 5G compares the expression of phospho-PD-1 in CD3+ cells purified from human PBMC, stimulated with CD3/CD28, with or without PD-L1 treatment.

FIG. 7A depicts that another tyrosine in ITIM, Y223, does not affect SHP-2 interaction. FIG. 7B depicts the immunoprecipitation (IP) of SHP-2 by PD-1 wild-type and a Y223F mutant, but not PD-1 Y248F or Y223/Y248F mutants. Cos cells were transfected with PD-1, Fyn and SHP2. The whole cell lysates ("WL") and the IP product ("PD-1 IP") were used for electrophoresis and Western Blot using antibodies against SHP-2, PD-1, and Fyn.

FIGS. 8A-8G show the production and the characterization of anti-phospho-PD-1 antibodies. FIG. 8A depicts the PD-1 sequence used for generating antibodies specific for phosphorylated Y248 of PD-1. FIG. 8B shows the sequence of the conserved ITSM region in mouse and human PD-1 used in the immunogen peptide. FIGS. 8C-8F show two polyclonal anti-phospho-PD-1 antibodies (1.2 and 2.2) specifically recognize PD-1-Y248. COS cells were transfected with cDNA PD-1-WT or mutagenized in Y223 (ITIM) or Y248 (ITSM) and immunoblot in whole cell lysates was performed with PD-1pY248-specific antibodies (1.2 in FIG. 8C and 2.2 in FIG. 8E) or PD-1 antibody. Jurkat T cells transfected with PD-1-WT were left untreated or incubated with pervanadate (PV) for various time intervals followed by incubation with PE-conjugated PD-1pY248 antibody 1.2 (FIG. 8D) or 2.2 (FIG. 8F). In FIGS. 8D and 8F, the peaks refer to cells treated with PV for 30 mins plus Ab 1.2 (#1), cells treated with PV for 15 mins plus Ab 1.2 (#2), cells treated with PV for 5 mins plus Ab 1.2 (#3), cells treated with PV for 1 mins plus Ab 1.2 (#4), cells treated with PV plus IgG (#5), and cells untreated plus Ab 1.2 (#6). FIG. 8G depicts the Western Blot result for immunoprecipitation of SHP-2 by PD-1 but not PD-1 Y248F mutant. Loss of Y248 phosphorylation abrogates SHP-2 recruitment to PD-1.

FIG. 9A depicts the PD-1 expression in different CD4+ T cell subsets. FIG. 9B depicts the PD-1 expression in different CD8+ T cell subsets. FIG. 9C depicts that phospho-PD-1 (Y248) is expressed in CD4+ central memory and effector memory T cells.

FIG. 9D depicts that phospho-PD-1 (Y248) is expressed in CD8+ central memory and effector memory T cells.

FIG. 14A shows the results of primary human T cells cultured with PHA for 12 hours and subsequently stimulated with tosylactivated magnetic beads coated with the indicated Ab and Ig proteins. Immunoprecipitation (IP) was done with anti-PD-1 Ab followed by immunoblot with SHP-2. FIG. 14B shows the results of COS cells transfected with cDNA for PD-1 and each of the indicated kinases in active (+) or inactive (−) isoform. IP was done with anti-PD-1 Ab followed by immunoblot as indicated. FIG. 14C shows the results of whole cell lysates analyzed for the expression of the indicated proteins, as assessed by immunoblot.

FIG. 15A depicts a bar graph comparing the percentage (the upper panel) and number (the lower panel) of CD11b+CD45+, CD11bLy6C$^{hi}$, and CD11bLy6G+ cells as mean+/−SD in WT MDSC-like cells. FIG. 15B depicts a bar graph comparing the percentage and number of CD11b+ CD45+, CD11bLy6C$^{hi}$, and CD11bLy6G+ cells as mean+/−SD in RORC$^{−/−}$ MDSC-like cells. FIG. 15C depicts the flow cytometry gating strategy for BM MDSCs-like cells. FIGS. 15D and 15E depict the results of flow cytometry analysis in WT (FIG. 15D) and RORC$^{−/−}$ (FIG. 15E) MDSCs-like cells for phospho-PD-1 expression after 4 days T cell co-culture. FIG. 15F depicts the levels of CD11b+Ly6Chi+ MDSCs like cells after 4 days of co-incubation with different T cells. Data of one representative experiment are shown.

FIGS. 17A-17C show sequences of rabbit mAbs 2H2/2K4 (FIG. 17A), 6H2/6K2 (FIG. 17B), and 7H5/7K1 (FIG. 17C).

Figure 1A:
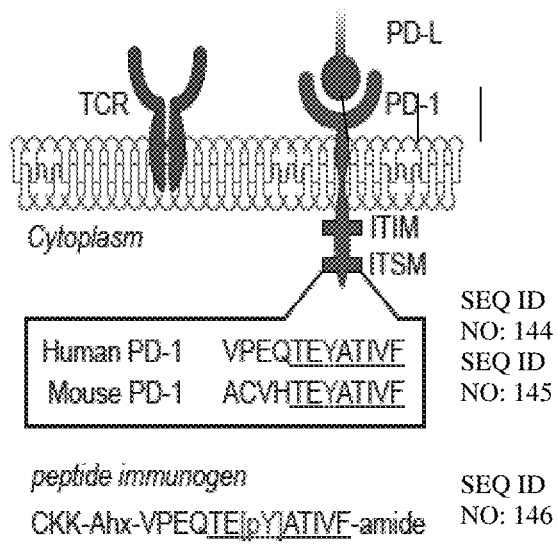
FIG. 1A-1D show the development of an anti-phospho-PD-1 antibody. Peptide immunogen contains conserved amino acid sequence encompassing the ITSM sequence of mouse and human PD-1 cytoplasmic tail (FIG. 1A). Hybridomas were screened by Western blot (FIG. 1B). Lysates were made from the indicated cell lines known to express either mouse PD-1 (mPD-1) or human PD-1 (hPD-1), and the indicated cell lines were treated with pervanadate (Per) to stabilize phosphorylation of PD-1. 4T1 and 300.19 were used as negative controls for mouse lysates, and Jurkat E6 and Caki-2 were used as negative controls for human lysates, respectively. EL4 and 300-mPD-1 were used as positive controls for mPD-1 and Jurkat hPD-1 were used as positive controls for hPD-1. Pervanadate-treated EL4 and Jurkat-hPD-1 were used to assess PD-1 phosphorylation. All samples were blotted with antibodies to GAPDH (loading control), hPD-1 (6G1), mPD-1 (1A12) and phospho-PD-1 (6G12). Phospho-PD-1 expression in Jurkat-hPD-1 cells either untreated (middle curve) or treated with pervanadate (right curve) is shown in FIG. 1C. mIgG2a was used as a control in FIG. 1D. All data shown are representative of 3 independent experiments.

Note that for every figure containing a histogram, the bars from left to right for each discreet measurement correspond to the figure boxes from top to bottom in the figure legend as indicated.

DETAILED DESCRIPTION OF THE INVENTION

The present invention is based, in part, on the discovery of new anti-PD-1 monoclonal and polyclonal antibodies (e.g., mAbs 6G12, 2H2/2K4, 6H2/6K2, and 7H5/7K1, and polyclonal antibodies 1.2 and 2.2) that can bind to and detect phosphorylated PD-1 at, e.g., the phosphorylation sites (e.g., Y248) in immunoreceptor tyrosine-based switch motif (ITSM) of the intracellular tail of both human and mouse PD-1. Moreover, such antibodies provide an unexpectedly superior ability to detect phosphorylated PD-1 polypeptides in detection assays (e.g., Western blot, immunohistochemistry, flow cytometry, fixed tissue immunohistochemistry such as formalin-fixed, paraffin-embedded immunohistochemistry, and the like). Such antibodies may be useful in diagnosing and/or prognosing of diseases and disorders (e.g., cancers) in response to PD-1 blockade or combination therapy. For example, the antibodies can be used to quantitate the number of T cells in which the PD-1 pathway is activated and thus serve as an easily assayable marker for PD-1 pathway activation in an assay of peripheral blood cells from a patient with cancer, a chronic infection like HIV/AIDS or hepatitis, and the like. The antibodies can be used to isolate tumor infiltrating lymphocytes with an activated PD-1 pathway by intracellular flow cytometry and cell sorting. The tumor infiltrating lymphocytes with an activated PD-1 pathway are the T cells that have specifically responded to tumor antigens and been inactivated by PDL1-expressing tumor cells. These PD-1 activated cells can be analyzed for their T cell receptor utilization by next-generation RNA sequencing or similar methods. This knowledge can be used to identify the tumor antigens recognized by these T cells.

I. Definitions

The articles "a" and "an" are used herein to refer to one or more than one (i.e. to at least one) of the grammatical object of the article. By way of example, "an element" means one element or more than one element.

The term "altered amount" of a marker refers to increased or decreased copy number of a marker and/or increased or decreased nucleic acid level of a particular marker gene or genes in a sample, as compared to that of the marker in a control sample. The term "altered amount" of a marker also includes an increased or decreased protein level of a marker in a sample, as compared to the protein level of the marker in a normal, control sample.

The term "altered activity" of a marker refers to an activity of a marker which is increased or decreased in a disease state, e.g., in a biological sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as V$_H$) and a heavy chain constant region. The heavy chain constant region is comprised of three domains, CH1, CH2 and CH3. Each light chain is comprised of a light chain variable region (abbreviated herein as V$_L$) and a light chain constant region. The light chain constant region is comprised of one domain, CL. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a phosphorylated PD-1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention bind specifically or substantially specifically to a phosphorylated PD-1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluids that are normally not (e g amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

"Complement [to]" or "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. In another embodiment, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daeron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, "Framework" or "FR" residues are those variable-domain residues other than the HVR residues as herein defined.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like) Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, NJ, 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune cell" refers to cells that play a role in the immune response Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune disorder" includes immune diseases, conditions, and predispositions to, including, but not limited to, cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy) and malaria.

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibiting" and grammatical equivalents thereof refer decrease, limiting, and/or blocking a particular action, function, or interaction. In one embodiment, the term refers to reducing the level of a given output or parameter to a quantity (e.g., background staining, PD-1 and/or phosphorylated PD-1 signaling, PD-1 immunoinhibitory function, and the like) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. The given output or parameter can be determined using methods well known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term an "isolated antibody" is intended to refer to an antibody which is substantially free of other antibodies having different antigenic specificities (e.g., an isolated antibody that specifically binds to phosphorylated human PD-1 (preferably on a phosphorylation site of PD-1) and is substantially free of antibodies that do not bind to the phosphorylated PD-1). An isolated antibody that specifically binds to a phosphorylation site of human PD-1 may, however, have cross-reactivity to other PD-1 proteins, respectively, from different species. For example, in some embodiments, the antibody maintains specific binding affinity for at least two species, such as human and mouse, or other mammal or non-mammal species. However, in some embodiments, the antibody maintains higher or indeed specific affinity and selectivity for human PD-1. In addition, an isolated antibody is typically substantially free of other cellular material and/or chemicals. In one embodiment of the present invention, a combination of "isolated" monoclonal antibodies having different specificities to human PD-1 are combined in a well-defined composition.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a target polypeptide (e g, immunoglobulin) or fragment thereof, in which the protein is separated from cellular components of the cells from which it is isolated or recombinantly produced. In one embodiment, the language "substantially free of cellular material" includes preparations of target protein or fragment thereof, having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the present invention. The kit may be promoted, distributed, or sold as a unit for performing the methods of the present invention.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the present invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the present invention. A marker protein comprises the entire or a partial sequence of any of the sequences set forth in the Sequence Listing. In some embodiments, the overall PD-1 (i.e., phosphorylated and non-phosphorylated) is used as a marker. In other embodiments, the phosphorylated PD-1 is used as a marker. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a disease or disorder related to aberrant marker levels. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to phosphorylated PD-1 (preferably on a phosphorylation site on PD-1, e.g., Y248, such as mAbs 6G12, 2H2/2K4, 6H2/6K2, and 7H5/7K1, and polyclonal antibodies 1.2 and 2.2), is intended to refer to a nucleic acid molecule in which the nucleotide sequences encoding the antibody or antibody portion are free of other nucleotide sequences encoding antibodies or antibody portions that bind antigens other than PD-1, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term "phosphorylation" refers to a biochemical reaction in which a phosphate group is added to Ser, Thr or Tyr residues of a protein and is catalyzed by protein kinase enzymes. Phosphorylation normally modifies the functions of target proteins, often causing activation of the target protein. As part of the cell's homeostatic mechanisms, phosphorylation is only a transient process that is reversed by other enzyme called phosphatases. Therefore, protein phosphorylation levels change over time and can be evaluated in a number of well-known manners, including, for example, by immunological approaches. For example, the amount, timing, status, etc. of human PD-1 phosphorylation at, for example, Y248, or a corresponding phosphorylatable amino acid in an ortholog of human PD-1, can be determined using antibodies described herein, such as monoclonal and polyclonal antibodies (e.g., biclonal antibodies containing a mixture of two separate monoclonal antibodies, or more than two separate monoclonal antibodies). Such antibodies can be used in any one of well-known immunoassay forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with NMR, MALDI-TOF, LC-MS/MS, are known to those of ordinary skill in the art.

Such reagents can also be used to monitor protein levels in a cell or tissue, e.g., white blood cells or lymphocytes, as part of a clinical testing procedure, e.g., in order to monitor an optimal dosage of an inhibitory agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Such reagents can also be used with any number of biological samples. Biological samples can be collected from a variety of sources from a patient including a body fluid sample, cell sample, or a tissue sample comprising nucleic acids and/or proteins. In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Samples can contain live cells/tissue, fresh frozen cells, fresh tissue, biopsies, fixed cells/tissue, cells/tissue embedded in a medium, such as paraffin, histological slides, or any combination thereof.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention "response" is generally related to for example, determining the effects on progression, efficacy, or outcome of a clinical intervention. In some embodiments, responses relate directly to a change in tumor mass and/or volume after initiation of clinical intervention (e.g., administration of an anti-phosphorylated PD-1 monoclonal antibody, such as mAbs 6G12, 2H2/2K4, 6H2/6K2, and 7H5/7K1, and polyclonal antibodies 1.2 and 2.2). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human phosphorylated PD-1 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a disease or disorder related to aberrant marker levels. The term "subject" is interchangeable with "patient". The term "non-human animal" includes all vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, wordlength=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electro-

II. Monoclonal Antibodies, Immunoglobulins, and Polypeptides

The present invention relates, in part, to isolated monoclonal antibodies or fragments thereof that are directed against at least on a phosphorylation site (e.g., Y248) of PD-1 (such as mAbs 6G12, 2H2/2K4, 6H2/6K2, and 7H5/7K1, and polyclonal antibodies 1.2 and 2.2). Such molecules are characterized in that they exhibit a superior ability to recognize phosphorylated PD-1 protein in diagnostic assays, such as immunohistochemical (IHC), Western blot, intercellular flow, ELISA, and the like, compared to known anti-PD-1 antibodies that bind non-phosphorylated PD-1.

For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 2 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

In some embodiments, a condition such as cancer is responsive to PD-1 blockade alone. In other embodiments, a condition such as cancer is responsive to PD-1 blockade alone, but is significantly or synergistically more responsive when treated with PD-1 blockade and another therapy in combination. Many conditions responsive to PD-1 blockade alone are known and include, without limitation, melanoma (e.g., advanced or metastatic melanoma), lung cancer (e.g., non-small cell lung cancer and small cell lung cancer), breast cancer (e.g., HER-2 negative breast cancer, estrogen-receptor+/HER-2-breast cancer, and triple negative breast cancer), pancreatic cancer (e.g., pancreatic adenocarcinoma), and Hodgkin lymphoma, as well as bladder, gastric, head and neck, renal, prostate, gynecologic, and hematologic cancers.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) *J. Exp. Med.* 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two 13 sheets, each consisting of anti-parallel 13 strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of 13 strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The variable domain of the light and heavy chains of the 6G12 mAb have been sequenced and the complementarity determining regions (CDRs) domains thereof are provided herein and in Table 1. For example, the 6G12 light chain variable (vK) polypeptide sequence, including the signal sequence (shown in bold, highlighted text), is

```
                                           (SEQ ID NO: 1)
MVSSAQFLVYMLLWLSGVDGDIVMTQSQKFMSTSVGDRVSVTCKASQNVG

TNVAWYQQKPGQSPKALIYSASYRYSGVPDRFTGSGSGTDFTLTISNVHS

EDLAEYFCQQYNFYPLTFGAGTKLELK,
``` wherein CDR definitions and protein sequence numbering are listed according to Kabat nomenclature and CDR amino acid sequences are underlined in order of CDR1, CDR2, and CDR3, respectively. Thus, the light chain variable CDR 1

```
      (CDR-L1) is
                                  (SEQ ID NO: 6)
      KASQNVGTNVA,

CDR-L2 is
                                  (SEQ ID NO: 9)
      SASYRYS,
      and CDR-L3 is
                                  (SEQ ID NO: 12)
      QQYNFYPLT.
```

The 6G12 signal (shown in bold, highlighted text) and light chain variable (vK) polypeptide sequence is encoded by the following nucleic acid sequence:

```
                                           (SEQ ID NO: 2)
   1  atggtgtcct cagctcagtt ccttgtatac atgttgctgt ggttgtctgg tgttgatgga 61  gacattgtga tgacccagtc tcaaaaattc atgtccacat cagtaggaga cagggtcagc 121  gtcacctgca aggccagtca gaatgtgggt actaatgtag cctggtatca acagaaacca 181  gggcaatctc ctaaagcact gatttactcg gcatcctacc ggtacagtgg agtccctgat 241  cgcttcacag gcagtggatc toggacagat ttcactctca ccatcagcaa tgtgcactct 301  gaagacttgg cagagtattt ctgtcagcaa tataacttct atcctctcac gttcggtgct 361  gggaccaagc tggagctgaa a
```

Similarly, the 6G12 heavy chain variable (vH) polypeptide sequence, including the signal sequence (shown in bold, highlighted text), is

```
                                           (SEQ ID NO: 14)
MLLGLKWVFFVVFYQGVRHEVQLVESGGGLVQPKGSLKLSCAASGFTFNT

YAMNWVRQAPGKGLEWVARIRSKSDNYATYYADSVKDRFTISRDDSQSML

YLQMNNLKTEDTAMYYCMRGITTVNVWGAGTTVTVSS,
``` wherein, CDR definitions and protein sequence numbering are listed according to Kabat nomenclature and CDR amino acid sequences are underlined in order of CDR1, CDR2, and CDR3, respectively. Thus, CDR-H1 is

TYAMN, (SEQ ID NO: 19)

CDR-H2 is

RIRSKSDNYATYYADSVKD, (SEQ ID NO: 22)
and

CDR-H3 is

GITTVNV. (SEQ ID NO: 25)

The 6G12 signal (shown in bold, highlighted text) and heavy chain variable (vH) polypeptide sequence is encoded by the following nucleic acid sequence:

```
                                          (SEQ ID NO: 15
  1  atgctgttgg ggctgaagtg ggtttctttt gttgttttt atcaaggtgt gcgtcatgag 61  gtgcagcttg ttgagtctgg tggaggattg gtgcagccta aagggtcatt gaaactctca 121  tgtgcagcct ctggattcac cttcaatacc tacgccatga actgggtccg ccaggctcca 181  ggaaagggt tggaatgggt tgctcgcata agaagtaaaa gtgataatta tcaacatat 241  tatgccgatt cagtgaaaga caggttcacc atctccagag atgattcaca aagcatgctc 301  tatctgcaaa tgaacaactt gaaaactgag gacacagcca tgtattactg tatgagggg 361  attactacgg tcaatgtctg gggcgcaggg accacggtca ccgtctcctc a.
```

Similarly, sequences of the rabbit mAbs 2H2/2K4, 6H2/6K2, and 7H5/7K1 are also provided herein, such as in Table 1, FIG. 17, and the like.

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the present invention (e.g., including the sequences of Table 1, or portions thereof). The antibodies further can comprise the CDR2s of variable regions of the present invention (e.g., including the sequences of Table 1, or portions thereof). The antibodies further can comprise the CDR1s of variable regions of the present invention (e.g., including the sequences of Table 1, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 1, or portions thereof) disclosed herein. However, the ordinarily skilled artisan will appreciate that some deviation from the exact CDR sequences may be possible while still retaining the ability of the antibody to bind phosphorylated PD-1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 1, or portions thereof).

The structural features of known, non-human or human antibodies (e.g., a mouse anti-human phosphorylated PD-1 antibody) can be used to create structurally related human anti-human phosphorylated PD-1 antibodies that retain at least one functional property of the antibodies of the present invention, such as binding at least one of the phosphorylation sites (e.g., Y248) of PD-1 (such as mAbs 6G12, 2H2/2K4, 6H2/6K2, and 7H5/7K1, and polyclonal antibodies 1.2 and 2.2). Another functional property includes inhibiting binding of the original known, non-human or human antibodies in a competition ELISA assay.

In some embodiments, monoclonal antibodies capable of binding at least one of the phosphorylation sites (e.g., Y248) of human PD-1 (such as mAbs 6G12, 2H2/2K4, 6H2/6K2, and 7H5/7K1, and polyclonal antibodies 1.2 and 2.2) are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1.

Similarly, monoclonal antibodies capable of binding at least one of the phosphorylation sites (e.g., Y248) of human PD-1 (such as mAbs 6G12, 2H2/2K4, 6H2/6K2, and 7H5/7K1, and polyclonal antibodies 1.2 and 2.2), comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

Monoclonal antibodies capable of binding at least one of the phosphorylation sites (e.g., Y248) of human PD-1 (such as mAbs 6G12, 2H2/2K4, 6H2/6K2, and 7H5/7K1, and polyclonal antibodies 1.2 and 2.2), comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 1 and a light chain, wherein the variable domain comprises at least a CDR having a sequence selected from the group consisting of the light chain variable domain CDRs presented in Table 1.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding at least one of the phosphorylation sites (e.g., Y248) of human PD-1 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth in Table 1 and/or the light chain variable domain of the monoclonal antibodies of the present invention can comprise or consist of the vκ amino acid sequence set forth in Table 1.

The monoclonal antibodies of the present invention can be produced and modified by any technique well known in the art. Similarly, such monoclonal antibodies can be chimeric, preferably chimeric mouse/human antibodies. In some embodiments, the monoclonal antibodies are humanized antibodies such that the variable domain comprises human acceptor frameworks regions, and optionally human constant domain where present, and non-human donor CDRs, such as mouse CDRs as defined above.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as non-phosphorylated PD-1, PD-L2, PD-L1, CTLA-4, and the like, can be detected in a bispecific or multispecific manner in order to efficiently characterize the expression of such molecules.

Other fragments of the monoclonal antibodies of the present invention are also contemplated. For example, individual immunoglobulin heavy and/or light chains are provided, wherein the variable domains thereof comprise at least a CDR presented in Table 1. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 1. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein (e.g., presented in Table 1).

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided in Table 1.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

TABLE 1

Identification and sequencing of the leader and variable regions of anti-phosphorylated PD-1 monoclonal antibody, 407.6G12

6G12 Light Chain Variable (vK) DNA and Amino Acid Sequences*

```
LOCUS   6G12_VK   381 bp DNA linear
FEATURES          Location/Qualifiers
J segment         352..381
                  /label=JK V segment         325..351
                  /label=CDR3

V region          229..324
                  /label=FWR3

V segment         208..228
                  /label=CDR2

V region          163..207
                  /label=FWR2

V segment         130..162
                  /label+32a CDR1

V region          61..129
                  /label=FWR1 sig_peptide       1..60
                  /label=LS

CDS               1..381
                  /label=6G12_VK
```

TABLE 1-continued

Identification and sequencing of the leader and variable regions of anti-phosphorylated PD-1 monoclonal antibody, 407.6G12

| #Measure | Position | Value | Cutoff | signal peptide? |
|---|---|---|---|---|
| max. C | 21 | 0.845 | | |
| max. Y | 21 | 0.844 | | |
| max. S | 16 | 0.894 | | |
| mean S | 1-20 | 0.843 | | |
| D | 1-20 | 0.843 | 0.450 | YES |

Name=Sequence SP='YES' Cleavage site between pos. 20 and 21: VDG-DI
D=0.843 D-cutoff=0.450 Networks=SignalP-noTM 6G12 VK
/translation="MVSSAQFLVYMLLWLSGVDGDIVMTQSQKFMSTSVGDRVS
VTCKASQNVGTNVAWYQQKPGQSPKALIYSASYRYSGVPDRFTGSGSGTDFTLT
ISNVHSEDLAEYFCQQYNFYPLTFGAGTKLELK" (SEQ ID NO: 1)

BASE COUNT 95 a 91 c 94 g 101 t

ORIGIN
  1     atggtgtcct cagctcagtt ccttgtatac atgttgctgt ggttgtctgg tgttgatgga
 61     gacattgtga tgacccagtc tcaaaaattc atgtccacat cagtaggaga cagggtcagc
121     gtcacctgca aggccagtca gaatgtgggt actaatgtag cctggtatca acagaaacca
181     gggcaatctc ctaaagcact gatttactcg gcatcctacc ggtacagtgg agtccctgat
241     cgcttcacag gcagtggatc tgggacagat ttcactctca ccatcagcaa tgtgcactct
301     gaagacttgg cagagtattt ctgtcagcaa tataacttct atcctctcac gttcggtgct
361     gggaccaagc tggagctgaa a (SEQ ID NO: 2)

Signal Peptide (base pairs 1-60) (SEQ ID NO: 3):
  1     atggtgtcct cagctcagtt ccttgtatac atgttgctgt ggttgtctgg tgttgatgga     60
        (SEQ ID NO: 3)

Framework 1 (base pairs 61-129) (SEQ ID NO: 4):
 61          gacattgtga tgacccagtc tcaaaaattc atgtccacat cagtaggaga cagggtcagc
121          gtcacctgc                                                              129 (SEQ ID NO: 4)

CDR-L1 (base pairs 130-162):
130          aag gcc agt cag aat gtg ggt act aat gta gcc                            177 (SEQ ID NO: 5)
              K   A   S   Q   N   V   G   T   N   V   A  (SEQ ID NO: 6)

Framework 2 (base pairs 163-207) (SEQ ID NO: 7):
163          tggtatca acagaaacca gggcaatctc ctaaagcact gatttac                     207 (SEQ ID NO: 7)

CDR-L2 (base pairs 208-228):
208          tcg gca tcc tac cgg tac agt                                           228 (SEQ ID NO: 8)
              S   A   S   Y   R   Y   S  (SEQ ID NO: 9)

Framework 3 (base pairs 229-324) (SEQ ID NO: 10):
229          gg agtccctgat cgcttcacag gcagtggatc tgggacagat ttcactctca
             ccatcagcaa tgtgcactct gaagacttgg cagagtattt ctgt                      324 (SEQ ID NO: 10)

CDR-L3 (base pairs 325-351):
325          cag caa tat aac ttc tat cct ctc acg                                   351 (SEQ ID NO: 11)
              Q   Q   Y   N   F   Y   P   L   T  (SEQ ID NO: 12)

J Segment (base pairs 352-381) (SEQ ID NO: 13):
352          ttcggtgct gggaccaagc tggagctgaa a                                     381 (SEQ ID NO: 13)

6G12 Heavy Chain Variable (vH) DNA and Amino Acid Sequences*

LOCUS 407.4.6G12.20.13.2_VH 411 bp DNA linear
Anti-h/m PhosphoTyrosine PD-1
FEATURES         Location/Qualifiers
J segment        379..411
                 /label=JH

TABLE 1-continued

Identification and sequencing of the leader and variable regions of anti-phosphorylated PD-1 monoclonal antibody, 407.6G12

```
V segment       358..378
                /label=CDR3

V region        262..357
                /label=FWR3

V segment       205..261
                /label=CDR2

V region        163..204
                /label=FWR2

V segment       148..162
                /label=CDR1

V region        58..147
                /label=FWR1 sig peptide     1..57
                /label=LS

CDS             1..411
                /label=6G12_VH
```

| #Measure | Position | Value | Cutoff | signal peptide |
|---|---|---|---|---|
| max. C | 20 | 0.399 | | |
| max. Y | 20 | 0.532 | | |
| max. S | 9 | 0.823 | | |
| mean S | 1-19 | 0.701 | | |
| D | 1-19 | 0.624 | 0.450 | YES |

Name=Sequence SP='YES' Cleavage site between pos. 19 and 20: VRH-EV
D=0.624 D-cutoff=0.450 Networks=SignalP-noTM 6G12 VH
/translation="MLLGLKWVFFVVFYQGVRHEVQLVESGGGLVQPKGSLKLS
CAASGFTF<u>NTYAMN</u>WVRQAPGKGLEWVA<u>RIRSKSDNYATYYADSVKD</u>RFTISRD
DSQSMLYLQMNNLKTEDTAMYYCMR<u>GITTVNV</u>WGAGTTVTVSS" (SEQ ID NO: 14)

BASE COUNT    105 a    83 c    111 g    112 t

```
ORIGIN
    1           atgctgttgg ggctgaagtg ggttttcttt gttgtttttt atcaaggtgt gcgtcatgag
   61           gtgcagcttg ttgagtctgg tgaggattg gtgcagccta aagggtcatt gaaactctca
  121           tgtgcagcct ctggattcac cttcaatacc tacgccatga actgggtccg ccaggctcca
  181           ggaaagggtt tggaatgggt tgctcgcata agaagtaaaa gtgataatta tgcaacatat
  241           tatgccgatt cagtgaaaga caggttcacc atctccagag atgattcaca aagcatgctc
  301           tatctgcaaa tgaacaactt gaaaactgag gacacagcca tgtattactg tatgaggggg
  361           attactacgg tcaatgtctg gggcgcaggg accacggtca ccgtctcctc a
                (SEQ ID NO: 15)
```

Signal Peptide (base pairs 1-57) (SEQ ID NO: 16):
```
    1           atgctgttgg ggctgaagtg ggttttcttt gttgtttttt atcaaggtgt gcgtcat        57
                (SEQ ID NO: 16)
```

Framework 1 (base pairs 58-147) (SEQ ID NO: 17):
```
   58           gag gtgcagcttg ttgagtctgg tgaggattg gtgcagccta aagggtcatt
                gaaactctca tgtgcagcct ctggattcac cttcaat                             147 (SEQ ID NO: 17)
```

CDR-H1 (base pairs 148-162):
```
  148           acc tacgccatga ac                                                   162 (SEQ ID NO: 18)
                 T   Y  A  M   N  (SEQ ID NO: 19)
```

TABLE 1-continued

Identification and sequencing of the leader and variable regions of anti-phosphorylated PD-1 monoclonal antibody, 407.6G12

Framework 2 (base pairs 163-204) (SEQ ID NO: 20):
163　　　　tgggtccg ccaggctcca ggaaagggtt tggaatgggt tgct　　　　204 (SEQ ID NO: 20)

CDR-H2 (base pairs 205-261):
205　　　　cgcata agaagtaaaa gtgataatta tgcaacatat tatgccgatt cagtgaaaga c
261　　　　(SEQ ID NO: 21)
　　　　　　R  I  R  S  K  S  D  N  Y  A  T  Y  Y  A  D  S  V  K  D
　　　　　　(SEQ ID NO: 22)

Framework 3 (base pairs 262-357) (SEQ ID NO: 23):
262　　　　aggttcacc atctccagag atgattcaca aagcatgctc tatctgcaaa tgaacaactt
　　　　　　gaaaactgag gacacagcca tgtattactg tatgagg　　　　357 (SEQ ID NO: 23)

CDR-H3 (base pairs 358-378):
358　　　　ggg attactacgg tcaatgtc　　　　378 (SEQ ID NO: 24)
　　　　　　G  I  T  T  V  N  V  (SEQ ID NO: 25)

J Segment (base pairs 379-411) (SEQ ID NO: 26):
379　　　　tg gggcgcaggg accacggtca ccgtctcctc a　　　　411 (SEQ ID NO: 26)

2H2/2K4 Light Chain Variable(vK) DNA and Amino Acid Sequences* cDNA sequence:
ATGGACACGAGGGCCCCCACTCAGCTGCTGGGGCTCCTGCTGCTCTGGCTCCCAGGTGCCAGATGTGATG
TTGTGATGACCCAGACTCCATCTTCCGCGTCTGAACCTGTGGGAGGCACAGTCACCATCAAGTGCCAGGC
CAGTCAGAGCGTTAGTAGTAGATTAGCCTGGTATCAGCAGAAACCAGGGCAGCCTCCCAAGCTCCTGATC
TACAAGGCATCCACTCTGGCATCTGGGGTCCCATCGCGGTTCAAAGGCAGTGGATATGGGACAGAGTTCA
CTCTCACCATCAGCGACCTGGAGTGTGCCGATGCTGCCACTTACTACTGTCAATGTACTTATATTGATAG
TACTTATGGAAATAATTTCGGCGGAGGGACCGAGGTGGTGGTCAAA (SEQ ID NO: 27)

Polypeptide sequence:
MDTRAPTQLLGLLLLWLPGARCDVVMTQTPSSASEPVGGTVTIKCQAS<u>QSVSSR</u>LAWYQQ
KPGQPPKLLIY<u>KAS</u>TLASGVPSRFKGSGYGTEFTLTISDLECADAATYYC<u>QCTYIDSTYG</u>
<u>NN</u>FGGGTEVVK (SEQ ID NO: 28)

Annotated sequence:
Leader sequences:
ATGGACACGAGGGCCCCCACTCAGCTGCTGGGGCTCCTGCTGCTCTGGCTCCCAGGTGCCAGATGT (SEQ ID NO: 29)
M  D  T  R  A  P  T  Q  L  L  G  L  L  L  L  W  L  P  G  A  R  C  (SEQ ID NO: 30)

Framework 1 sequences:
GATGTTGTGATGACCCAGACTCCATCTTCCGCGTCTGAACCTGTGGGAGGCACAGTCACCATCAAGTGCC
D  V  V  M  T  Q  T  P  S  S  A  S  E  P  V  G  G  T  V  T  I  K  C  Q

AGGCCAGT (SEQ ID NO: 31)
 A  S (SEQ ID NO: 32)

CDR-L1 sequences:
CAGAGCGTTAGTAGTAGA (SEQ ID NO: 33)
Q  S  V  S  S  R (SEQ ID NO: 34)

Framework 2 sequences:
TTAGCCTGGTATCAGCAGAAACCAGGGCAGCCTCCCAAGCTCCTGATCTAC (SEQ ID NO: 35)
L  A  W  Y  Q  Q  K  P  G  Q  P  P  K  L  L  I  Y (SEQ ID NO: 36)

CDR-H2 sequences:
AAGGCATCC (SEQ ID NO: 37)
K  A  S (SEQ ID NO: 38)

Framework 3 sequences:
ACTCTGGCATCTGGGGTCCCATCGCGGTTCAAAGGCAGTGGATATGGGACAGAGTTCACTCTCACCATCA
T  L  A  S  G  V  P  S  R  F  K  G  S  G  Y  G  T  E  F  T  L  T  I  S GCGACCTGGAGTGTGCCGATGCTGCCACTTACTACTGT (SEQ ID NO: 39)
 D  L  E  C  A  D  A  A  T  Y  Y  C  (SEQ ID NO: 40)

CDR-L3 sequences:
CAATGTACTTATATTGATAGTACTTATGGAAATAAT (SEQ ID NO: 41)
Q  C  T  Y  I  D  S  T  Y  G  N  N  (SEQ ID NO: 42)

J Segment sequences:
TTCGGCGGAGGGACCGAGGTGGTGGTCAAA (SEQ ID NO: 43)
F  G  G  G  T  E  V  V  V  K  (SEQ ID NO: 44)

TABLE 1-continued

Identification and sequencing of the leader and variable regions of anti-phosphorylated PD-1 monoclonal antibody, 407.6G12

2H2/2K4 Heavy Chain Variable (vH) DNA and Amino Acid Sequences* cDNA sequence:
ATGGAGACTGGGCTGCGCTGGCTTCTCCTGGTCGCTGTGCTCAAAGGTGTCCAGTGTCAGTCGTTGGAGG
AGTCCGGGGGAGACCTGGTCAAGCCTGGGGCATCCCTGACACTCACCTGCAAAGCCTCTGGATTCTCCTT
CAGTGGCAGCTACCACATGTGCTGGGTCCGCCAGGCTCCAGGGAAGGGGCTGGAGTGGATCGCACACATC
TATGTTGGTAGTAGTGGTGGCACTTACTACGCGAGCTGGGCGAAAGGCCGATTCGCCATCTCCAAAACCT
CGTCGACCACGGTGACTCTGCAAATGACCAGTCTGACAGCCGCGGACACGGCCACCTATTTCTGTGCGAG
AAGGGATACTGGTGGGACCAGTGCTTATGCCTTGTGGGGCCAGGGCACCCTGGTCACCGTCTCGAGC (SEQ ID NO: 45)

Polypeptide sequence:
METGLRWLLLVAVLKGVQCQSLEESGGDLVKPGASLTLTCKASGFSFSGSYHMCWVRQAP
GKGLEWIAHIYVGSSGGTYYASWAKGRFAISKTSSTTVTLQMSLTAADTATYFCARRDT
GGTSAYALWGQGTLVTVSS (SEQ ID NO: 46)

Annotated sequences:
Leader sequences:
ATGGAGACTGGGCTGCGCTGGCTTCTCCTGGTCGCTGTGCTCAAAGGTGTCCAGTGT (SEQ ID NO: 47)
M  E  T  G  L  R  W  L  L  L  V  A  V  L  K  G  V  Q  C (SEQ ID NO: 48)

Framework 1 sequence:
CAGTCGTTGGAGGAGTCCGGGGGAGACCTGGTCAAGCCTGGGGCATCCCTGACACTCACCTGCAAAGCCT
Q  S  L  E  E  S  G  G  D  L  V  K  P  G  A  S  L  T  L  T  C  K  A  S (SEQ ID NO: 50)

CT (SEQ ID NO: 49)

CDR-H1 sequences:
GGATTCTCTTCAGTGGCAGCTACCAC (SEQ ID NO: 51)
G  F  S  F  S  G  S  Y  H (SEQ ID NO: 52)

Framework 2 sequences:
ATGTGCTGGGTCCGCCAGGCTCCAGGGAAGGGGCTGGAGTGGATCGCACAC (SEQ ID NO: 53)
M  C  W  V  R  Q  A  P  G  K  G  L  E  W  I  A  H (SEQ ID NO: 54)

CDR-H2 sequences:
ATCTATGTTGGTAGTAGTGGTGGCACT (SEQ ID NO: 55)
I  Y  V  G  S  S  G  G  T (SEQ ID NO: 56)

Framework 3 sequences:
TACTACGCGAGCTGGGCGAAAGGCCGATTCGCCATCTCCAAAACCTCGTCGACCACGGTGACTCTGCAAA
Y  Y  A  S  W  A  K  G  R  F  A  I  S  K  T  S  S  T  T  V  T  L  Q  M TGACCAGTCTGACAGCCGCGGACACGGCCACCTATTTCTGT (SEQ ID NO: 57)
 T  S  L  T  A  A  D  T  A  T  Y  F  C (SEQ ID NO: 58)

CDR-H3 sequences:
GCGAGAAGGGATACTGGTGGGACCAGTGCTTATGCCTTG (SEQ ID NO: 59)
A  R  R  D  T  G  G  T  S  A  Y  A  L (SEQ ID NO: 60)

J Segment sequences:
TGGGGCCAGGGCACCCTGGTCACCGTCTCGAGC (SEQ ID NO: 61)
W  G  Q  G  T  L  V  T  V  S  S (SEQ ID NO: 62)

6H2/6K2 Light Chain Variable (rK) DNA and Amino Acid Sequences* cDNA sequence:
ATGGACACGAGGGCCCCCACTCAGCTGCTGGGGCTCCTGCTGCTCTGGCTCCCAGGTGCCACATTTGCCA
TCAAAATGACCCAGACTCCATCCTCCGCGGAGGCAGCTGTGGGAGGCACAATCACCATCAATTGTCAGGC
CAGTCAGAGCATTAGTAGTAGCTTAGCCTGGTATCAGCAGAAACCAGGGCAGCCTCCCAAACTCCTGATC
TACAAGGCTTCCACTCTGGCATCTGGGGTCCCGTCGCGGTTCAGTGGCAGTAGATCTGGGACACAGTTCA
CTCTCACCATCAGCGGCGTGCAGTGTGACGATGCTGCCACTTACTACTGTCAACAGGGTTGGAGTGGTGA
TAATGTTGATAATATTTTTGGCGGAGGGACCGAGGTGGTGGTCAAA (SEQ ID NO: 63)

Polypeptide sequence:
MDTRAPTQLLGLLLLWLPGATFAIKMTQTPSSAEAAVGGTITINCQASQSISSSLAWYQQ
KPGQPPKLLIYKASTLASGVPSRFSGSRSGTQFTLTISGVQCDDAATYYCQQGWSGDNVD
NIFGGGTEVVVK (SEQ ID NO: 64)

Annotated sequences:
Leader sequences:
ATGGACACGAGGGCCCCCACTCAGCTGCTGGGGCTCCTGCTGCTCTGGCTCCCAGGTGCCACATTT (SEQ ID NO: 65)
M  D  T  R  A  P  T  Q  L  L  G  L  L  L  L  W  L  P  G  A  T  F (SEQ ID NO: 66)

Framework 1 sequences:
GCCATCAAAATGACCCAGACTCCATCCTCCGCGGAGGCAGCTGTGGGAGGCACAATCACCATCAATTGTC
A  I  K  M  T  Q  T  P  S  S  A  E  A  A  V  G  G  T  I  T  I  N  C  Q TABLE 1-continued Identification and sequencing of the leader and variable regions of anti-phosphorylated PD-1 monoclonal antibody, 407.6G12

AGGCCAGT (SEQ ID NO: 67)
  A  S (SEQ ID NO: 68)

CDR-L1 sequences:
CAGAGCATTAGTAGTAGC (SEQ ID NO: 69)
Q  S  I  S  S  S (SEQ ID NO: 70)

Framework 2 sequences:
TTAGCCTGGTATCAGCAGAAACCAGGGCAGCCTCCCAAACTCCTGATCTAC (SEQ ID NO: 71)
L  A  W  Y  Q  Q  K  P  G  Q  P  P  K  L  L  I  Y (SEQ ID NO: 72)

CDR-L2 sequences:
AAGGCTTCC (SEQ ID NO: 73)
K  A  S (SEQ ID NO: 74)

Framework 3 sequences:
ACTCTGGCATCTGGGGTCCCGTCGCGGTTCAGTGGCAGTAGATCTGGGACACAGTTCACTCTCACCATCA
T  L  A  S  G  V  P  S  R  F  S  G  S  R  S  G  T  Q  F  T  L  T  I  S GCGGCGTGCAGTGTGACGATGCTGCCACTTACTACTGT (SEQ ID NO: 75)
  G  V  Q  C  D  D  A  A  T  Y  Y  C (SEQ ID NO: 76)

CDR-L3 sequences:
CAACAGGGTTGGAGTGGTGATAATGTTGATAATATT (SEQ ID NO: 77)
Q  Q  G  W  S  G  D  N  V  D  N  I (SEQ ID NO: 78)

J Segment sequences:
TTTGGCGGAGGGACCGAGGTGGTGGTCAAA (SEQ ID NO: 79)
F  G  G  G  T  E  V  V  V  K (SEQ ID NO: 80)

6H2/6K2 Heavy Chain Variable (vH) DNA and Amino Acid Sequences* cDNA sequence:
ATGGAGACTGGGCTGCGCTGGCTTCTCCTGGTCGCTGTGCTCAAAGGTGTCCAGTGTCAGTCGGTGGAGG
AGTCCGGGGGTCGCCTGGTCACGCCTGGGACACCCCTGACACTCACCTGCACAGTCTCTGGAATCGACCT
CAATTACTATGCAATGGGCTGGGTCCGCCAGGCTCCAGGGAAGGGGCTGGAATACATCGGATGGATTAAA
AGTAGTGGTAGCGCATACTACGCGAGGTGGGTGAATGGTCGATTCACCATCTCCAAAACCTCGTCGACCA
CGGTGGATCTGAAAATGACCAGTCCGACAACCGAGGACACGGCCACCTATTTCTGTGCCAGAGATGGCCA
CAATATAATTGAATATTATGATTTGTGGGGCCAGGGCACCCTGGTCACCGTCTCGAGC (SEQ ID NO: 81)

Polypeptide sequence:
METGLRWLLLVAVLKGVQCQSVEESGGRLVTPGTPLTLTCTVSGIDLNYYAMGWVRQAPG
KGLEYIGWIKSSGSAYYARWVNGRFTISKTSSTTVDLKMTSPTTEDTATYFCARDGHNII
EYYDLWGQGTLVTVSS (SEQ ID NO: 82)

Annotated sequences:
Leader sequences:
ATGGAGACTGGGCTGCGCTGGCTTCTCCTGGTCGCTGTGCTCAAAGGTGTC (SEQ ID NO: 83)
M  E  T  G  L  R  W  L  L  L  V  A  V  L  K  G  V (SEQ ID NO: 84)

Framework 1 sequences:
CAGTGTCAGTCGGTGGAGGAGTCCGGGGGTCGCCTGGTCACGCCTGGGACACCCCTGACACTCACCT
Q  C  Q  S  V  E  E  S  G  G  R  L  V  T  P  G  T  P  L  T  L  T  C

GCACAGTCTCT (SEQ ID NO: 85)
  T  V  S (SEQ ID NO: 86)

CDR-H1 sequences:
GGAATCGACCTCAATTACTATGCA (SEQ ID NO: 87)
G  I  D  L  N  Y  Y  A (SEQ ID NO: 88)

Framework 2 sequences:
ATGGGCTGGGTCCGCCAGGCTCCAGGGAAGGGGCTGGAATACATCGGATGG (SEQ ID NO: 89)
M  G  W  V  R  Q  A  P  G  K  G  L  E  Y  I  G  W (SEQ ID NO: 90)

CDR-H2 sequences:
ATTAAAAGTAGTGGTAGCGCA (SEQ ID NO: 91)
I  K  S  S  G  S  A (SEQ ID NO: 92)

Framework 3 sequences:
TACTACGCGAGGTGGGTGAATGGTCGATTCACCATCTCCAAAACCTCGTCGACCACGGTGGATCTGAAAA
Y  Y  A  R  W  V  N  G  R  F  T  I  S  K  T  S  S  T  T  V  D  L  K  M TGACCAGTCCGACAACCGAGGACACGGCCACCTATTTCTGT (SEQ ID NO: 93)
  T  S  P  T  T  E  D  T  A  T  Y  F  C (SEQ ID NO: 94)

TABLE 1-continued

Identification and sequencing of the leader and variable regions of anti-phosphorylated PD-1 monoclonal antibody, 407.6G12

CDR-H3 sequences:
GCCAGAGATGGCCACAATATAATTGAATATTATGATTTG (SEQ ID NO: 95)
A R D G H N I I E Y Y D L (SEQ ID NO: 96)

J Segment sequences:
TGGGGCCAGGGCACCCTGGTCACCGTCTCGAGC (SEQ ID NO: 97)
W G Q G T L V T V S S (SEQ ID NO: 98)

7H5/7K1 Light Chain Variable (vK) DNA and Amino Acid Sequences* cDNA sequence:
ATGGACACGAGGGCCCCCACTCAGCTGCTGGGGCTCCTGCTGCTCTGGCTCCCAGGTGCCAAATGTGATG
TTGTGATGACCCAAACTCCAGCCTCCGTGTCTGAACCTGTGGGAGGCACAGTCACCATCAAGTGCCAGGC
CAGTGAGAGCATTAGTAGTAGATTAGCCTGGTATCAGCANAAACCAGGGCAGCCTCCCAAGCTCCTGATC
TACAAGGCATCCACTCTGGCATCTGGGGTCCCATCGCGGTTCAAAGGCAGTGGATATGGGACAGAGTTCA
CTCTCACCATCAGCGACCTGGAGTGTGCCGATGCTGCCACTTACTACTGTCAATGTACTTATATTGCTAG
TAGTTATGGAAATAATTTCGGCGGAGGGACCGAGGTGGTGGTCAAA (SEQ ID NO: 99)

Polypeptide sequence:
MDTRAPTQLLGLLLLWLPGAKCDVVMTQTPASVSEPVGGTVTIKCQAS<u>ESISSRLAWYQX
KPGQPPKLLIYKAS</u>TLASGVPSRFKGSGYGTEFTLTISDLECADAATY<u>YCQCTYIASSYG
NNF</u>GGGTEVVVK (SEQ ID NO: 100)

Annotated sequences:
Leader sequences:
ATGGACACGAGGGCCCCCACTCAGCTGCTGGGGCTCCTGCTGCTCTGGCTCCCAGGTGCCAAATGTGATG
M  D  T  R  A  P  T  Q  L  L  G  L  L  L  L  W  L  P  G  A  K  C  D  V

TTGTG (SEQ ID NO: 101)
  V (SEQ ID NO: 102)

Framework 1 sequences:
ATGACCCAAACTCCAGCCTCCGTGTCTGAACCTGTGGGAGGCACAGTCACCATCAAGTGCCAGGCCAGT (SEQ ID NO: 103)
M T Q T P A S V S E P V G G T V T I K C Q A S (SEQ ID NO: 104)

CDR-L1 sequences:
GAGAGCATTAGTAGTAGA (SEQ ID NO: 105)
E S I S S R (SEQ ID NO: 106)

Framework 2 sequences:
TTAGCCTGGTATCAGCANAAACCAGGGCAGCCTCCCAAGCTCCTGATCTAC (SEQ ID NO: 107)
L A W Y Q X K P G Q P P K L L I Y (SEQ ID NO: 108)

CDR-L2 sequences:
AAGGCATCC (SEQ ID NO: 109)
K A S (SEQ ID NO: 110)

Framework 3 sequences:
ACTCTGGCATCTGGGGTCCCATCGCGGTTCAAAGGCAGTGGATATGGGACAGAGTTCACTCTCACCATCA
T L A S G V P S R F K G S G Y G T E F T L T I S GCGACCTGGAGTGTGCCGATGCTGCCACTTACTACTGT (SEQ ID NO: 111)
  D L E C A D A A T Y Y C (SEQ ID NO: 112)

CDR-L3 sequences:
CAATGTACTTATATTGCTAGTAGTTATGGAAATAAT (SEQ ID NO: 113)
Q C T Y I A S S Y G N N (SEQ ID NO: 114)

J Segment sequences:
TTCGGCGGAGGGACCGAGGTGGTGGTCAAA (SEQ ID NO: 115)
F G G G T E V V V K (SEQ ID NO: 116)

7H5/7K1 Heavy Chain Variable (vH) DNA and Amino Acid Sequences* cDNA sequence:
ATGGAGACTGGGCTGCGCTGGCTTCTCCTGGTCGCTGTGCTCAAAGGTGTCCAGTGTCAGGAGCAGCTGG
TGGAGTCCGGGGGAGACCTGGTCAAGCCTGGGGCATCCCTGACACTCACCTGCACAGCCTCTGGATTCTC
CTTCANTAGCAGCTACCACATGTGCTGGGTCCGCCAGGCTCCAGGGAAGGGGCTGGAGTGGATCGCATAC
ATTTATGCTGGTAATAGCGGTGGCACTTACTACGCGAGTTGGGCGAAAGGCCGATTCACCATCTCCAAAG
CCTCGTCGACCACGGTGACTCTGCAAATGACCAGTCTGACAGCCGCGGACACGGCCACCTATTTCTGTGC
GAGAAGGGATACTGGTGGGACCAGTGCTTATGCCTTGTGGGGCCAGGGCACCCTGGTCACCGTCTCGAGC (SEQ ID NO: 117)

Polypeptide sequence:
METGLRWLLLVAVLKGVQCQEQLVESGGDLVKPGASLTLTCTASGFSFXSSYHMCWVRQA
PGKGLEWIAY<u>IYAGNSGGTYYASWAK</u>GRFTISKASSTTVTLQMTSLTAADTATYFC<u>ARRD
TGGTSAYAL</u>WGQGTLVTVSS (SEQ ID NO: 118)

TABLE 1-continued

Identification and sequencing of the leader and variable regions of anti-phosphorylated PD-1 monoclonal antibody, 407.6G12

Annotated sequences:
Leader sequences:
ATGGAGACTGGGCTGCGCTGGCTTCTCCTGGTCGCTGTGCTCAAAGGTGTCCAGTGT (SEQ ID NO: 119)
 M   E   T   G   L   R   W   L   L   L   V   A   V   L   K   G   V   Q   C  (SEQ ID NO: 120)

Framework 1 sequences:
CAGGAGCAGCTGGTGGAGTCCGGGGGAGACCTGGTCAAGCCTGGGGCATCCCTGACACTCACCTGCACAG
 Q   E   Q   L   V   E   S   G   G   D   L   V   K   P   G   A   S   L   T   L   T   C   T   A

CCTCT (SEQ ID NO: 121)
  S  (SEQ ID NO: 122)

CDR-H1 sequences:
GGATTCTCCTTCANTAGCAGCTACCAC (SEQ ID NO: 123)
 G   F   S   F   X   S   S   Y   H  (SEQ ID NO: 124)

Framework 2 sequences:
ATGTGCTGGGTCCGCCAGGCTCCAGGGAAGGGGCTGGAGTGGATCGCATAC (SEQ ID NO: 125)
 M   C   W   V   R   Q   A   P   G   K   G   L   E   W   I   A   Y  (SEQ ID NO: 126)

CDR-H2 sequences:
ATTTATGCTGGTAATAGCGGTGGCACT (SEQ ID NO: 127)
 I   Y   A   G   N   S   G   G   T  (SEQ ID NO: 128)

Framework 3 sequences:
TACTACGCGAGTTGGGCGAAAGGCCGATTCACCATCTCCAAAGCCTCGTCGACCACGGTGACTCTGCAAA
 Y   Y   A   S   W   A   K   G   R   F   T   I   S   K   A   S   S   T   T   V   T   L   Q   M TGACCAGTCTGACAGCCGCGGACACGGCCACCTATTTCTGT (SEQ ID NO: 129)
  T   S   L   T   A   A   D   T   A   T   Y   F   C  (SEQ ID NO: 130)

CDR-H3 sequences:
GCGAGAAGGGATACTGGTGGGACCAGTGCTTATGCCTTG (SEQ ID NO: 131)
 A   R   R   D   T   G   G   T   S   A   Y   A   L  (SEQ ID NO: 132)

J Segment sequences:
TGGGGCCAGGGCACCCTGGTCACCGTCTCGAGC (SEQ ID NO: 133)
 W   G   Q   G   T   L   V   T   V   S   S  (SEQ ID NO: 134)

*CDR definitions and protein sequence numbering according to Kabat. CDR amino acid sequences are underlined in order of CDR1, CDR2, and CDR3, respectively. In addition, Table 1 includes mAb sequences encompassed by the present invention and described herein, such as in the Examples and Figures. Unless otherwise stated, the sequences shown in Table 1 with regard to commonly referenced sequence terms described elsewhere herein will control.

TABLE 2

Representative PD-1 Sequences

Human PD-1 cDNA Acid Sequence (NM_005018.2, CDS from position 69 to position 935)
```
   1  agtttccctt ccgctcacct ccgcctgagc agtggagaag cggcagtctg gtggggctg 61  ctccaggcat gcagatccca caggcgccct ggccagtcgt ctgggcggtg ctacaactgg 121  gctggcggcc aggatggttc ttagactccc cagacaggcc ctggaacccc ccacccttct 181  ccccagccct gctcgtggtg accgaagggg acaacgccac cttcacctgc agcttctcca 241  acacatcgga gagcttcgtg ctaaactggt accgcatgag ccccagcaac cagacggaca 301  agctggccgc cttccccgag gaccgcagcc agcccggcca ggactgccgc ttccgtgtca 361  cacaactgcc caacgggcgt gacttccaca tgagcgtggt cagggcccgg cgcaatgaca 421  gcggcaccta cctctgtggg gccatctccc tggccccaa ggcgcagatc aaagagagcc 481  tgcgggcaga gctcagggtg acagagagaa gggcagaagt gcccacagcc cacccagcc 541  cctcacccag gccagccggc cagttccaaa ccctggtggt tggtgtcgtg ggcggcctgc 601  tgggcagcct ggtgctgcta gtctgggtcc tggccgtcat ctgctcccgg gccgcacgag 661  ggacaatagg agccaggcgc accggccagc ccctgaagga gacccctca gccgtgcctg 721  tgttctctgt ggactatggg gagctggatt tccagtggcg agagaagacc ccggagcccc 781  ccgtgccctg tgtccctgag cagacggagt atgccaccat tgtctttcct agcggaatgg
```

TABLE 2-continued

Representative PD-1 Sequences

```
 841  gcacctcatc ccccgcccgc aggggctcag ctgacggccc tcggagtgcc cagccactga
 901  ggcctgagga tggacactgc tcttggcccc tctgaccggc ttccttggcc accagtgttc
 961  tgcagaccct ccaccatgag cccgggtcag cgcatttcct caggagaagc aggcagggt
1021  caggccattg caggccgtcc aggggctgag ctgcctgggg gcgaccgggg ctccagcctg
1081  cacctgcacc aggcacagcc ccaccacagg actcatgtct caatgcccac agtgagccca
1141  ggcagcaggt gtcaccgtcc cctacaggga gggccagatg cagtcactgc ttcaggtcct
1201  gccagcacag agctgcctgc gtccagctcc ctgaatctct gctgctgctg ctgctgctgc
1261  tgctgctgcc tgcggcccgg ggctgaaggc gccgtggccc tgcctgacgc cccggagcct
1321  cctgcctgaa cttgggggct ggttggagat ggccttggag cagccaaggt gccccctggca
1381  gtggcatccc gaaacgccct ggacgcaggg cccaagactg gcacaggag tgggaggtac
1441  atggggctgg ggactcccca ggagttatct gctccctgca ggcctagaga agtttcaggg
1501  aaggtcagaa gagctcctgg ctgtggtggg cagggcagga aaccccctcca cctttacaca
1561  tgcccaggca gcacctcagg ccctttgtgg ggcagggaag ctgaggcagt aagcgggcag
1621  gcagagctgg aggcctttca ggcccagcca gcactctggc ctcctgccgc cgcattccac
1681  cccagcccct cacaccactc gggagaggga catcctacgg tcccaaggtc aggagggcag
1741  ggctggggtt gactcaggcc cctcccagct gtggccacct gggtgttggg agggcagaag
1801  tgcaggcacc tagggccccc catgtgccca ccctgggagc tctccttgga acccattcct
1861  gaaattattt aaaggggttg gccgggctcc caccagggcc tgggtgggaa ggtacaggcg
1921  ttccccccggg gcctagtacc cccgccgtgg cctatccact cctcacatcc acacactgca
1981  ccccccactcc tggggcaggg ccaccagcat ccaggcggcc agcaggcacc tgagtggctg
2041  ggacaaggga tccccttcc ctgtggttct attatattat aattataatt aaatatgaga
2101  gcatgctaag gaaaa (SEQ ID NO: 135)
```

Human PD-1 Amino Acid Sequence (NP_005009.2)
```
   1  mqipqapwpv vwavlqlgwr pgwfldspdr pwnpptfspa llvvtegdna tftcsfsnts
  61  esfvlnwyrm spsnqtdkla afpedrsqpg qdcrfrvtql pngrdfhmsv vrarrndsgt
 121  ylcgaislap kaqikeslra elrvterrae vptahpspsp rpagqfqtlv vgvvgllgs
 181  lvllvwvlav icsraargti garrtgqplk edpsavpvfs vdygeldfqw rektpeppvp
 241  cvpeqteyat ivfpsgmgts sparrgsadg prsaulrpe dghcswpl (SEQ ID NO: 136)
```

Mouse PD-1 cDNA Acid Sequence (NM_008798.2, CDS from position 64 to position 930)
```
   1  tgagcagcgg ggaggaggaa gaggagactg ctactgaagg cgacactgcc aggggctctg
  61  ggcatgtggg tccggcaggt accctggtca ttcacttggg ctgtgctgca gttgagctgg
 121  caatcagggt ggcttctaga ggtccccaat gggccctgga ggtccctcac cttctaccca
 181  gcctggctca cagtgtcaga gggagcaaat gccaccttca cctgcagctt gtccaactgg
 241  tcggaggatc ttatgctgaa ctggaaccgc ctgagtccca gcaaccagac tgaaaaacag
 301  gccgccttct gtaatggttt gagccaaccc gtccaggatg cccgcttcca gatcatacag
 361  ctgcccaaca gcatgactt ccacatgaac atccttgaca cacggcgcaa tgacagtggc
 421  atctacctct gtggggccat ctccctgcac cccaaggcaa aaatcgagga gagccctgga
 481  gcagagctcg tggtaacaga gagaatcctg gagacctcaa caagatatcc cagcccctcg
 541  cccaaaccag aaggccggtt caaggcatg gtcattggta tcatgagtgc cctagtgggt
 601  atccctgtat tgctgctgct ggcctgggcc ctagctgtct tctgctcaac aagtatgtca
```

TABLE 2-continued

Representative PD-1 Sequences

```
 661   gaggccagag gagctggaag caaggacgac actctgaagg aggagccttc agcagcacct
 721   gtccctagtg tggcctatga ggagctggac ttccagggac gagagaagac accagagctc
 781   cctaccgcct gtgtgcacac agaatatgcc accattgtct tcactgaagg gctgggtgcc
 841   tcggccatgg gacgtagggg ctcagctgat ggcctgcagg gtcctcggcc tccaagacat
 901   gaggatggac attgttcttg gcctctttga ccagattctt cagccattag catgctgcag
 961   accctccaca gagagcaccg gtccgtccct cagtcaagag gagcatgcag gctacagttc
1021   agccaaggct cccagggtct gagctagctg gagtgacagc ccagcgcctg caccaattcc
1081   agcacatgca ctgttgagtg agagctcact tcaggtttac cacaagctgg gagcagcagg
1141   cttcccggtt tcctattgtc acaaggtgca gagctggggc ctaagcctat gtctcctgaa
1201   tcctactgtt gggcacttct agggacttga gacactatag ccaatggcct ctgtgggttc
1261   tgtgcctgga aatggagaga tctgagtaca gcctgctttg aatggccctg tgaggcaacc
1321   ccaaagcaag ggggtccagg tatactatgg gcccagcacc taaagccacc cttgggagat
1381   gatactcagg tgggaaattc gtagactggg ggactgaacc aatcccaaga tctggaaaag
1441   ttttgatgaa gacttgaaaa gctcctagct tcgggggtct gggaagcatg agcacttacc
1501   aggcaaaagc tccgtgagcg tatctgctgt ccttctgcat gcccaggtac ctcagttttt
1561   ttcaacagca aggaaactag ggcaataaag ggaaccagca gagctagagc cacccacaca
1621   tccagggggc acttgactct ccctactcct cctaggaacc aaaaggacaa agtccatgtt
1681   gacagcaggg aaggaaaggg ggatataacc ttgacgcaaa ccaacactgg ggtgttagaa
1741   tctcctcatt cactctgtcc tggagttggg ttctggctct ccttcacacc taggactctg
1801   aaatgagcaa gcacttcaga cagtcagggt agcaagagtc tagctgtctg gtgggcaccc
1861   aaaatgacca gggcttaagt cccttcctt tggtttaagc ccgttataat taaatggtac
1921   caaaagcttt aaaaaaaaaa aaaaaaaaaa aaaaaaaaaa aaaaaaaaa aa (SEQ ID NO: 138)
```

Mouse PD-1 Amino Acid Sequence (NP_032824.1)
```
   1   mwvrqvpwsf twavlqlswq sgwllevpng pwrsltfypa wltvsegana tftcslsnws
  61   edlmlnwnrl spsnqtekqa afcnglsqpv qdarfqiiql pnrhdfhmni ldtrrndsgi
 121   ylcgaislhp kakieespga elvvterile tstrypspsp kpegrfqgmv igimsalvgi
 181   pvllllawal avfcstsmse argagskddt lkeepsaapv psvayeeldf qgrektpelp
 241   tacvhteyat ivfteglgas amgrrgsadg lqgprpprhe dghcswpl (SEQ ID NO: 139)
```

*Included in Table 2 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO or biomarker described in Table 2, or a portion thereof. Such nucleic acid molecules can have a function of the full-length nucleic acid as described further herein.
*Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO or biomarker described in Table 2, or a portion thereof Such polypeptides can have a function of the full-length polypeptide as described further herein.

III. Nucleic Acids, Vectors, and Recombinant Host Cells

A further object of the invention relates to nucleic acid sequences encoding monoclonal antibodies and fragments thereof, immunoglobulins, and polypeptides of the present invention.

In a particular embodiment, the invention relates to a nucleic acid sequence encoding the vH domain and/or vL domain of a mAb described herein, such as that of mAbs 6G12, 2H2/2K4, 6H2/6K2, and 7H5/7K1.

In another particular embodiment, the invention relates to a nucleic acid sequence encoding the vH domain or the vL domain of at least one effective anti-phospho-PD-1 mAb isolated from the polyclonal antibodies 1.2 and/or 2.2.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the invention relates to a vector comprising a nucleic acid of the present invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv-positive cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

The nucleic acids of the present invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL 1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the invention according to the invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the invention.

In another aspect, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences. Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

IV. Methods of Producing Antibodies

Antibodies and fragments thereof, immunoglobulins, and polypeptides of the present invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies and other polypeptides of the present invention can be synthesized by recombinant DNA techniques as is well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In particular, the present invention further relates to a method of producing an antibody or a polypeptide of the invention, which method comprises the steps consisting of: (i) culturing a transformed host cell according to the invention under conditions suitable to allow expression of said antibody or polypeptide; and (ii) recovering the expressed antibody or polypeptide.

Antibodies and other polypeptides of the present invention are suitably separated from the culture medium by conventional immunoglobulin purification procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Chimeric antibodies (e.g., mouse-human chimeras) of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. The CH domain of a human chimeric antibody can be any region which belongs to human immunoglobulin, such as the IgG class or a subclass thereof, such as IgG1, IgG2, IgG3 and IgG4. Similarly, the CL of a human chimeric antibody can be any region which belongs to Ig, such as the kappa class or lambda class. chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. Humanized antibodies of the present invention can be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type).

Methods for producing humanized antibodies based on conventional recombinant DNA and gene transfection techniques are well known in the art (See, e.g., Riechmann L et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Similarly, bispecific or multispecific antibodies described herein can be made according to standard procedures. For example, triomas and hybrid hybridomas are two examples of cell lines that can secrete bispecific or multispecific antibodies. Examples of bispecific and multispecific antibodies produced by a hybrid hybridoma or a trioma are disclosed in U.S. Pat. No. 4,474,893. Such antibodies can also be constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Alternatively, such antibodiescan also be generated by making heterohybridomas by fusing hybridomas or other cells making different antibodies, followed by identification of clones producing and co-assembling the desired antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more immunoinhibitory biomarkers described herein.

In addition, methods for producing antibody fragments are well known. For example, Fab fragments of the present invention can be obtained by treating an antibody which specifically reacts with at least one of the phosphorylation sites (e.g., Y248) of human PD-1 (such as mAbs 6G12, 2H2/2K4, 6H2/6K2, and 7H5/7K1, and polyclonal antibodies 1.2 and 2.2) with a protease, papaine. Also, Fabs can be produced by inserting DNA encoding Fabs of the antibody into a vector for prokaryotic expression system, or for eukaryotic expression system, and introducing the vector into a procaryote or eucaryote (as appropriate) to express the Fabs.

Similarly, F(ab')2 fragments of the present invention can be obtained treating an antibody which specifically reacts with at least one of the phosphorylation sites (e.g., Y248) of PD-1 with a protease, pepsin. Also, the F(ab')2 fragment can be produced by binding Fab' described below via a thioether bond or a disulfide bond.

Fab' fragments of the present invention can be obtained treating F(ab')2 which specifically reacts with at least one of the phosphorylation sites (e.g., Y248) of human PD-1 with a reducing agent, dithiothreitol. Also, the Fab' fragments can be produced by inserting DNA encoding a Fab' fragment of the antibody into an expression vector for prokaryote, or an expression vector for eukaryote, and introducing the vector into a prokaryote or eukaryote (as appropriate) to perform its expression.

In addition, scFvs of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

V. Modification of Antibodies, Immunoglobulins, and Polypeptides

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In one embodiment, amino acid changes may be achieved by changing codons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

Genetic Code

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8);

glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6 diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies that specifically bind at least one of the phosphorylation sites (e.g., Y248) of PD-1 conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-phosphorylated PD-1 antibodies can be used diagnostically or prognostically to monitor polypeptide levels in tissue as part of a clinical testing procedure, e.g., to determine the efficacy of a given treatment regimen or to select patients most likely to response to an immunotherapy. For example, cells can be permeabilized in a flow cytometry assay to allow antibodies that bind at least one of the phosphorylation sites (e.g., Y248) of PD-1 (such as mAbs 6G12, 2H2/2K4, 6H2/6K2, and 7H5/7K1, and polyclonal antibodies 1.2 and 2.2) to target its recognized intracellular epitope and allow detection of the binding by analyzing signals emanating from the conjugated molecules. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

VI. Uses and Methods of the Invention

The anti-phosphorylated PD-1 antibodies, immunoglobulins, polypeptides, and nucleic acids of the present invention described herein can be used in numerous predictive medicine assays (e.g., diagnostic assays, prognostic assays, and monitoring clinical trials) based on detection of phosphorylated PD-1 levels and, in some embodiments and can be useful for therapeutic purposes (e.g., therapeutic and prophylactic) either alone or when conjugated to toxic compounds or other therapeutics. The term "detection" as used herein includes qualitative and/or quantitative detection (measuring levels) with or without reference to a control. As described herein, a phosphorylated PD-1 polypeptide or fragment thereof of the present invention has one or more of the following activities: 1) binds to and/or modulates the activity of its natural binding partner(s), such as PD-L1 or PD-L2; 2) modulates intra- or intercellular signaling, such as co-immunoinhibitory signaling; 3) modulates activation and/or proliferation of lymphocytes; 4) modulates the immune response of an organism, e.g., a mammalian organism, such as a mouse or human; and 5) modulates immune cell anergy.

Thus, one aspect of the present invention relates to diagnostic assays for determining phosphorylated PD-1 polypeptide levels in the context of a biological sample (e.g., blood, serum, cells, or tissue) to thereby determine the level of phosphorylated PD-1 polypeptide in the sample, to determine whether an individual is afflicted with a disorder and/or to determine the state of such a disorder, indicated by such phosphorylated PD-1 levels. For example, antibodies of the present invention are useful for staging cancer diseases associated with aberrant PD-1 phosphorylation.

The present invention also provides for prognostic (or predictive) assays for determining whether an individual is at risk of developing such a disorder. Another aspect of the present invention pertains to monitoring the influence of agents (e.g., drugs, compounds) on the expression or activity of phosphorylated PD-1 in clinical trials.

The present invention also provides for detection of PD-1 phosphorylation as a means to identify agents that transduce a PD-1 signal. Agents that transduce a PD-1 signal would attenuate immune responses and might be useful in autoimmune diseases, asthma, and for the establishment of tolerance.

In any method described herein, PD-1 phosphorylation can be detected either alone or in combination with the expression of other molecules, such as other immune checkpoint and/or costimulatory molecules. Combinatorial detection (e.g., sequentially or simultaneously) of several molecules can provide useful information regarding synergies of therapeutic intervention and/or personalized, higher-resolution diagnoses of disorder subtypes. In some embodiments, PD-1 phophorylation is combinatorially detected with one more markers.

1. Diagnostic Assays

The present invention provides, in part, methods, systems, and code for accurately classifying whether a biological sample expresses cell-restricted PD-1 phosphorylation and/or whether the levels of cell-restricted PD-1 phosphorylation are modulated (e.g., upregulated or downregulated), thereby indicative of the state of a disorder of interest, such as cancer. In some embodiments, the present invention is useful for classifying a sample (e.g., from a subject) as associated with or at risk for cancer or a subtype thereof, mediated by PD-1 phosphorylation using a statistical algorithm and/or empirical data (e.g., the presence, absence, or level of PD-1 phosphorylation).

An exemplary method for detecting the level of phosphorylation of PD-1 or fragments thereof, and thus useful for classifying whether a sample is associated with a disease or disorder mediated by an aberrant PD-1 phosphorylation or a clinical subtype thereof involves obtaining a biological sample from a test subject and contacting the biological sample with an antibody or antigen-binding fragment thereof of the present invention capable of detecting PD-1 phosphorylation such that the level of phosphorylated PD-1 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a PD-1 sample based upon a prediction or probability value and the presence or level of PD-1 phosphorylation. The use of a single learning statistical classifier system typically classifies the sample as a phosphorylated PD-1 sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the phosphorylated PD-1 sample classification results to a clinician, e.g., a histopathologist or an oncologist.

In another embodiment, the method of the present invention further provides a diagnosis in the form of a probability that the individual has a condition or disorder associated with aberrant PD-1 phosphorylation. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a phosphorylated PD-1 sample is further based on the symptoms (e.g., clinical factors) of the individual from which the sample is obtained. The symptoms or group of symptoms can be, for example, lymphocyte count, white cell count, erythrocyte sedimentation rate, diarrhea, abdominal pain, cramping, fever, anemia, weight loss, anxiety, depression, and combinations thereof. In some embodiments, the diagnosis of an individual as having a condition or disorder associated with aberrant PD-1 phosphorylation is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by aberrant PD-1 phosphorylation), a biological sample from the subject during remission or before developing a condition or disorder mediated by aberrant PD-1 phosphorylation, or a biological sample from the subject during treatment for developing a condition or disorder mediated by aberrant PD-1 phosphorylation.

An exemplary method for detecting the presence or absence of phosphorylated PD-1 polypeptide or fragments thereof is an antibody of the present invention, or fragment thereof, capable of binding to a phosphorylated PD-1 polypeptide, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect phosphorylated PD-1, or fragments thereof, in a biological sample in vitro as well as in vivo. In vitro techniques for detection of phosphorylated PD-1 polypeptide include enzyme linked immunosorbent assays (ELISAs), Western blots, immunoprecipitations, immunohistochemistry (IHC), intracellular flow cytometry and related techniques, and immunofluorescence. Furthermore, in vivo techniques for detection of a phosphorylated PD-1 polypeptide or a fragment thereof include introducing into a subject a labeled anti-phosphorylated PD-1 antibody. For example, the antibody can be labeled with a radioactive, luminescent, fluorescent, or other similar marker whose presence and location in a subject can be detected by standard imaging techniques, either alone or in combination with imaging for other molecules, such as markers of cell type (e.g., CD8+ T cell markers).

In one embodiment, the biological sample contains polypeptide molecules from the test subject. A preferred biological sample is a serum, tumor microenvironment, peritumoral, or intratumoral, isolated by conventional means from a subject.

In another embodiment, the methods further involve obtaining a control biological sample from a control subject, contacting the control sample with a compound or agent capable of detecting phosphorylated PD-1 polypeptide, or fragments thereof, such that the presence of phosphorylated PD-1 polypeptide, or fragments thereof, is detected in the biological sample, and comparing the presence of phosphorylated PD-1 polypeptide, or fragments thereof, in the control sample with the presence of phosphorylated PD-1 polypeptide, or fragments thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of phosphorylated PD-1 by use of an immunochromatographic or immunochemical assay, such as in a "sandwich" or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" phosphorylated PD-1 polypeptides in a biological sample and the captured (or immobilized) phosphorylated PD-1 polypeptides may be bound to a labeled form of an anti-phosphorylated PD-1 antibody of the invention for detection. Other standard embodiments of immunoassays are well known the skilled artisan, including assays based on, for example, immunodiffusion, immunoelectrophoresis, immunohistopathology, immunohistochemistry, and histopathology.

2. Prognostic Assays

The diagnostic methods described herein can furthermore be utilized to identify subjects having or at risk of developing a disorder associated with aberrant or undesired PD-1 phosphorylation. As used herein, the term "aberrant" includes a PD-1 phosphorylation which deviates from the wild type or normal PD-1 phosphorylation. Aberrant expression or activity includes increased or decreased expression or activity, as well as expression or activity which does not follow the wild type developmental pattern of expression or the subcellular pattern of expression. For example, aberrant phosphorylated PD-1 levels is intended to include the cases in which a mutation in the PD-1 gene or regulatory sequence, or amplification of the chromosomal PD-1 gene, thereof causes the PD-1 gene to be under-phosphorylated or over-phosphorylated and situations in which such mutations result in a non-functional phosphorylated PD-1 polypeptide or a polypeptide which does not function in a wild-type fashion, e.g., a polypeptide missing an intracellular domain and thus not able to interact with a PD-1 binding or signal partner. As used herein, the term "unwanted" includes an unwanted phenomenon involved in a biological response such as immune cell activation. For example, the term unwanted includes a PD-1 phosphorylation which is undesirable in a subject.

Many disorders associated with aberrant PD-1 phosphorylation are known to the skilled artisan, as explained further in the Examples. PD-1 is expressed by multiple tumor types, including select lymphoid malignancies, virally-induced cancers, and many solid tumors. Generally, PD-1 phosphorylation is an adverse prognostic marker because it activates immune checkpoint regulators and other PD-1 pathway responders that inhibit strong immune responses against conditions in need thereof. However, immunoinhibition is desired for downregulating immune responses in treating a number of disorders, such as autoimmune diseases, inflammatory diseases, and the like.

The assays described herein, such as the preceding diagnostic assays or the following assays, can be utilized to identify a subject having or at risk of developing a disorder associated with a misregulation of PD-1 activation, represented by PD-1 phosphorylation. Thus, the present invention provides a method for identifying a disorder associated with aberrant or unwanted PD-1 activation in which a test sample is obtained from a subject and PD-1 phosphorylation is detected, wherein the presence of phosphorylated PD-1 polypeptide is diagnostic for a subject having or at risk of developing the disorder associated with aberrant or unwanted PD-1 activity. As used herein, a "test sample" refers to a biological sample obtained from a subject of interest. For example, a test sample can be a biological fluid (e.g., cerebrospinal fluid or serum), cell sample, or tissue, such as a histopathological slide of the tumor microenvironment, peritumoral area, and/or intratumoral area. In a preferred embodiment, the sample comprises cells expressing mature membrane-bound PD-1 and/or PD-1 fragments containing at least one of its phosphorylation sites.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat such a disorder associated with aberrant or unwanted PD-1 activity. For example, such methods can be used to determine whether a subject can be effectively treated with one or a combination of agents. Thus, the present invention provides methods for determining whether a subject can be effectively treated with one or more agents for treating a disorder associated with aberrant or unwanted PD-1 activation in which a test sample is obtained and PD-1 phosphorylation is detected (e.g., wherein the abundance of phosphorylated PD-1 polypeptide is diagnostic for a subject that can be administered the agent to treat the disorder associated with aberrant or unwanted PD-1 activation).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving PD-1.

Furthermore, any cell type or tissue in which PD-1 is expressed may be utilized in the prognostic assays described herein.

Another aspect of the present invention includes uses of the compositions and methods described herein for association and/or stratification analyses in which the phosphorylation of PD-1 in biological samples from individuals with a disorder associated with aberrant PD-1 activation, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs well known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a phosphorylated PD-1 level with certain phenotypic characteristics of a disease. It is preferred that a p-value <0.05 (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

3. Monitoring of Effects During Clinical Trials

Monitoring the influence of agents (e.g., compounds, drugs or small molecules) on the phosphorylation of a PD-1 polypeptide or a fragment thereof (e.g., the modulation of cell proliferation and/or migration) can be applied not only in basic drug screening, but also in clinical trials. For example, the effectiveness of an agent determined by a screening assay as described herein to decrease PD-1 gene expression, polypeptide levels, or downregulate PD-1 activity, can be monitored in clinical trials of subjects exhibiting decreased PD-1 gene expression, polypeptide levels, or downregulated PD-1 activity, or can be monitored in clinical trails of subjects exhibiting decreased phosphorylated PD-1, detectable by the anti-phosphorylated PD-1 antibodies or fragments described herein. In such clinical trials, the expression or activity of a PD-1 gene (e.g., identified in its phosphorylation levels) and/or symptoms or markers of the disorder of interest, can be used as a "read out" or marker of the phenotype of a particular cell, tissue, or system. Similarly, the effectiveness of an agent determined by a screening assay as described herein to increase PD-1 gene expression, polypeptide levels, or increase PD-1 activity, can be monitored in clinical trials of subjects exhibiting increased PD-1 gene expression, polypeptide levels, or increased PD-1 activity, or can be monitored in clinical trails of subjects exhibiting increased phosphorylated PD-1, detectable by the anti-phosphorylated PD-1 antibodies or fragments described herein. In such clinical trials, the expression or activity of a PD-1 gene (e.g., identified in its phosphorylation levels) and/or symptoms or markers of the disorder of interest, can be used as a "read out" or marker of the phenotype of a particular cell, tissue, or system, such as for an autoimmune disorder.

For example, and not by way of limitation, genes, including PD-1, that are modulated in cells by treatment with an agent (e.g., compound, drug or small molecule) which modulates PD-1 activity (e.g., identified in a screening assay as described herein) can be identified. Thus, to study the effect of agents on a disorder associated with aberrant PD-1 activation, for example, in a clinical trial, cells can be isolated and nucleic acids and/or protein prepared and analyzed for the levels of phosphorylated PD-1 and/or other genes implicated in the disorder associated with aberrant PD-1 activation. The levels of gene expression (e.g., a gene expression pattern) analyzed by measuring the amount of polypeptide produced, by one of the methods as described herein, or by measuring the levels of phosphorylated PD-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of phosphorylated PD-1 polypeptides, or fragments thereof, in the preadministration sample; (iii) obtaining one or more post-administration samples from the subject; (iv) detecting the level of phosphorylated PD-1 polypeptides, or fragments thereof, in the post-administration samples; (v) comparing the level of the phosphorylated PD-1 polypeptide, or fragments thereof, in the pre-administration sample with the phosphorylated PD-1 polypeptide in the post administration sample or samples; and (vi) altering the administration of the agent to the subject accordingly. For example, increased administration of the agent may be desirable to decrease the phosphorylated PD-1 to lower levels than detected, i.e., to increase the effectiveness of the agent. According to such an embodiment, PD-1 phosphorylattion may be used as an indicator of the effectiveness of an agent, even in the absence of an observable phenotypic response. Similarly, PD-1 phosphorylation analysis, such as by immunohistochemistry (IHC), can also be used to select patients who will receive PD-1 and/or PD-1 immunotherapy, or immunotherapy to inhibit one ore more immune checkpoints. Patients whose tumors having PD-1 activation are more likely to respond to PD-1 or PD-1 mAb immunotherapy, as described herein. The immunotherapy will initially result in immune activation and the activated T cells will express IFN-gamma which in turn will upregulate PD-1 activation. Normally this would result in PD-1 engagement and down regulation of the immune response, but because PD-1 ma be blocked by the anti-phosphorylated PD-1 mAb as described herein, the immune response continues until a desired condition, such as a tumor, is eliminated. By contrast, mAbs that actively signal through PD-1 directly downregulate an immune response.

4. Therapeutic Methods and Uses

In some embodiments, antibodies, fragments or immunoconjugates of the present invention (e.g., anti-phosphorylated PD-1 antibodies alone or conjugated to therapeutic moieties) are useful for treating any disorder (e.g., a cancer) associated with aberrant or undesired activation of PD-1. In certain embodiments, the treatment is of a mammal, such as a human. Such antibodies of the invention may be used alone or in combination with any suitable agent or appropriate therapy to treat the disorder of interest. For example, therapeutic synergies are believed to become manifested when treating a cell comprising phosphorylated PD-1 and another immune checkpoint or costimulatory molecule.

It is well known that therapeutic monoclonal antibodies can lead to the depletion of cells extracellularly bearing the antigen specifically recognized by the antibody. This depletion can be mediated through at least three mechanisms: antibody mediated cellular cytotoxicity (ADCC), complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed. As is well known in the art, the Fc portions can be engineered to effect a desired interaction or lack thereof with Fc receptors.

For antibody-mediated binding, neutralization, and/or modulation of intracellular targets, certain modifications should be made. As described herein, certain antibody formats, such as sFvs and Fabs, are amenable to intracellular expression of antibody-like molecules. Methods of making and using such adapted antibody-like molecules for targeting expression in different compartments of the cell, including the nucleus, ER, cytoplasm, golgi, plasma membrane, mitochondria, where they counteract antigens or molecules in a specific pathway, are well known (see, at least U.S. Pat. Publs. 2008-0233110 and 2003-0104402; Marasco et al. (1993) *Proc. Natl. Acad. Sci. U.S.A.* 90:7889-7893; Chen et al. (1994) *Human Gene Therapy* 5:595-601; Chen et al. (1994) *Proc. Natl. Acad. Sci. U.S.A.* 91:5932-5936; Mhashilkar et al. (1995) *EMBO J.* 14:1542-1551; Marasco et al. (1997) *Gene Therapy* 4:11-15; Richardson et al. (1995) *Proc. Natl. Acad. Sci. U.S.A.* 92:3137-3141; and Duan et al. (1994) *Human Gene Therapy* 5:1315-1324).

As used herein, the term "intracellular immunoglobulin molecule" is a complete immunoglobulin which is the same as a naturally-occurring secreted immunoglobulin, but which remains inside of the cell following synthesis. An "intracellular immunoglobulin fragment" refers to any fragment, including single-chain fragments of an intracellular immunoglobulin molecule. Thus, an intracellular immunoglobulin molecule or fragment thereof is not secreted or expressed on the outer surface of the cell. Single-chain intracellular immunoglobulin fragments are referred to herein as "single-chain immunoglobulins." As used herein, the term "intracellular immunoglobulin molecule or fragment thereof" is understood to encompass an "intracellular immunoglobulin," a "single-chain intracellular immunoglobulin" (or fragment thereof), an "intracellular immunoglobulin fragment," an "intracellular antibody" (or fragment thereof), and an "intrabody" (or fragment thereof). As such, the terms "intracellular immunoglobulin," "intracellular Ig," "intracellular antibody," and "intrabody" may be used interchangeably herein, and are all encompassed by the generic definition of an "intracellular immunoglobulin molecule, or fragment thereof." An intracellular immunoglobulin molecule, or fragment thereof of the present invention may, in some embodiments, comprise two or more subunit polypeptides, e.g., a "first intracellular immunoglobulin subunit polypeptide" and a "second intracellular immunoglobulin subunit polypeptide." However, in other embodiments, an intracellular immunoglobulin may be a "single-chain intracellular immunoglobulin" including only a single polypeptide. As used herein, a "single-chain intracellular immunoglobulin" is defined as any unitary fragment that has a desired activity, for example, intracellular binding to an antigen. Thus, single-chain intracellular immunoglobulins encompass those which comprise both heavy and light chain variable regions which act together to bind antigen, as well as single-chain intracellular immunoglobulins which only have a single variable region which binds antigen, for example, a "camelized" heavy chain variable region as described herein. An intracellular immunoglobulin or Ig fragment may be expressed anywhere substantially within the cell, such as in the cytoplasm, on the inner surface of the cell membrane, or in a subcellular compartment (also referred to as cell subcompartment or cell compartment) such as the nucleus, golgi, endoplasmic reticulum, endosome, mitochondria, etc. Additional cell subcompartments include those that are described herein and well known in the art.

Such intracellular immunoglobulins are expressed in a recipient cell or host cell containing the antigen to be targeted. A host cell of the present invention is preferably a eukaryotic cell or cell line, preferably a plant, animal, vertebrate, mammalian, rodent, mouse, primate, or human cell or cell line.

Without being bound by theory, it is believed that intracellular expression of the immunoglobulin polypeptides described herein allow for the intracellular targeting and binding to phosphorylation sites of PD-1 to thereby sterically modulate the molecule's ability to signal by, for example, modulating its ability to propagate signaling upon activation by binding to PD-L1, PD-L2, B7-4, and the like and/or to modulate signaling upon increasing the local effective concentration of multiple phosphorylated PD-1 molecules. The effects of modulating PD-1 signaling are well known in the art (see, for example, PCT Publ. WO 2001/014557).

In some embodiments, antibodies of the present invention can be conjugated to a therapeutic moiety, such as a growth inhibitory agent, cytotoxic agent, or a prodrug-activating enzyme as previously described. Antibodies of the invention can be useful for targeting said growth inhibitory agent, cytotoxic agent, or a prodrug to a cell that under- or over-expresses the desired amount of phosphorylated PD-1.

Thus, an object of the invention relates to a method for treating a disorder associated with aberrant PD-1 activation comprising administering a subject in need thereof with a therapeutically effective amount of an antibody, fragment or immunoconjugate of the present invention.

Alternatively, in some embodiments, the antibodies or the antigen-binding fragments of the present invention are useful for therapeutic applications, in addition to diagnostic, prognostic, and prevention applications regarding upregulating an immune response. Upregulation of immune responses can be in the form of enhancing an existing immune response or eliciting an initial immune response. For instance, enhancing an immune response using the subject compositions and methods is useful in cases of improving an immunological defense against cancer and infections with microbes (e.g., bacteria, viruses, or parasites). For example, upregulation or enhancement of an immune response function, as described herein, is useful in the induction of tumor immunity. In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In certain instances, it may be desirable to further administer other agents that upregulate immune responses, for example, forms of other B7 family members that transduce signals via costimulatory receptors, in order to further augment the immune response. Also, agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

Alternatively, in some embodiments, the antibodies and the antigen-binding fragments of the present invention are useful for therapeutic applications, in addition to diagnostic, prognostic, and prevention applications (such as treating, and delaying the onset or progression of the diseases), to inhibit diseases that upregulate the immune reaction, for example, asthma, autoimmune diseases (glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia pemiciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis).

Similarly, the antibodies and the antigen-binding fragments of the present invention are useful for therapeutic applications, in addition to diagnostic, prognostic, and prevention applications (such as treating, and delaying the onset or progression of the diseases) for persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Other antigens associated with pathogens that can be used as described herein are antigens of various parasites, includes malaria, preferably malaria peptide based on repeats of NANP. In addition, bacterial, fungal and other pathogenic diseases are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus,*

*Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium*.

In still another embodiment, the antibodies or the antigen-binding fragments of the present invention are useful for therapeutic applications, in addition to diagnostic, prognostic, and prevention applications regarding induction of immunological tolerance, organ graft rejection, graft-versus-host disease (GVHD), allergic disease, and diseases caused by attenuation of immune reactions mediated by PD-1.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth and/or proliferation of cancer cells. Preferably such treatment also leads to the regression of tumor growth (i.e., the decrease in size of a measurable tumor). Most preferably, such treatment leads to the complete regression of the tumor.

In some embodiments, the term "patient" or "patient in need thereof" is intended for a human or non-human mammal affected or likely to be affected with a cancer associated with aberrant activation of PD-1.

By a "therapeutically effective amount" of the polypeptide of the invention is meant a sufficient amount of the antibody to treat the disorder of interest, such as cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutic dose can be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The composition need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (amphiphilic non-ionic triblock co-polymers) or polyethylene glycol (PEG). Formulations to be used for in vivo administration must be sterile. This is readily accomplished by filtration through sterile filtration membranes.

The active ingredients can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The compositions described herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the compositions can be suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

5. Assays and Screening Methods

Another aspect of the present invention relates to screening assays, including non-cell based assays and xenograft animal model assays. In one embodiment, the assays provide a method for identifying agents that modulate PD-1 signaling, such as in a human or an animal model assay, in order to identify agents that reduce PD-1 signaling thereby increasing immune responses and/or identify agents that increase PD-1 signaling thereby decreasing immune responses.

In one embodiment, the present invention relates to assays for screening test agents which bind to, or modulate the biological activity of, at least one biomarker described herein (e.g., in the tables, figures, examples, or otherwise in the specification), such as PD-1. In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

PD-1 phosphorylation status can be measured using the anti-phosphotyrosinylated PD-1 antibodies described herein. A reduction in phosphorylated PD-1 indicates that the agent inhibits PD-1 activity/signaling and identifies an agent as useful for inhibiting PD-1 activity/signaling and for increasing immune responses. By contrast, an increase in phosphorylated PD-1 indicates that the agent promotes PD-1 activity/signaling and identifies an agent as useful for promoting PD-1 activity/signaling and for reducing immune responses.

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

VII. Kits

In addition, the present invention also encompasses kits for detecting the presence of a phosphorylated PD-1 polypeptide, or fragments thereof, in a biological sample. For example, the kit can comprise a labeled compound or agent capable of detecting a phosphorylated PD-1 polypeptide, or fragments thereof, in a biological sample; means for determining the amount of the phosphorylated PD-1 polypeptide, or fragments thereof, in the sample; and means for comparing the amount of the phosphorylated PD-1 polypeptide, or fragments thereof, in the sample with a standard. The compound or agent can be packaged in a suitable container. For example, the present invention provides kits comprising at least one antibody described herein. Kits containing antibodies of the invention find use in detecting phosphorylated PD-1, or in therapeutic or diagnostic assays. Kits of the invention can contain an antibody coupled to a solid support, e.g., a tissue culture plate or beads (e.g., sepharose beads).

A kit can include additional components to facilitate the particular application for which the kit is designed. For example, kits can be provided which contain antibodies for detection and quantification of phosphorylated PD-1 in vitro, e.g. in an ELISA or a Western blot. Additional, exemplary agents that kits can contain include means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or PD-1 protein standards). A kit may additionally include buffers and other reagents recognized for use in a method of the disclosed invention. Non-limiting examples include agents to reduce non-specific binding, such as a carrier protein or a detergent. A kit of the present invention can also include instructional materials disclosing or describing the use of the kit or an antibody of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods Used in Example 2 a. Cell Lines

MC38 adenocarcinoma were cultured in DMEM supplemented with 10% FBS. 4T1, EL4, Jurkat E6 cell lines were maintained in RPMI1640 media supplemented with 10% FBS (R10). 300.19 cells were maintained in R10 plus 50 µM 2-mercaptoethanol. 300-mPD-1 and Jurkat-hPD-1 stable cell lines were established in the lab, while 300-mPD-1 was maintained in R10 supplemented with 5 µg/ml puromycin and 2-mercaptoethanol. Jurkat-hPD-1 was maintained in R10 supplemented with 5 µg/ml blasticiCdin.

b. Mice

Mice 6-10 weeks of age were used for all experiments. Wild-type C57BL/6 mice and TCRα$^{-/-}$ were purchased from the Jackson Laboratory. P14 TCR Tg and PD-1$^{-/-}$ mice have been previously described in Keir et al. (2007) *J. Immunol.* 179:5064-5070 and Pircher et al. (1989) *Nature* 342:559-561. All experimental mice were housed in specific pathogen-free conditions and used in accordance with animal care guidelines from the Harvard Medical School Standing Committee on Animals and the National Institutes of Health. Animal protocols were approved by the Harvard Medical School Standing Committee on Animals.

c. Generation of Phospho-PD-1 Antibody

100 µg of human PD-1 p248Tyr peptide (CKK-aminocaproic acid-VPEQTE[pY]ATIVF-amide) conjugated to KLH was suspended in PBS and emulsified in complete Freund's adjuvant (Sigma, St. Louis, MO). Mice were immunized by injection of the emulsion at three subcutaneous (s.c.) sites and one intraperitoneal site on day 0. Mice were given boosters in incomplete Freund's adjuvant on day 14 (100 µg PD-1 p248Tyr peptide conjugated to OVA given s.c.), day 28 (100 µg PD-1 p248Tyr peptide conjugated to KLH given s.c.) and day 56 (50 µg PD-1 p248Tyr peptide conjugated to KLH in PBS given intravenously). On day 60, mice were euthanized and single-cell suspensions from the spleen were mixed with SP2/0 myeloma cells (ATCC No. CRL8-006) that are incapable of secreting either heavy or light chain immunoglobulin chains (Kearney et al. (1979) *J. Immunol.* 123:1548-1550) at a splenocyte:myeloma ratio of 2:1. Cells were fused with polyethylene glycol 1450 (ATCC) in 12 96-well tissue culture plates in HAT selection medium according to standard procedures (Kohler and Milstein (1975) *Nature* 256:495-497). Hybridoma wells were screened by western blot on pervanadate treated Jurkat-hPD-1 lysates and by ELISA on PD-1 p248Tyr peptide conjugated to BSA and lack of reactivity to unphosphorylated peptide or BSA. Clone 407.6G12 (mouse IgG2a, kappa) was selected, subcloned and purified mAb prepared.

d. Western Blot

Jurkat hPD-1 cells were treated with 0.1 mM pervanadate for 5 min at 37° C. and lysates prepared (Chemnitz et al. (2006) *J. Immunol.* 176:6603-6614; O'Shea et al. (1992) *Proc. Natl. Acad. Sci. USA* 89:10306-10310). Cells were lysed in RIPA buffer supplemented with Protease Inhibitor Cocktail (Roche, Basel, Switzerland). Cell lysates (20 µg) were separated on 4-15% Mini-PROTEAN® TGX™ gels (Bio-Rad, Hercules, CA) and transferred onto Nitrocellulose Blotting membrane (Amersham, Little Chalfont, UK). A blocking buffer of 5% milk in 1×TBS-T (1×TBS +0.1% TWEEN® 20 (polysorbate 20)) was used to block non-specific binding by incubation for 1 h at room temperature. Primary antibodies against phospho-PD-1 (clone 407.6G12), anti-mouse PD-1 (clone 29F.1A12), anti-human PD-1 (clone 6G1) diluted in 1% BSA in TBS-T were incubated with the membrane overnight at 4° C. After washing three times with TBS-T, the membrane was incubated with horseradish peroxidase-conjugated goat anti-mouse or anti-rat IgG secondary antibody diluted in 2.5% milk in TBS-T buffer plus 1% normal goat serum 1h at room temperature. Immunoreactive proteins were detected using enhanced chemiluminescence (ECL) reagents (PekinElmer, Waltham, MA).

e. Generation of PD-L1 Tetramer mPD-L1 kappa/mPD-L1-hIgG1 fusion protein tetramer was generated by an in-fusion cloning method (Zhu et al. (2007) *Biotechniques* 43:354-359). The extracellular domain of mPD-L1 with a 17 amino acid linker (GGSGGTGGSGGTGGSGG) (SEQ ID NO: 141) was linked separately to human Kappa constant region or IgG1 CH1-hinge-CH2CH3 region in the pEFGF expression vector and expressed in CHO cells (Naito et al. (2013) *Cancer Immunol. Immunother.* 62:347-357). The Fc fusion protein was purified from CHO cell culture supernatants by protein G affinity chromatography and verified to have endotoxin levels less than 2 EU/mg protein.

f. PD-L1 Tetramer Stimulation and IL-2 ELISA Assay $1×10^5$ Jurkat hPD-1 cells/well were cultured in 96 well plates with the PD-L1 tetramer for 1 hour and then treated with anti-human CD3 antibody (0.1 µg/ml) and anti-human CD28 antibody (0.3 µg/ml) for 24 hours. Cell culture supernatants in 96-well plates were harvested and evaluated for IL-2 using the Duoset human IL-2 ELISA kit (R&D Systems, Minneapolis, MN) according to the manufacturer's protocol.

g. In Vitro T Cell Stimulation

CD8$^+$ T cells from the spleens of P14 TCR Tg mice were isolated using MACS® beads and columns (Miltenyi Biotec, Cambridge, MA). $5×10^4$ cells were plated on $1×10^5$ irradiated (3000 rads) splenocytes from TCRα$^{-/-}$ mice. 1 µg of GP33-41 (Genscript, Piscataway, NJ) was added and cells were incubated at 37° C. for 72 h prior to analysis.

h. Tumor Studies

Mice were injected in the flank subcutaneously with $1 \times 10^5$ MC38 tumor cells. Tumors were measured every 2-3 days (length×width) with a caliper. Tumor volume was determined using the formula: $1/2 \times D \times d^2$, where D is the major axis and d is the minor axis. Mice were sacrificed when tumors reached 2 $cm^3$ or upon ulceration. Where indicated, mice were given 200 μg anti-PD-1 antibody (clone 29F.1A12) i.p. at days 7, 10, and 13 after tumor implantation. Isotype control antibody (2A3) was purchased from BioXCell (West Lebanon, NH). Upon collection, tumors were dissected and mechanically disaggregated before digestion with collagenase type I (400 U/ml; Worthington Biochemical, Lakewood, NJ) for 30 minutes at 37° C. Following digestion, tumor cells were passed through 70 μm filters and mononuclear cells isolated by centrifugation through a Percoll gradient (40 and 70%), and analyzed by flow cytometry.

i. Flow Cytometric Analysis of T Cells

A BV421-conjugated version of the phospho-PD-1 antibody (clone 6G12) was prepared (Biolegend, San Diego, CA). Cells cultured in vitro (human and mouse) or isolated from the dLN or tumor of mice were stained with the following directly labeled antibodies to surface molecules (all from Biolegend): anti-hPD-1 (EH12), anti-mCD45.2 (104), anti-mCD3e (145-2c11), anti-mCD4 (RM4-5), anti-mCD8a (53-6.7), anti-mPD-1 (RMP1-30), and anti-mTIM-3 (RMT3-23). After staining, cells were fixed and permeabilized using an Intracellular Fixation Buffer (eBioscience #88-8824-00, Waltham, MA) and then stained with BV-421 conjugated anti-phospho-PD-1 (6G12; 10 μg/ml). Isotype or Fluorescence Minus One controls were used for gating. Samples were analyzed on an LSR II or a FACSCanto™ II HTS (BD Biosciences, San Jose, CA) and with FlowJo® software (Tree Star, Ashland, OR).

j. Statistics

All statistical analysis was performed with Prism software (GraphPad, La Jolla, CA) and statistical significance determined where the p-value was less than 0.05 (*).

Example 2: Monitoring PD-1 Signaling in Tumor Infiltrating Lymphocytes

Figure 6:
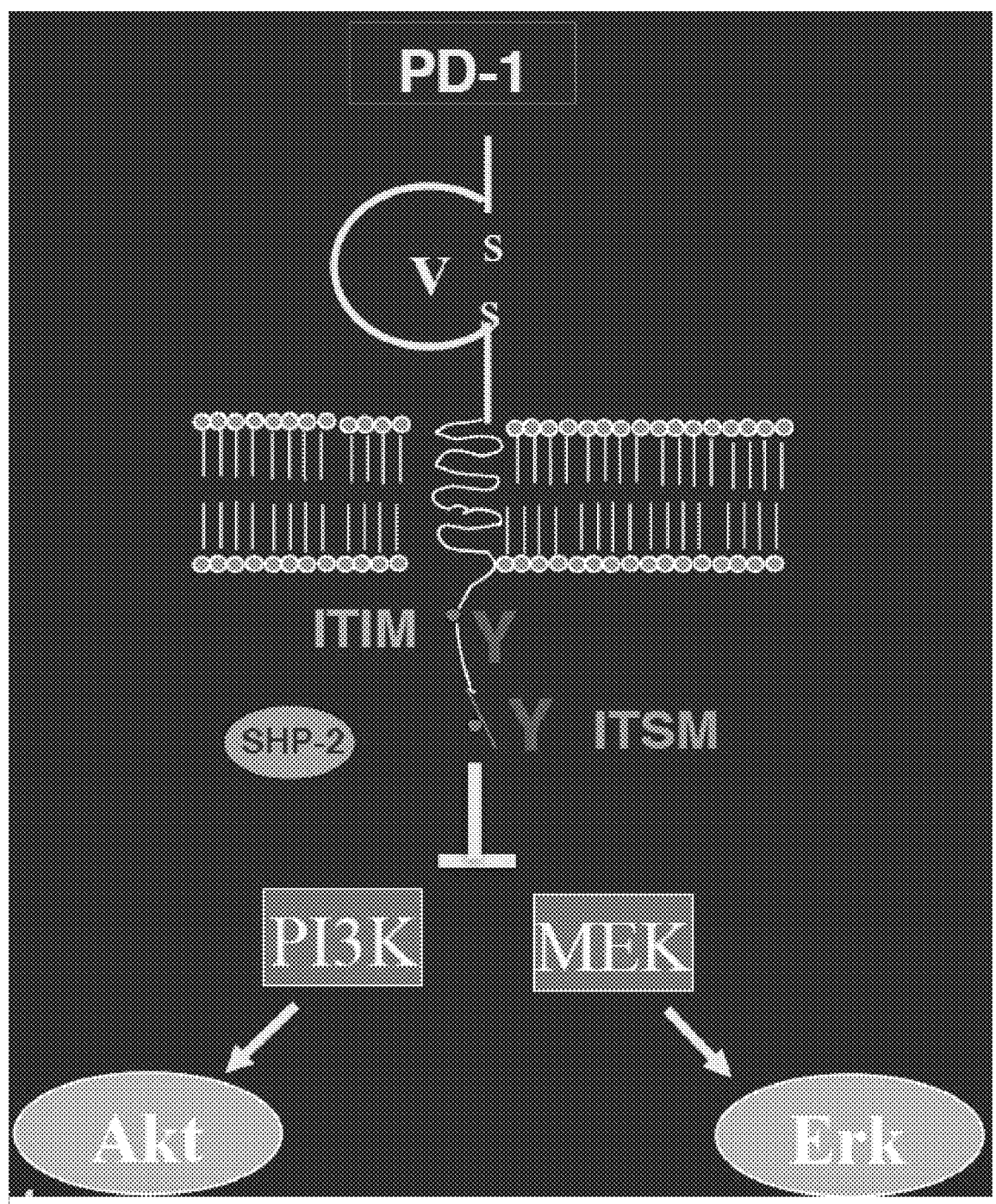
FIG. 6 depicts PD-1 signaling pathways.

Programmed death (PD)-1 pathway blockade is a successful strategy for cancer immunotherapy. However, only a limited number of patients respond. There is great need to identify predictors of therapeutic response and to monitor response to PD-1 immunotherapy. PD-1 is an inhibitory receptor expressed on activated T-cells. SHP-2 tyrosine phosphatase interacts with PD-1 and is critical for PD-1-mediated inhibition. The cytoplasmic tail of PD-1 contains an immunoreceptor tyrosine-based inhibitory motif (ITIM) and an immunoreceptor tyrosine-based switch motif (ITSM). It has been reported that SHP-2 may interact with either ITIM or ITSM of PD-1. Such interaction mediates inhibition of PI3K/Akt and MEKK/Erk pathways (FIG. 6). PD-1, a 288-amino acid protein, has a single extracellular IgV-like domain and 94-amino acid intracellular tail containing both an immunoreceptor tyrosine-based inhibitory motif (ITIM) and an immunoreceptor tyrosine-based switch motif (ITSM) (Riley et al. (2009) *Immunol. Rev.* 229:114-125). Mutation of the ITIM has little effect on PD-1 function. However, mutation of the tyrosine 248 of the ITSM domain (Y248) renders PD-1 non-functional in vitro, demonstrating that this residue is critical for PD-1 signaling (Chemnitz et al. (2004) *J. Immunol.* 173:945-954). Phosphorylation of Y248 leads to recruitment of SHP2 to the immunologic synapse, resulting in dephosphorylation of signaling molecules downstream of the T-cell receptor (TCR) (Keir et al. (2007) *Curr. Opin. Immunol.* 19:309-314). For reviews and reports, see Chemnitz et al. (2004) *J. Immunol.* 173:945-954; Patsoukis et al. (2012) *Sci. Signal.* 5:ra46; Patsoukis et al. (2012) *Mol Cell Biol* 33:3091-3098; and Patsoukis et al. (2015) *Nature com.* 26:6692.

One challenge is that PD-1 expression can mark activated T cells, which are susceptible to PD-1-mediated inhibition, but does not indicate whether a PD-1-mediated immunoinhibitory signal is being delivered. Currently there are no methods to detect active PD-1 signaling and, in turn, successful PD-1 inhibition. This Example describes the development of an exemplary antibody that recognizes active PD-1 signaling both in vitro and ex vivo, and detects the signaling of PD-1 phosphorylation in tumor infiltrating lymphocytes. Specifically, the exemplary antibody recognizes the phosphorylation of the immunotyrosine switch motif (ITSM) in the intracellular tail of both human and mouse PD-1 (phospho-PD-1). This establishes a tool for studying active PD-1 signaling and successful PD-1 blockade. Because PD-1 is rapidly upregulated on T cells within hours of their activation, PD-1 expression may indicate either an activated, functional T cell (no PD-1 ligation) or a suppressed T cell (PD-1 ligation). Detection of PD-1 phosphorylation can be used to predict the success of PD-1 immunotherapy because PD-1 phosphorylation would decrease upon blockade of PD-1 ligation. Anti-phospho PD-1 antibody may also block PD-1-mediated signaling. Using this anti-phospho-PD-1 mAb, it is shown that PD-1±tumor infiltrating lymphocytes (TILs) expression multiple co-inhibitory receptors, such as those in MC38 murine colorectal tumors, have high levels of phosphorylated PD-1 (Blackburn et al. (2009) *Nat. Immunol.* 10:29-37; Sakuishi et al. (2010) *J. Exp. Med.* 207:2187-2194), particularly in PD-1$^+$ TIM-3±TILs. Upon PD-1 blockade, PD-1 phosphorylation was potently decreased in TIM-3$^+$ CD8$^+$ TILs prior to tumor clearance. These data demonstrate that phosphor-PD-1 mAb can detect decreases in PD-1 signaling after antibody blockage and that phosphorylation of the ITSM of PD-1 marks dysfunctional T cells that may be rescued with PD-1 blockade. Analysis of phospho-PD-1 in TILs thus serves as a biomarker for responsiveness/efficacy of PD-1 immunotherapy.

a. Validation of a Monoclonal Antibody (mAb) that Detects Phosphorylation of the ITSM Domain of Human and Mouse PD-1

PD-1 is expressed on the surface of T cells upon activation, but inhibitory signals are not transmitted into the cells unless PD-1 is ligated by PD-L1 or PD-L2 (Chemnitz et al. (2004) *J. Immunol.* 173:945-954). Therefore, it is challenging to study PD-1 function and manipulation (e.g., through therapeutic blocking antibodies) due to the inability to distinguish PD-1$^+$ cells receiving a signal from those that are not receiving a signal. Herein a tool was developed to specifically detect PD-1 signaling. The tyrosine 248 (Y248) of the immunoreceptor tyrosine-based switch motif (ITSM) of the PD-1 intracellular tail is critical for PD-1 signaling (Chemnitz et al. (2004), supra). In the present invention, mice were immunized with a phosphorylated peptide immunogen, which encompasses the ITSM and phosphorylated Y248 residue and includes an eight amino acid sequence identical in mouse and human PD-1 (FIG. 1A).

Figure 1B:
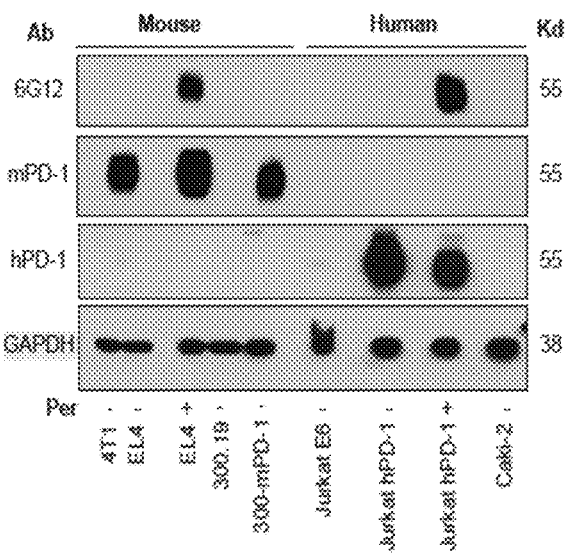

Antibodies were screened for reactivity with phospho-peptide and lack of reactivity with unphosphorylated peptide or carrier. Protein extracts from human and mouse T cells treated with the protein tyrosine phosphatase inhibitor, pervanadate, were analyzed to test antibodies developed through this approach. One antibody clone (307.6G12) detected a band only in pervanadate-treated samples that corresponds in size to PD-1. PD-1 total protein expression was confirmed in all relevant samples (FIG. 1B). These results indicate that the 6G12 antibody clone detects phosphorylated PD-1.

Figure 1C:
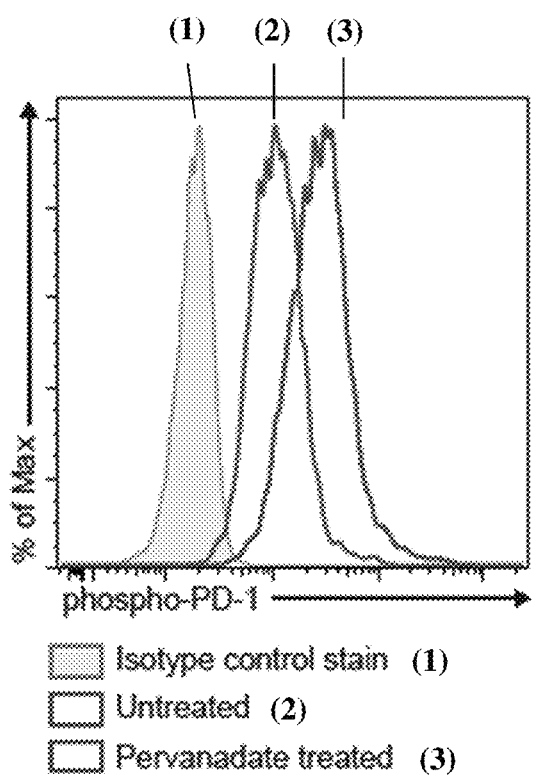
Figure 1D:
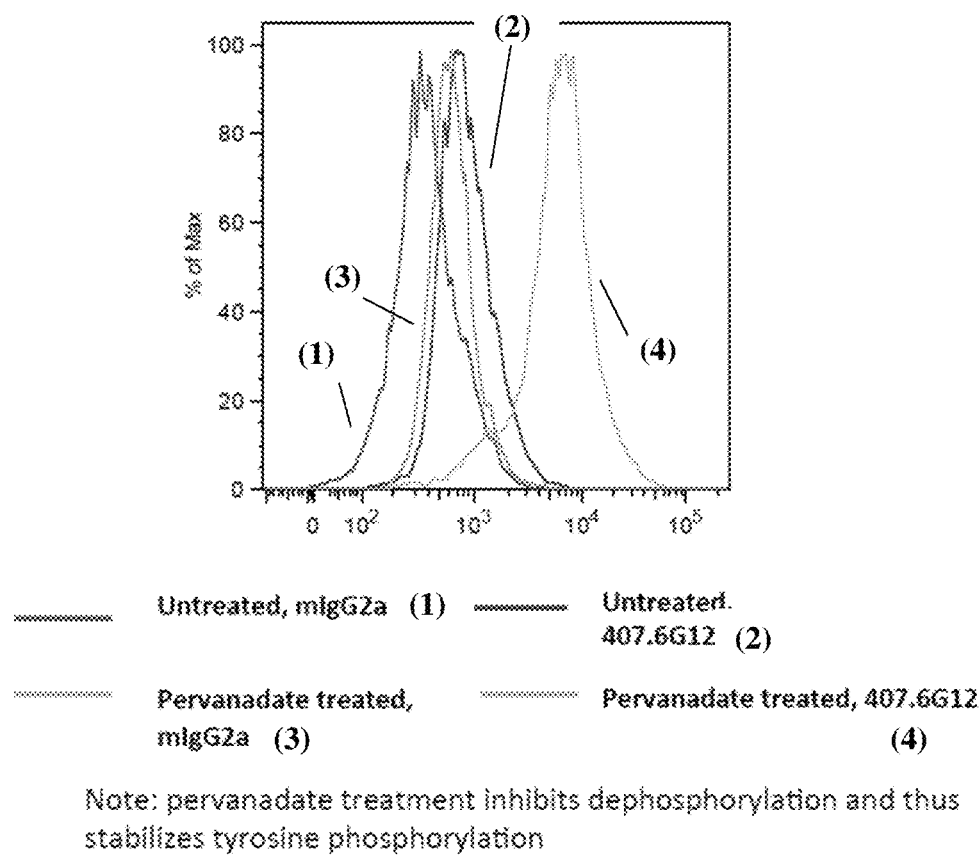
Figure 2A:
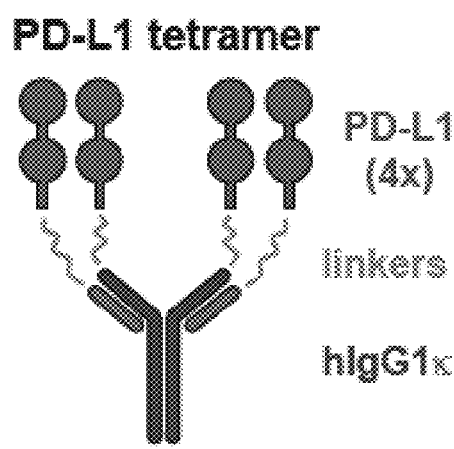
FIGS. 2A-2F show the detection of PD-1 ligation in vitro. A schematic of mPD-L1-Kappa/mPD-L1-hIgG1 fusion protein (PD-L1 tetramer) is illustrated in FIG. 2A. Surface expression of hPD-1 in Jurkat hPD-1 cells without stimulation is shown in FIG. 2B. IL-2 secretion following culture of Jurkat-hPD-1 cells with PD-L1 tetramer or hIgG control antibody concurrently with stimulation by anti-CD3 and anti-CD28 is shown in FIG. 2C. Phospho-PD-1 expression in Jurkat-hPD-1 cells treated with PD-L1 tetramer or hIgG control for 24 hours after stimulation with anti-CD3 and anti-CD28 is depicted in FIG. 2D. A time course analysis of phospho-PD-1 expression in Jurkat-hPD-1 cells cultured with PD-L1 tetramer or hIgG control after 24 hour stimulation with anti-CD3 and anti-CD28 is shown in FIG. 2E. Phospho-PD-1 signal in P14 TCR Tg T cells cultured with splenocytes and gp33 peptide is shown in FIG. 2F. All data shown are representative of at least 2 independent experiments.
Figure 2B:
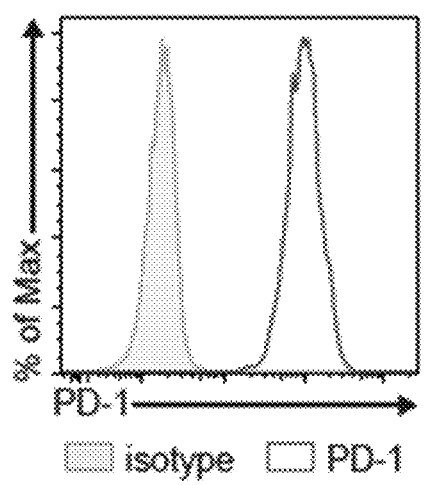
Figure 2C:
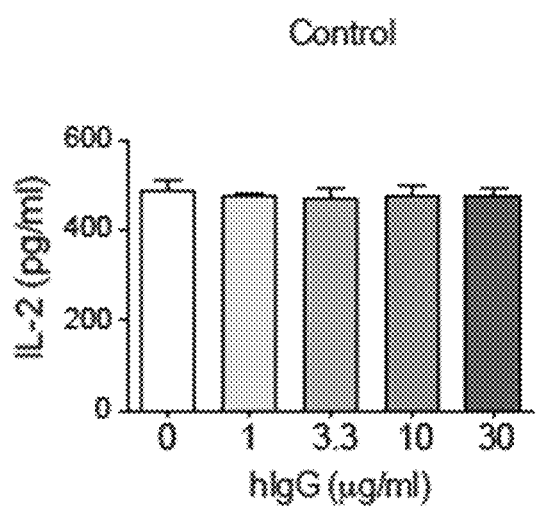
Figure 2C:
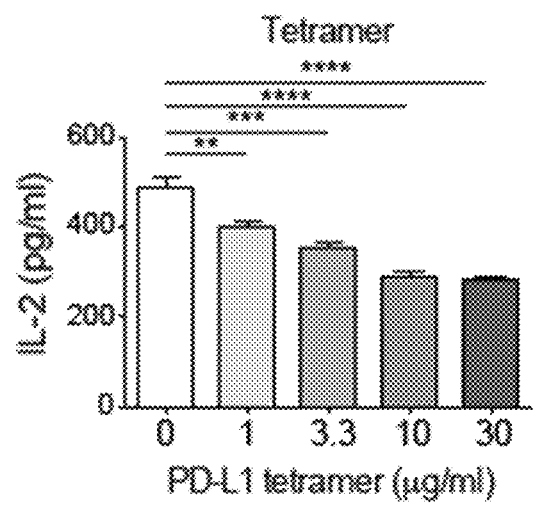

This antibody was tested for its ability to detect phosphorylation of PD-1 by flow cytometry. First, Jurkat cells, an immortalized human T cell line, were transfected with human PD-1 (Jurkat-hPD-1). Relative to the isotype control, phospho-PD-1 were detected in untreated Jurkat-hPD-1 cells, increased with pervanadate treatment (FIG. 1C). Therefore, the clone 6G12 (hereafter referred to as "phospho-PD-1" antibody) can detect the phosphorylated form of the PD-1 ITSM by both western blot and flow cytometry.

b. Ligation of PD-1 by a PD-L1 Tetramer Triggers PD-1 Phosphorylation and Decreases T Cell Function It was next tested whether the phospho-PD-1 antibody could detect PD-1 ITSM phosphorylation following PD-1 ligation by PD-L1. Current soluble recombinant reagents for ligating PD-1 have limited strength of signal. To overcome this limitation, a tetramer was developed, in which a molecule of PD-L1 was linked to each of the IgG1 heavy and kappa chains, resulting in 4 molecules of PD-L1 on an antibody structure (FIG. 2A; referred to as PD-L1 tetramer). Without limitation, this approach would allow stronger ligation and cross-linking of PD-1. The Jurkat-hPD-1 cell line, which expresses high levels of hPD-1 on the surface, were utilized for confirmation (FIG. 2B). Specifically, Jurkat-hPD-1 cells were stimulated for 24 hours with anti-CD3/CD28 and PD-L1 tetramer or control antibody. Because IL-2 production is quickly downregulated upon PD-1 ligation (Chemnitz et al. (2004), supra; Latchman et al. (2001) *Nat. Immunol.* 2:261-268), the IL-2 levels in culture supernatants were measured (FIG. 2C). The PD-L1 tetramer potently suppressed IL-2 production across a range of tetramer concentrations. Maximal inhibition of IL-2 was reached by 10 µg/ml, which was chosen as the concentration for subsequent studies (FIG. 2C).

Figure 2D:
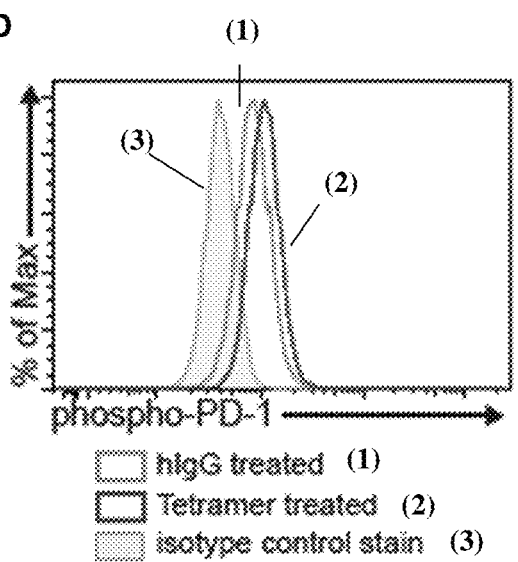
Figure 2E:
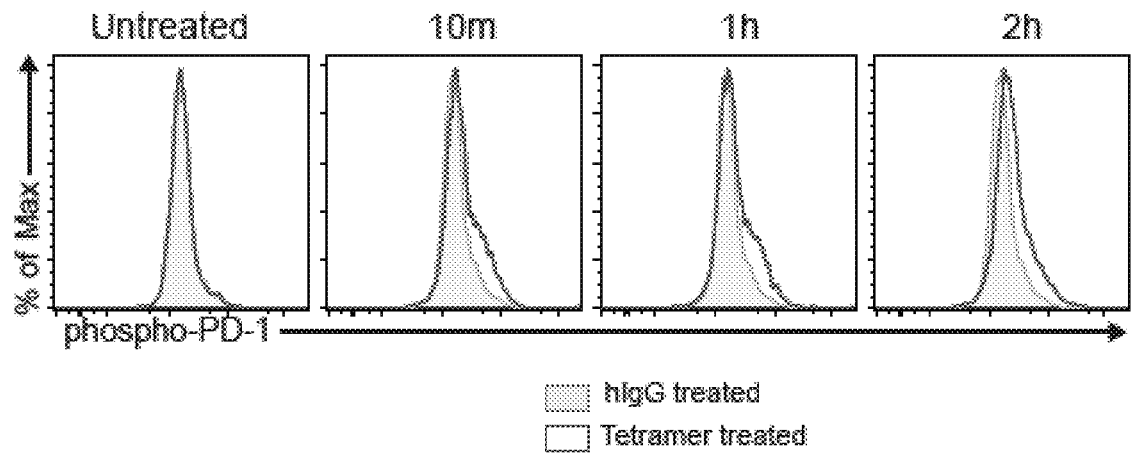

The PD-L1 tetramer were used to ligate PD-1 on Jurkat-hPD-1 cells and tested for the ability of the phospho-PD-1 antibody to detect PD-1 phosphorylation. Treatment with the PD-L1 tetramer led to an increase in the signal of phospho-PD-1 compared to levels of phospho-PD-1 in Jurkat-hPD-1 cells at baseline (FIG. 2D). This natural phospho-PD-1 signal (i.e., no pervanadate) was detectable by flow cytometry within 10 minutes and seen at 1 hour in a fraction of the cells and in all cells at 2 hours after PD-1 ligation by PD-L1 tetramer (FIG. 2E). Together, the results indicate that the phospho-PD-1 antibody can be used to detect active PD-1 signaling induced by PD-L1 ligation, and is a valuable tool in the development of agonists of the PD-1 pathway, which could be used to induce immune tolerance.

Figure 2F:
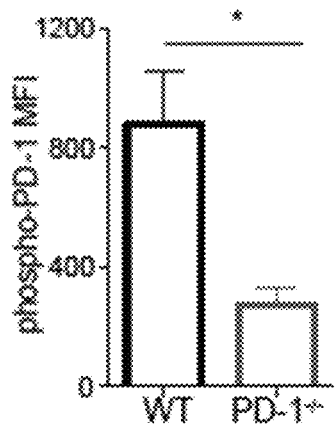

It was next tested whether the phospho-PD-1 antibody could detect a phospho-PD-1 signal in primary mouse T cells. Wild-type (WT) cells were compared to the control PD-1$^{-/-}$ CD8$^+$ T cells from P14 TCR transgenic mice, in which all T cells have a TCR that recognizes the gp33 peptide on H-2Kb. P14 TCR transgenic T cells were cultured with gp33 peptide and splenocytes from mice lacking αβT cells (TCRα$^{-/-}$) and assessed for phospho-PD-1 levels after 72 hours. All WT T cells expressed cell surface PD-1 by this time point and had significantly higher levels of phospho-PD-1 staining than the background staining levels detected in PD-1$^{-/-}$ T cells (FIG. 2F). Thus, this antibody detects PD-1 signaling in primary T cells delivered by PD-1 ligands on APCs.

c. Detection of PD-1 Signaling in Tumor-Infiltrating Lymphocytes

Figure 3A:
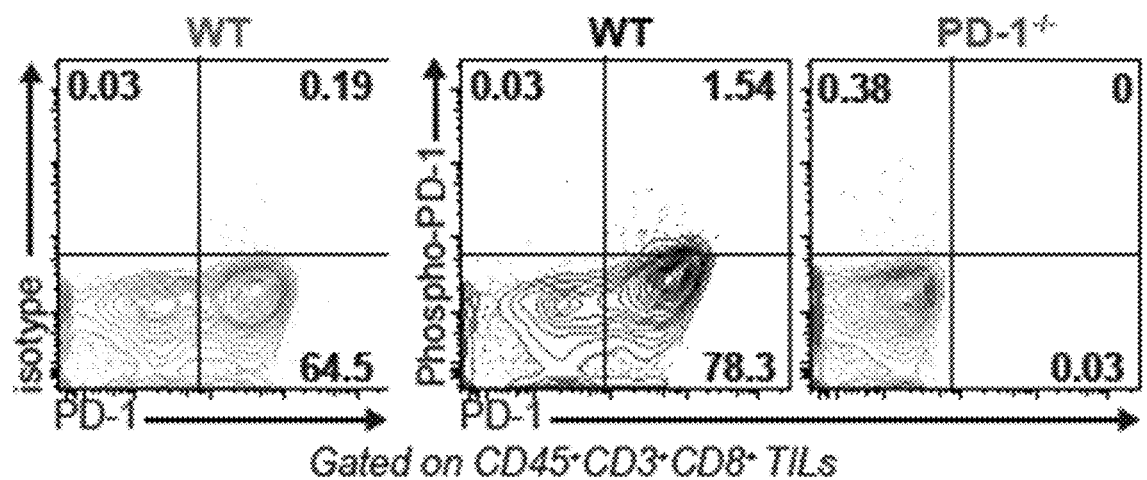
FIGS. 3A-3D show the detection of active PD-1 signaling in T cells from tumor-bearing mice. $1 \times 10^5$ MC38 tumor cells were implanted s.c. into mice on day 0 Immune cells were isolated from tumors and dLN at the indicated timepoints.
Figure 3B:
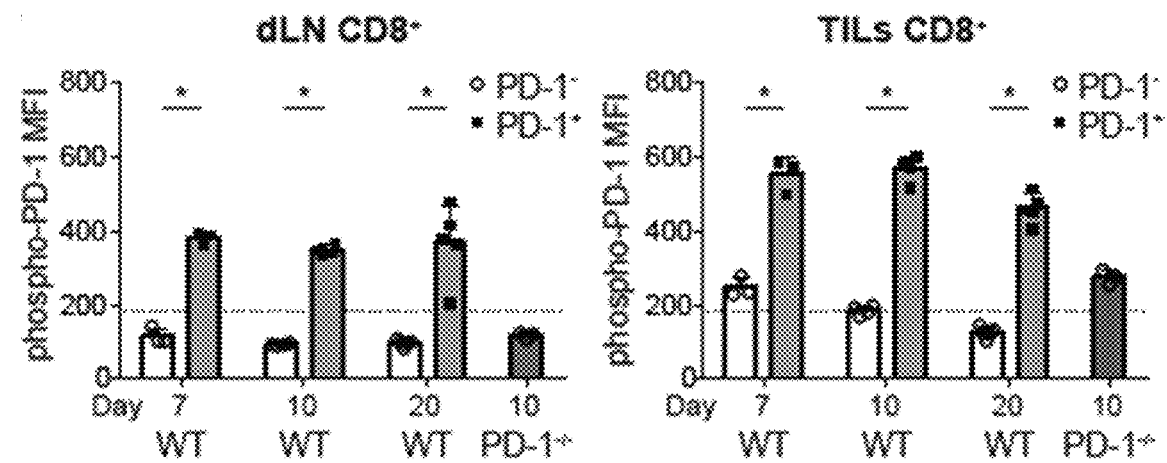

The phospho-PD-1 antibody was tested for whether it could detect PD-1 signals in an in vivo setting and for its specificity by the absence of a signal in PD-1-deficient T cells. The MC38 colorectal adenocarcinoma tumor model was chosen for these studies because TILs in this model express high levels of PD-1 and are suppressed directly by PD-L1 on MC38 tumors cells. Mice deficient for PD-1 clear either a fraction or all MC38 tumors, depending on the dose of cells given (Woo et al. (2012) *Cancer Res.* 72:917-927). Therefore, WT and PD-1$^{-/-}$ mice were implanted with 1×10$^5$ MC38 tumor cells, a dose at which the majority of PD-1$^{-/-}$ mice clear the tumor (data not shown). At day 10 of tumor growth, near the maximum tumor size in PD-1$^{-/-}$ mice prior to tumor clearance, lymphocytes were isolated from the draining lymph node (dLN) and tumors, and analyzed expression of phospho-PD-1. T cells expressing PD-1 had detectable levels of phospho-PD-1 while PD-1-deficient T cells had no detectable phospho-PD-1 (FIGS. 3A-3B). The phospho-PD-1 signal was strongest in CD8$^+$ PD-1$^+$ TILs and also detected in CD8$^+$PD-1$^+$ T cells from the dLN (FIG. 3B). This phospho-PD-1 expression is not due to the larger size of activated cells, as this pattern is not seen with the isotype control antibody (FIGS. 3A-3B; dotted line). The specificity of the phospho-PD-1 antibody staining was confirmed by the absence of phospho-PD-1 expression in PD-1$^{-/-}$ T cells.

Figure 3C:
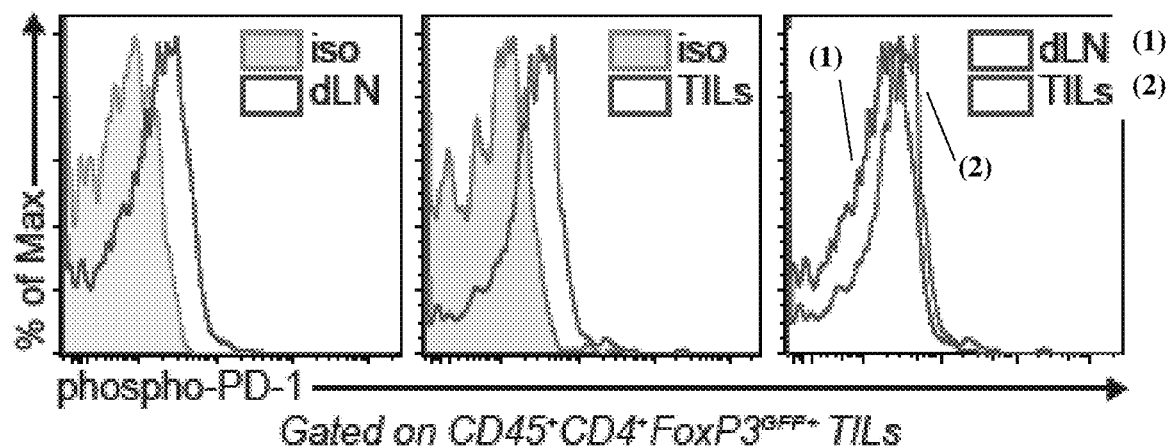
Figure 3D:
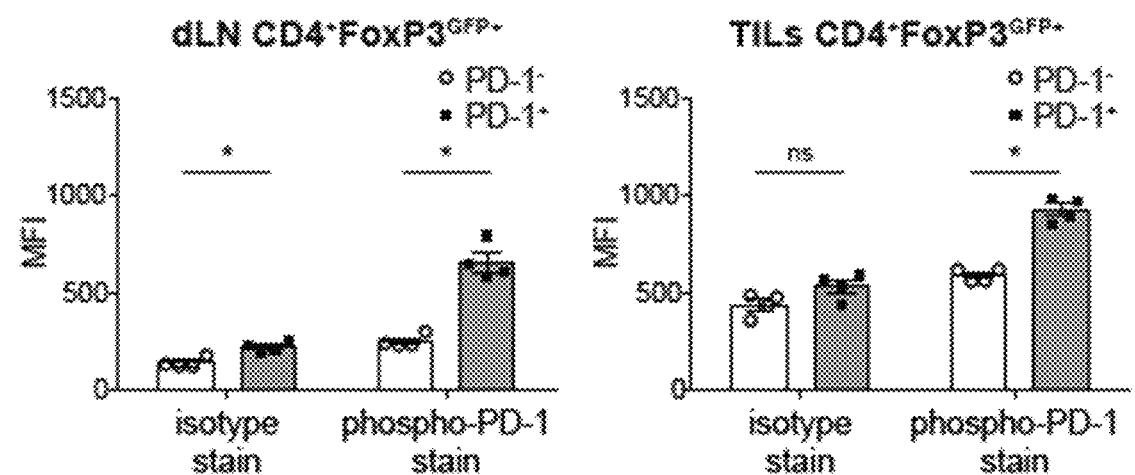

The levels of phospho-PD-1 signaling in Tregs in the dLN and tumor were assessed at day 10 of MC38 tumor growth (FIGS. 3C-3D). Of note, methods to permeabilize the nucleus to detect FoxP3 expression were incompatible with staining for phospho-PD-1, so FoxP3 could not be stained directly. Therefore, GFP expression in transgenic FoxP3$^{GFP}$ mice was used to identify Tregs. Similar to CD8$^+$ TILs, PD-1$^+$ Tregs from both the dLN and tumor had a detectable phospho-PD-1 signal, while PD-1$^-$ Tregs did not express phospho-PD-1 (FIGS. 3C-3D). Therefore, the phospho-PD-1 antibody can be used to specifically assess PD-1 signaling in different intratumoral T cell subsets.

d. PD-1 Blockade Decreases Phosphorylation of PD-1 Most Potently in CD8$^+$ TILs that Co-Express TIM-3

Figure 4A:
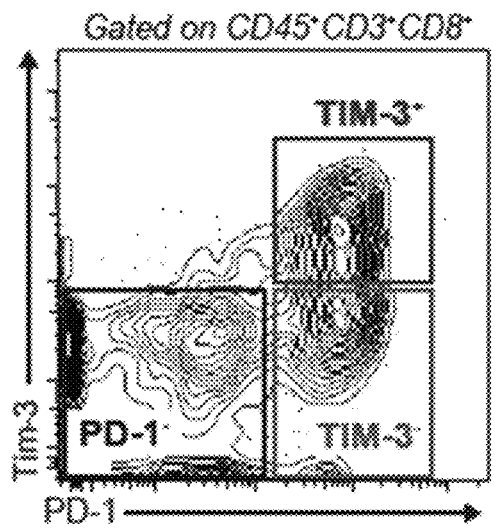
FIGS. 4A-4F show that PD-1 signaling is reduced in PD-1$^+$TIM-3$^+$ T cells from tumor-bearing mice after PD-1 blockade. $1 \times 10^5$ MC38 tumor cells were implanted s.c. into mice on day 0. Immune cells were isolated from tumors and dLN.
Figure 4B:
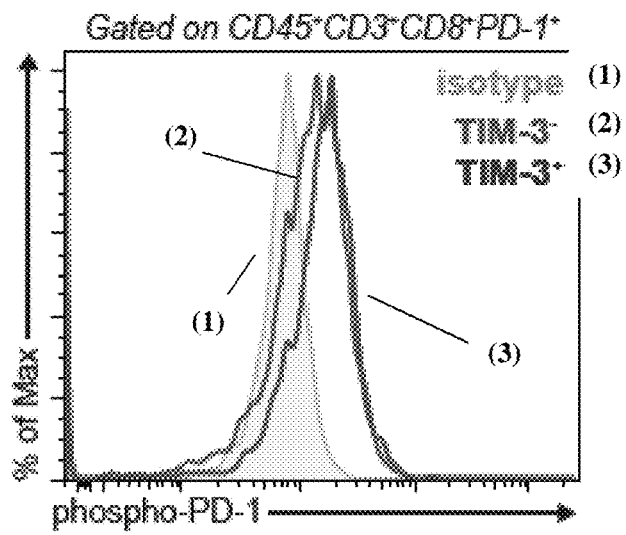
Figure 4C:
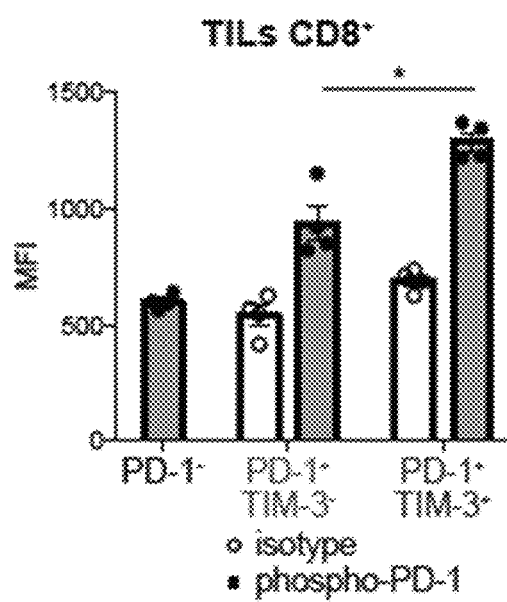
Figure 4D:
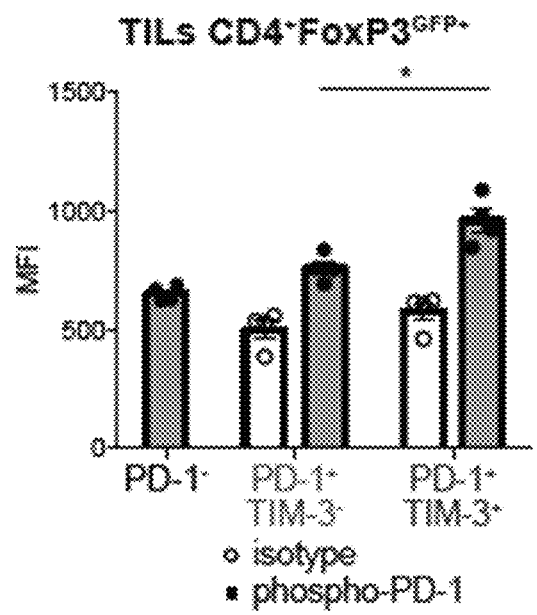

It was hypothesized that not all PD-1$^+$ TILs have equivalent levels of phospho-PD-1 signaling. T cells that express multiple co-inhibitory molecules are more dysfunctional than T cells that express one or none (Blackburn et al. (2009) *Nat. Immunol.* 10:29-37). For example, TILs that co-express PD-1 and TIM-3 produce fewer cytokines than T cells that only express PD-1 (Sakuishi et al. (2010) *J. Exp. Med.* 207:2187-2194). This could be due, in part, to enhanced PD-1 signaling pathway in TIM-3$^+$ cells. To test this hypothesis, TILs were isolated from MC38 late during tumor growth (day 20) and compared for phospho-PD-1 levels in T cells that express TIM-3, PD-1, or both (FIGS. 4A-4B). Phosphorylated PD-1 was detected in CD8$^+$ TILs that express PD-1 regardless of TIM-3 expression. However, there was significantly higher MFI of phospho-PD-1 in PD-1$^+$ TIM-3±TILs when compared to PD-1$^+$ TIM-3$^-$ TILs (FIGS. 4A-4C). Similarly, PD-1$^+$ TIM-3±Treg cells expressed higher levels of phospho-PD-1 (FIG. 4D). Together, these data indicate that T cells that are more dysfunctional experience higher levels of PD-1 signaling.

Figure 4E:
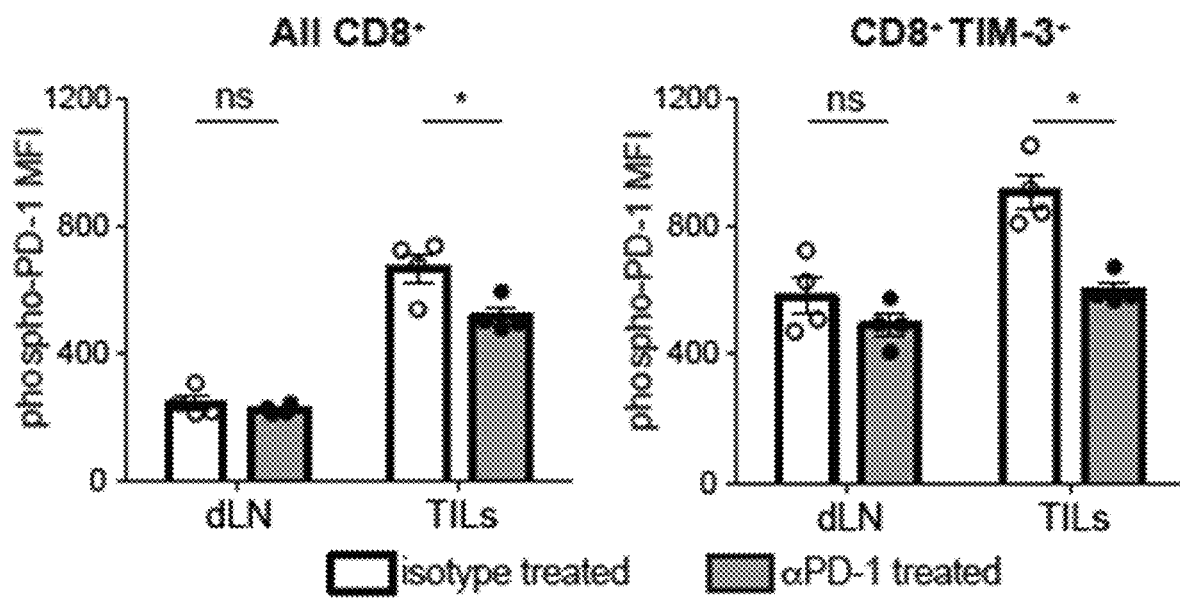
Figure 4F:
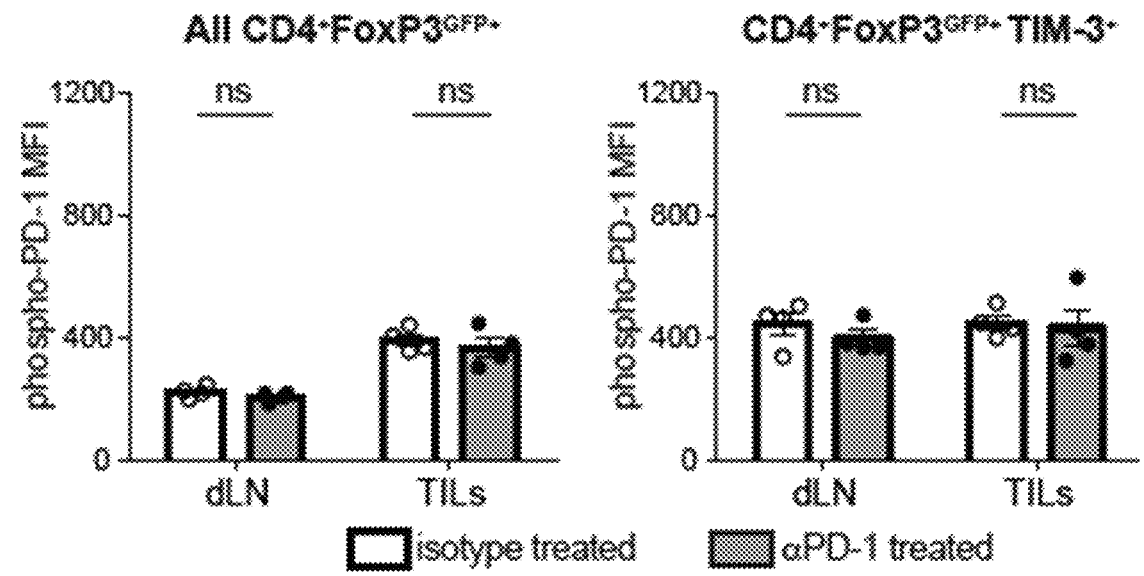

Because MC38 tumors are highly responsive to PD-1 blockade (Woo et al. (2012) *Cancer Res.* 72:917-927), it was hypothesized that TILs from MC38 tumors would have diminished phospho-PD-1 signaling after PD-1 blockade. Since untreated PD-1$^+$ TIM-3$^+$ TILs had higher levels of phospho-PD-1, compared to PD-1$^+$ TIM-3$^-$ TILs, it was believed that PD-1 blockade would reduce phospho-PD-1 levels to a greater extent in the PD-1$^+$TIM-TILs, and this could be used as a biomarker for effective PD-1 antibody blockade. To test these hypotheses, anti-PD-1 blocking mAbs were administered to MC38 tumor-bearing mice, and T cells and dLN were isolated from the tumor on day 14, one day after the third treatment, for evaluating phospho-PD-1 expression. Following PD-1 antibody treatment, there was a decrease in overall phospho-PD-1 signal in CD8$^+$ T cells in the tumor, but no difference in the dLN (FIG. 4E). This decrease was much more striking in TIM-3$^+$ TILs (FIG. 4E). In contrast, phospho-PD-1 levels were not reduced in bulk Tregs or TIM-3$^+$ Tregs after PD-1 blockade (FIG. 4F). These data indicate that PD-1 blockade may work primarily through reduction of PD-1 signaling in CD8+ T cells rather than on Tregs in tumors.

Together, these data indicate that phosphorylation of the PD-1 ITSM motif in the intracellular tail can be used as a metric for active PD-1 signaling. TILs that co-express multiple co-inhibitory molecules have higher levels of phospho-PD-1 than cells that express one or none, and anti-PD-1 therapy diminishes this PD-1 signaling. Thus, this phospho-PD-1 antibody is a valuable tool for studying PD-1 biology. It was also shown that phospho-PD-1 in CD8$^+$ TILs is reduced with PD-1 blockade in a PD-1 sensitive tumor model.

e. PD-1 Blockade Decreases Phosphorylation of PD-1 in Human Peripheral Blood Mononuclear Cells (PBMCs)

The function of anti-phospho-PD-1 antibodies were further tested in human PBMCs. Specifically, human PBMCs were harvested from healthy donor using the Ficoll density gradient centrifugation method previously described in Fuss et al. (2009) *Curr. Protoc. Immunol.* Chapter 7:Unit7.1. doi: 10.1002/0471142735.im0701s85 or, alternatively, the protocol on the website of Miltenyi Biotec, San Diego, CA). A Pan T Cell Isolation Kit (Miltenyi Biotec, Cat. #130-096-535) was used to isolate CD3+ cells. The isolated CD3+ cells were cultured with or without CD3 (0.1 µg/ml)/CD28 (0.3 µg/ml) stimulation for 24 hours. Then, cells were treated with or without the PD-L1 tetramer (30 µg/ml) for 24 hours, prior to harvest and staining with the following panel: Live/Dead Yellow, CD3 BV 605, CD4 FITC, CD8 PE-Cy7, PD-1 PE, Phospho PD-1 BV421 (intracellular), PD-L1 APC, and CD80 BV786.

Figure 5A:
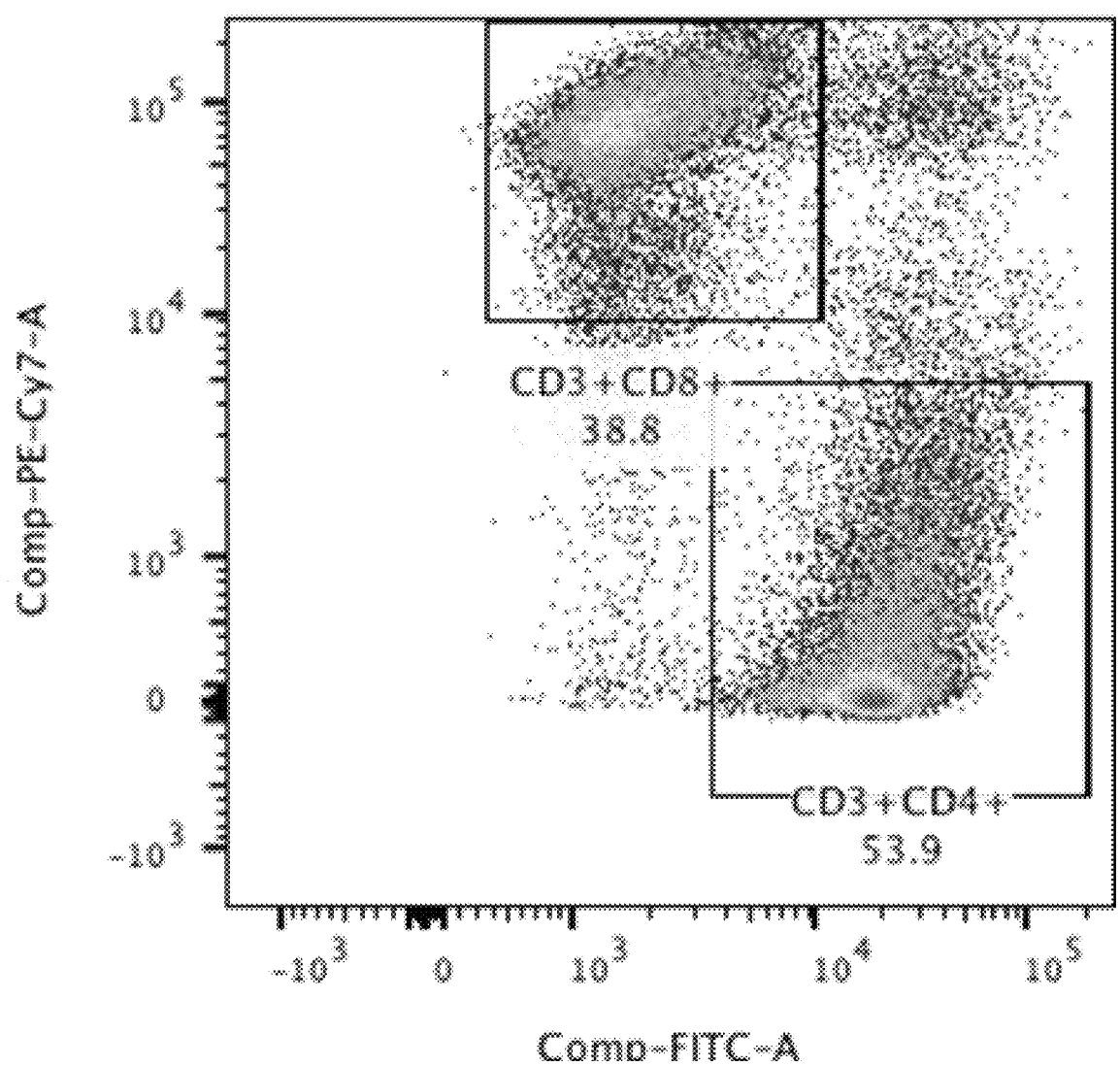
FIGS. 5A-5G show the phospho-PD-1 levels in CD3+ T cells with or without CD3/CD28 stimulation and with or without PD-L1 treatment.
Figure 5B:
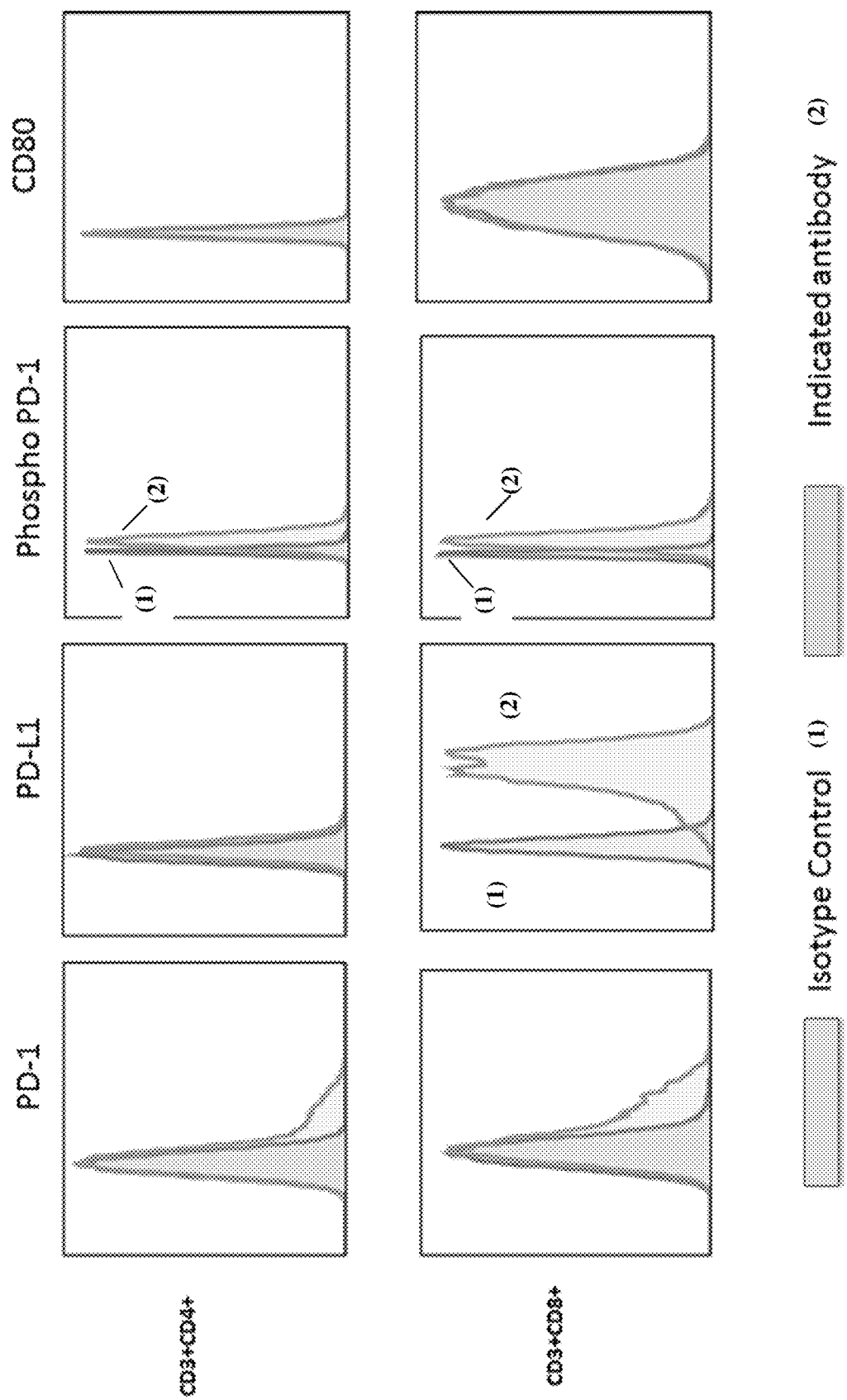
Figure 5C:
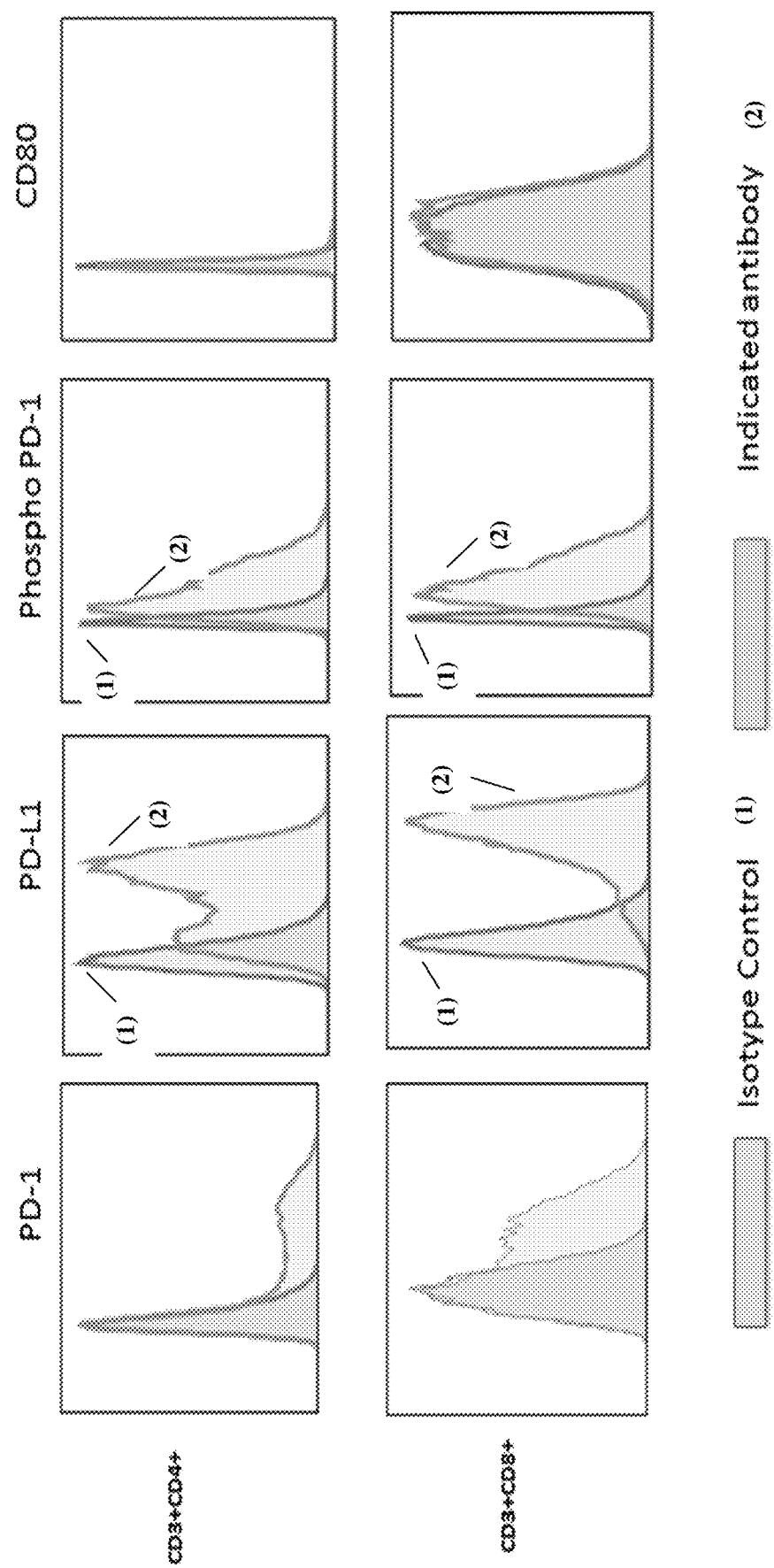
Figure 5D:
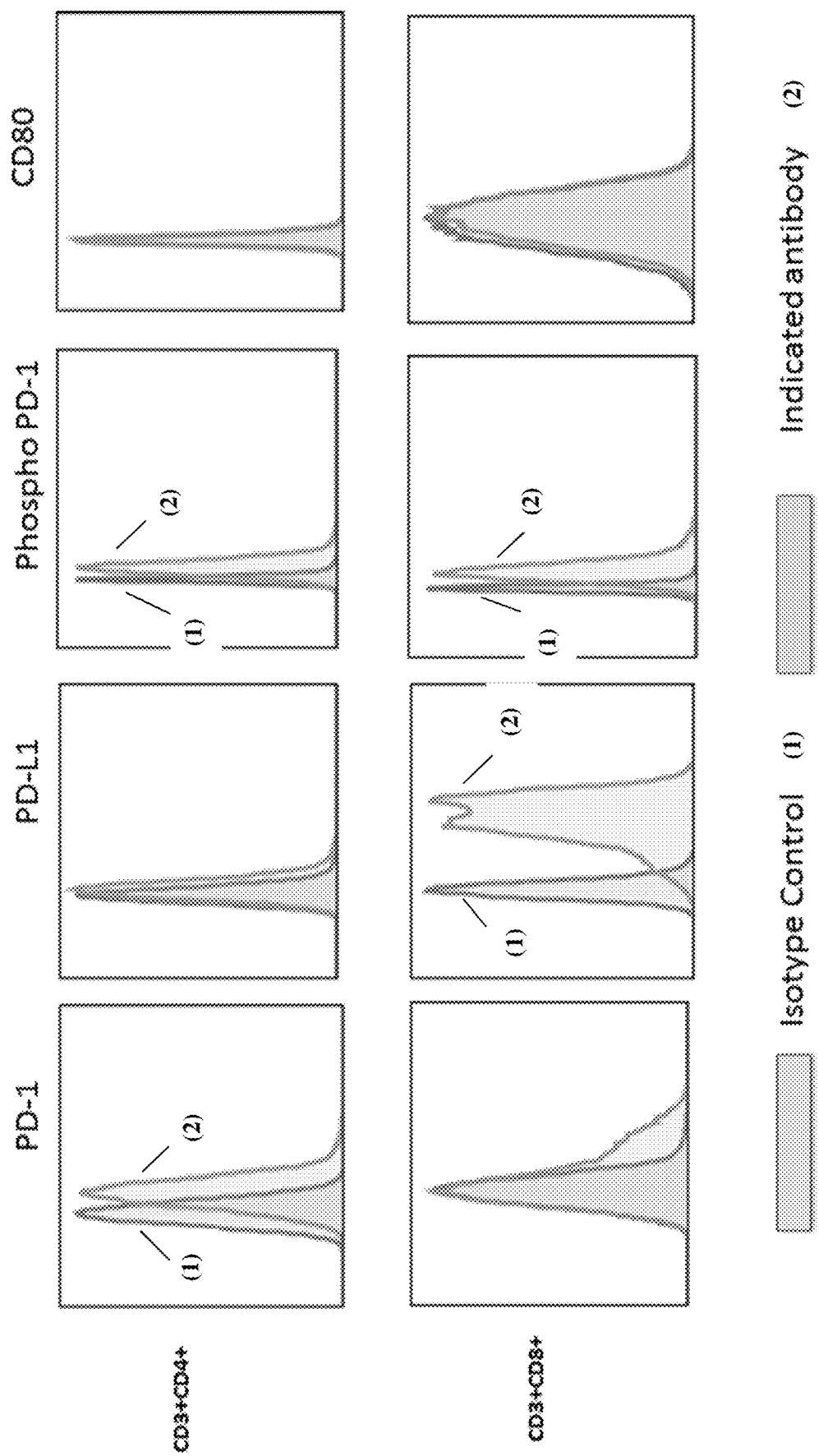
Figure 5E:
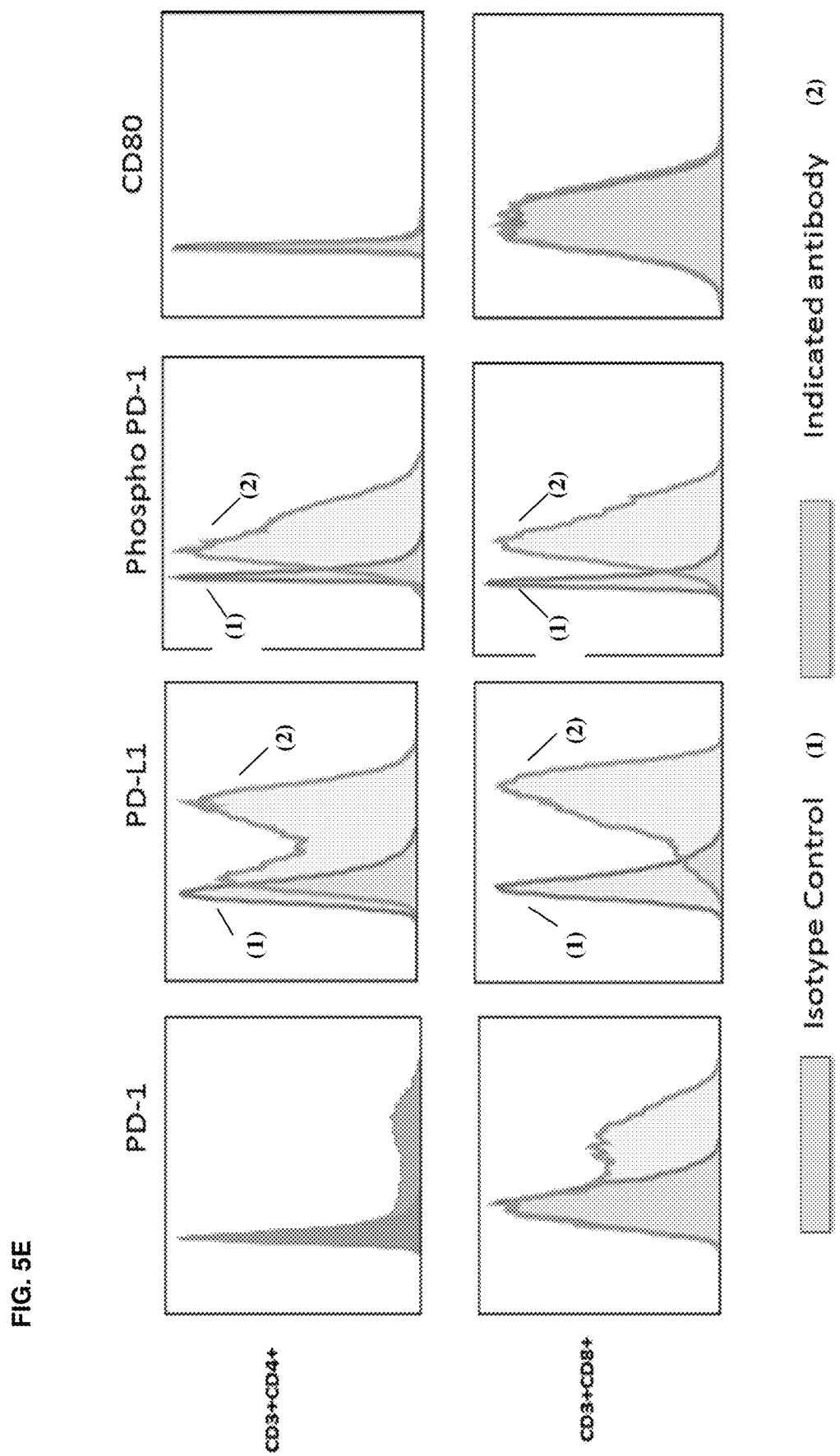
Figure 5F:
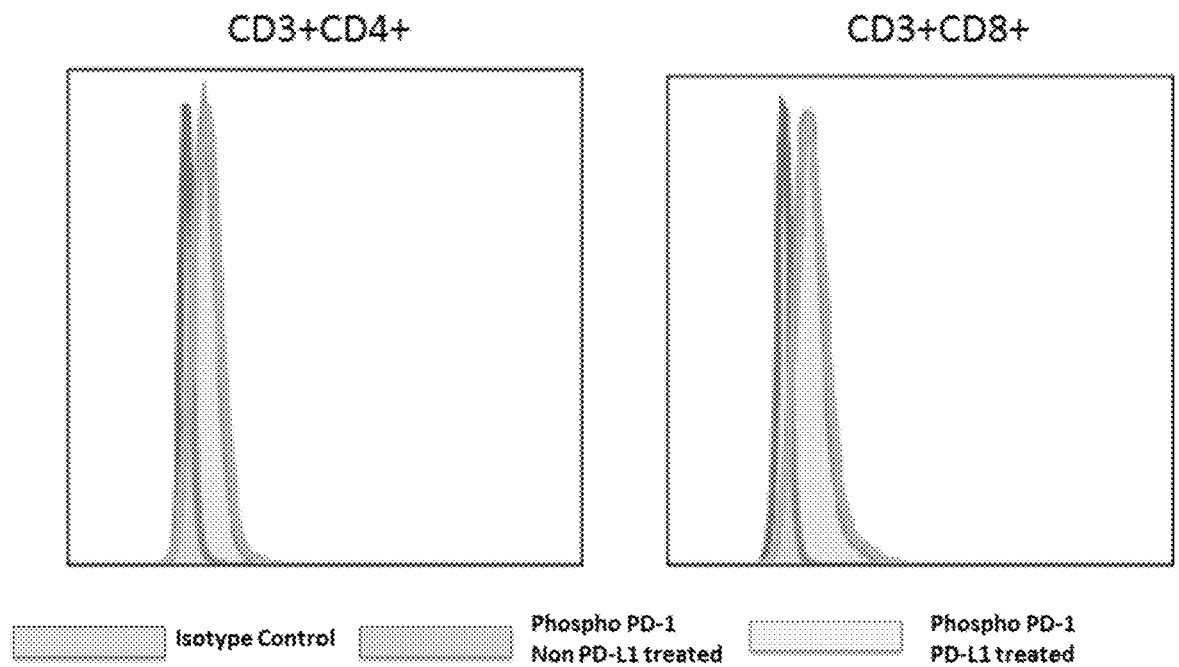
Figure 5G:
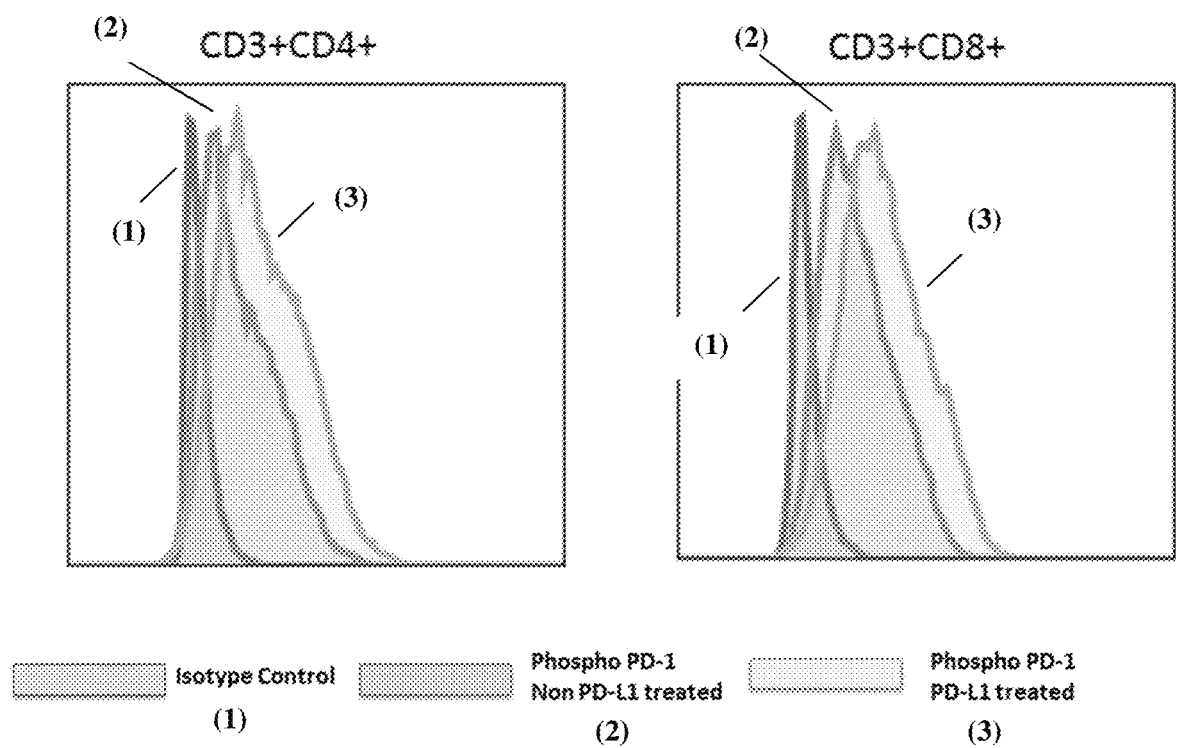

CD3+CD4+ and CD3+CD8+ cells were analyzed from human PBMC (FIG. 5A). As compared with non-stimulated cells, CD3/CD28 stimulation increased the expression of PD-1, PD-L1, and phospho-PD-1 (recognized by the 6G12 antibody), but not CD80, to different degrees in both types of cells (FIGS. 5B-5C). When unstimulated, CD3+CD8+ cells expressed significantly more PD-L1, but not PD-1, phospho-PD-1, or CD80, as compared to CD3+CD4+ cells (FIG. 5B). This difference in PD-L1 was attenuated after stimulation, and after stimulation, both CD3+CD8+ and CD3+CD4+ T cells expressed PD-L1 (FIG. 5C). In addition, more phospho-PD-1 expression was detected in CD3+CD8+ cells than CD3+CD4+ cells after CD3/CD28 stimulation (FIG. 5C). PD-L1 treatment increased PD-1 and phospho-PD-1 expression in stimulated CD3+ cells (FIG. 5E) as compared to unstimulated cells (FIG. 5D). In addition, the increase of phospho-PD-1 expression upon PD-L1 treatment was more significant in CD3+CD8+ cells than CD3+CD4+ cells (FIG. 5E). In summary, for unstimulated CD3+ cells, PD-L1 treatment did not significantly increase phospho-PD-1 expression, presumably because little PD-1 is expressed (FIG. 5F). By contrast, PD-L1 treatment significantly increased PD-1 expression and phospho-PD-1 expression in CD3+ cells after CD3/CD28 stimulation (FIG. 5G). Such increase was more significant in CD3+CD8+ cells than in CD3+CD4+ cells (FIG. 5G).

Taken together, these results indicate that PD-1 pathway activation can be measured using anti-phosphotyrosine PD-1 antibodies. Such antibodies allow the examination of PD-1 signaling, such as by assaying PD-1 phosphorylation in T cells from cancer patients or in mice with tumors before immunotherapy and at various points after PD-1, CTLA-4 or other immunotherapies, in order to measure the relationship between the level of PD-1 signaling and response to immunotherapy. Such peripheral blood T cells and other white blood cells can be phenotyped for lineage markers and markers of activation, including the marker, BIM. These results also allow the development and validation of new panels of markers specifically designed to measure PD-1 signaling in cells of interest, such as human T cell subsets. For example, marker panels for conventional flow cytometry, as well as mass cytometry, are contemplated and can be used to examine peripheral blood lymphocytes (PBL) obtained from cancer patients to identify patients with high levels PD-1 activation in T cells and how PD-1 blockade or other immunotherapies reduce the level of PD-1 activation in vivo. These studies are believed to provide a reliable dynamic biomarker to predict clinical response to PD-1 blockade and to monitor response to PD-1 blockade. It is further believed that T cells expressing the highest levels of phospho-PD-1 are most likely to respond to PD-1 blockade and monitoring levels of phospho-PD-1 in T cells after anti-PD-1 treatment will reflect the extent to which PD-1 blockade is effective in vivo. Similarly, the results indicate that analysis of PD-1 phosphorylation in tissues by immunohistochemistry can reflect responses to immunotherapy and further indicate that screening, such as CRISPR or shRNA screens, can be used to identify the kinase(s) responsible for PD-1 phosphorylation.

Figure 8D:
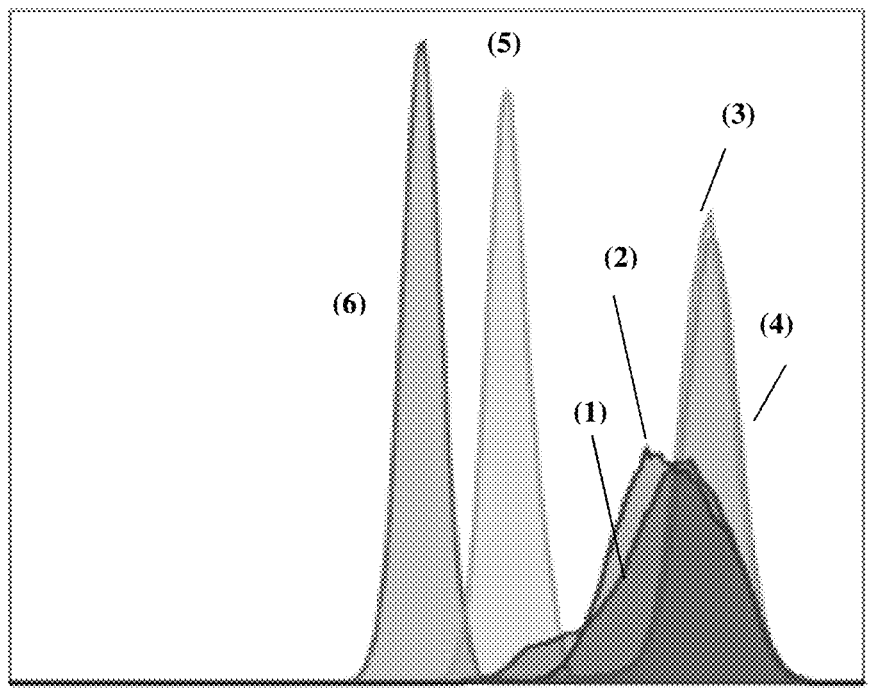
Figure 8E:
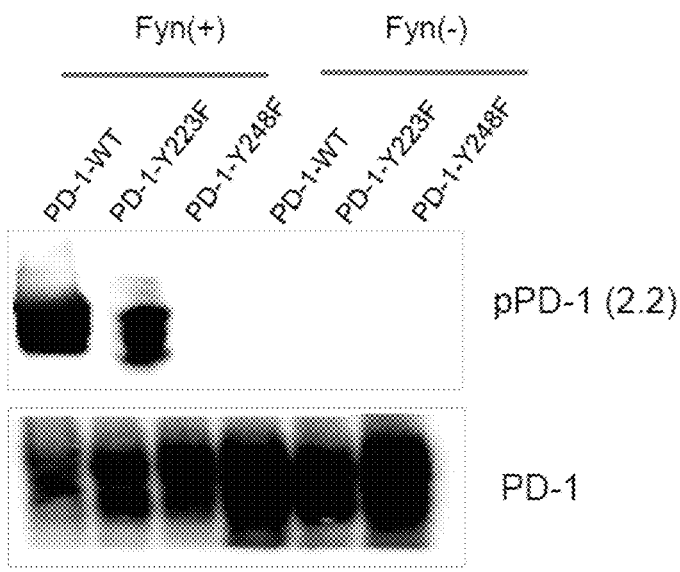
Figure 8F:
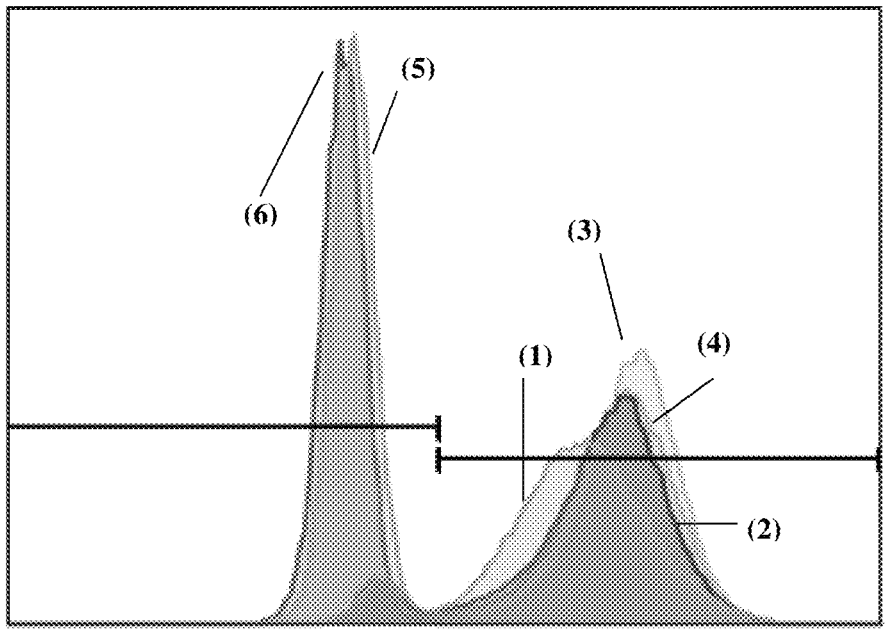
Figure 8G:
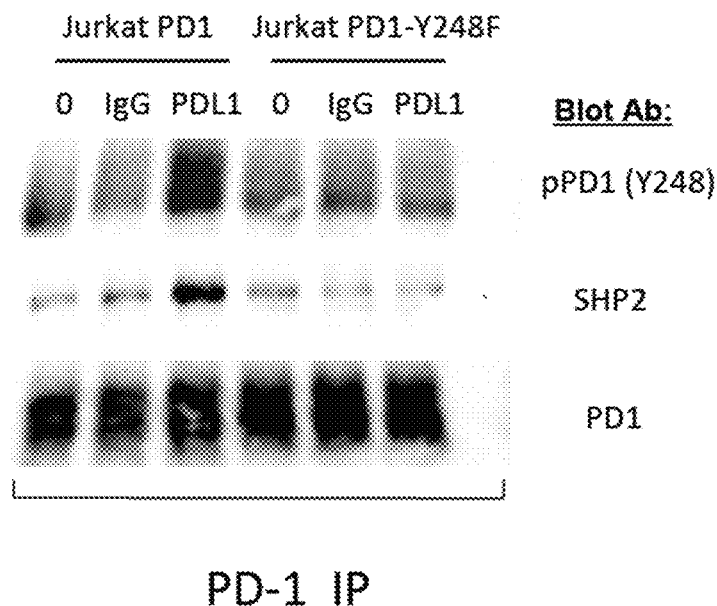

Example 3: Characterization of the T Cell Landscape: Detection of PD-1-Mediated Inhibitory Signal in T Cells and Implications in Tumor Immunotherapy In addition to the 6G12 antibody, several additional affinity-purified polyclonal anti-PD-1 antibodies that recognized tyrosine phosphorylation of the cytoplasmic site of PD-1 responsible for the interaction of PD-1 with the phosphatase, SHP-2, were generated. In particular, rabbit polyclonal antibodies specific for phosphorylated Y248 of PD-1 were generated against peptide immunogens (FIGS. 8A-8B), characterized (FIGS. 8C-8F), and used to confirm the importance of Y248 phosphorylation for the PD-1-SHP2 interaction (FIG. 8G). For the following experiments in this Example, the pPD-1 antibody named "2.2" was used. As described above, the antibodies can be used for a number of purposes. For example, the antibodies can be used to identify cells that receive a signal through the PD-1 receptor, leading to phosphorylation of this specific tyrosine in PD-1 cytoplasmic tail that is required for the recruitment of SHP-2. The antibodies are also useful for identifying patients who have evidence of PD-1-mediated inhibitory signaling since such patients are the best candidates to be benefitted by immunotherapy with PD-1 blockade, such as by assessing the presence of phospho-PD-1 positive cells in tumor biopsies. Moreover, the antibodies are useful for determining responses to PD-1/PD-L1-based immunotherapy. Patients who respond to immunotherapy by PD-1 or PD-L 1 blockade are believed to show decreased phosphorylation of PD-1 tyrosine 248 after treatment. In contrast, patients who do not respond to immunotherapy by PD-1 or PD-L 1 blockade are believed to have an unchanged or increased level phosphorylation of PD-1 tyrosine 248 after treatment. The antibodies are also useful for identifying patients who have evidence of PD-1-mediated inhibitory signaling as a consequence of chronic viral infections such as HIV, Hepatitis C, CMV or EBV. In such patients, cells positive for phosphorylated PD-1 tyrosine 248 can be detected in the peripheral blood and this finding will be useful to identify appropriate candidates for treatment with PD-1 blockade immunotherapy in order to re-invigorate antigen-specific T cells exhausted by chronic viral infections.

Figure 7A:
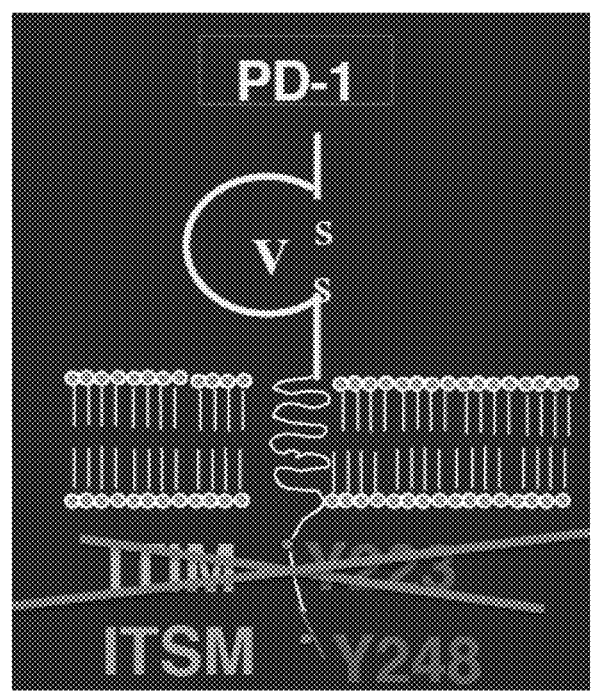
FIGS. 7A and 7B show that Y248 in the ITSM of PD-1 is the only tyrosine that mediates interaction with SHP2 and can be phosphorylated by Fyn.
Figure 7B:
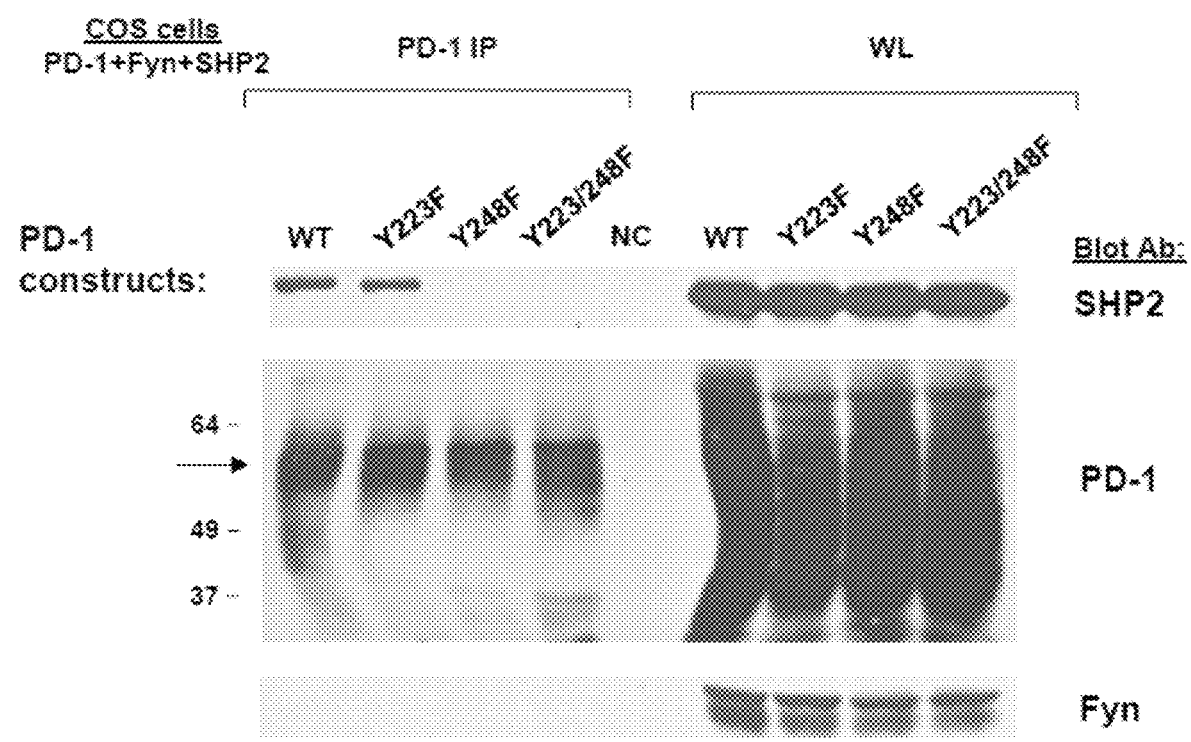

The generated polyclonal antibodies were subsequently used to identify the precise motif of PD-1 that is required for SHP-2 interaction and PD-1 inhibitory function. Using immunoprecipitation with PD-1-specific antibody followed by Western blot with SHP-2 antibody, it was determined that PD-1 interacted with SHP-2 after PD-1 ligation with simultaneous TCR/CD3-mediated activation, which was recapitulated by the expression of the TCR-proximal kinase, Fyn. This interaction required phosphorylation of the ITSM and was abrogated when the ITSM tyrosine Y248 was mutated to phenylalanine (FIG. 7B). In contrast, when the ITIM tyrosine Y223 was mutated, interaction of PD-1 with SHP-2 remained unaffected (FIG. 7B). Thus, Y248 in ITSM is the only tyrosine of PD-1 that mediates interaction with SHP2 (FIG. 7A). Based on these findings, without limitation, the phosphorylation of Y248 (e.g., by Fyn) is indicative of PD-1-mediated inhibitory signaling.

Figure 9A:
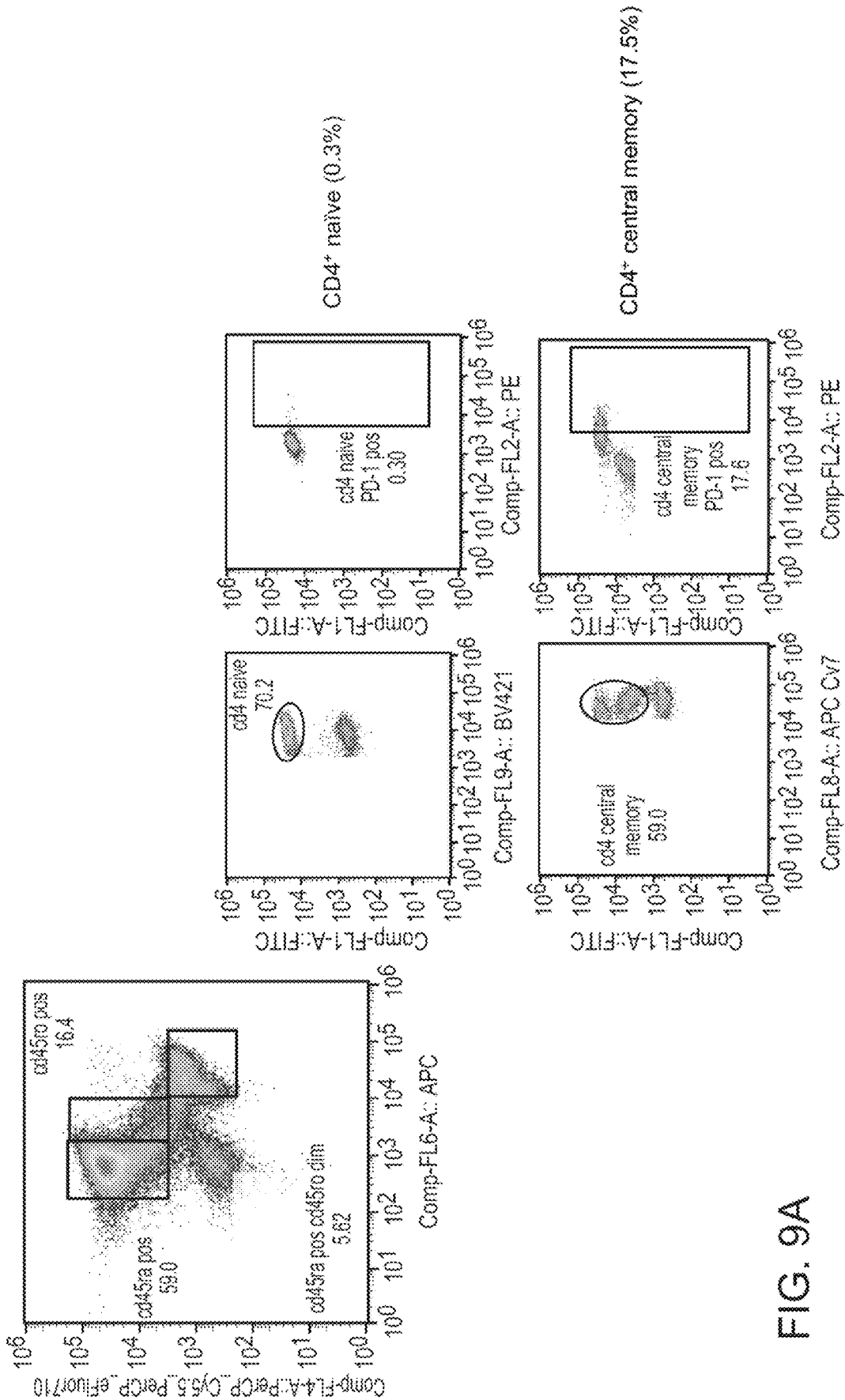
FIGS. 9A-9D show the detection of PD-1 in T cell subsets of human peripheral blood.
Figure 9A:
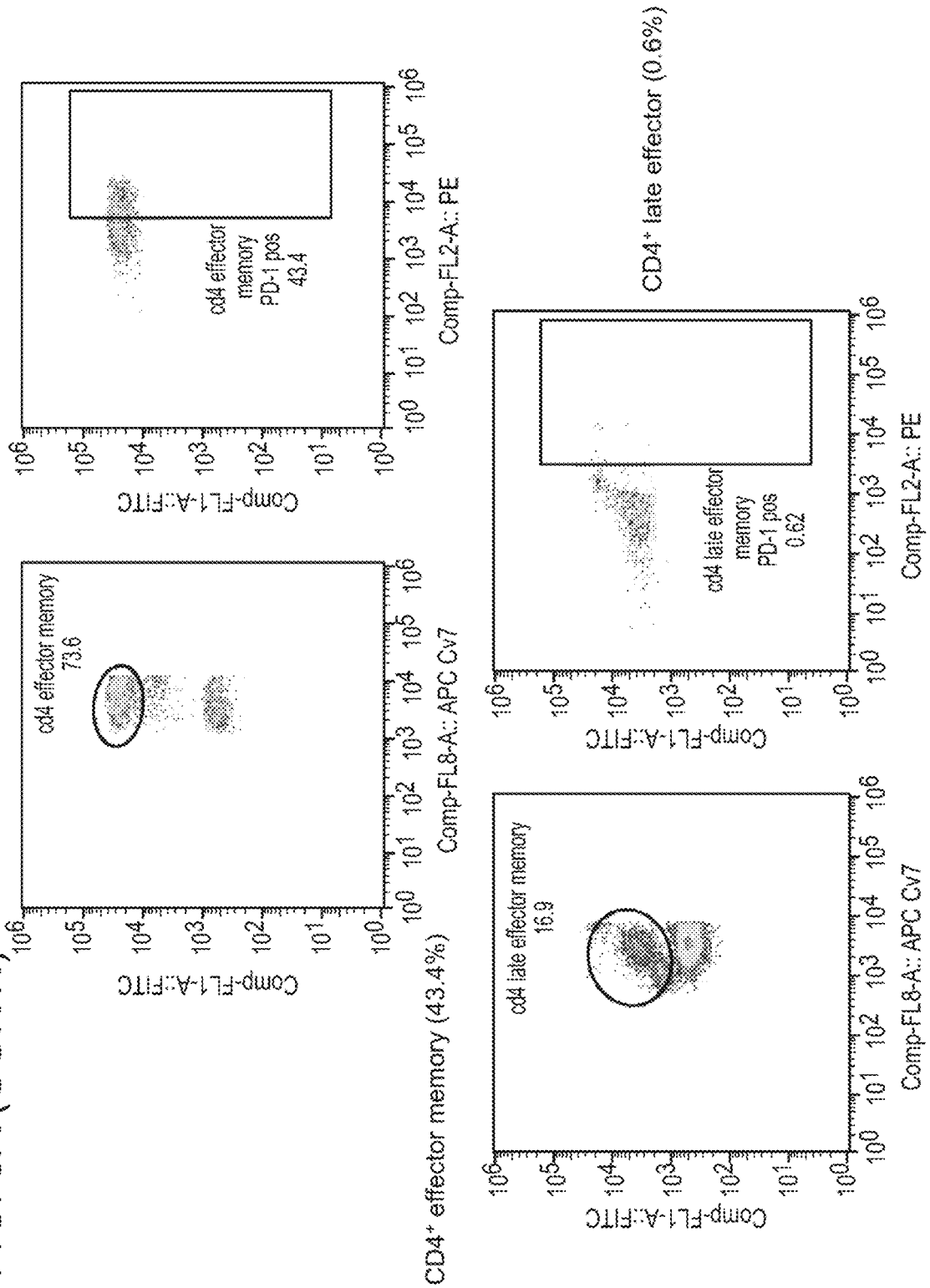
Figure 9B:
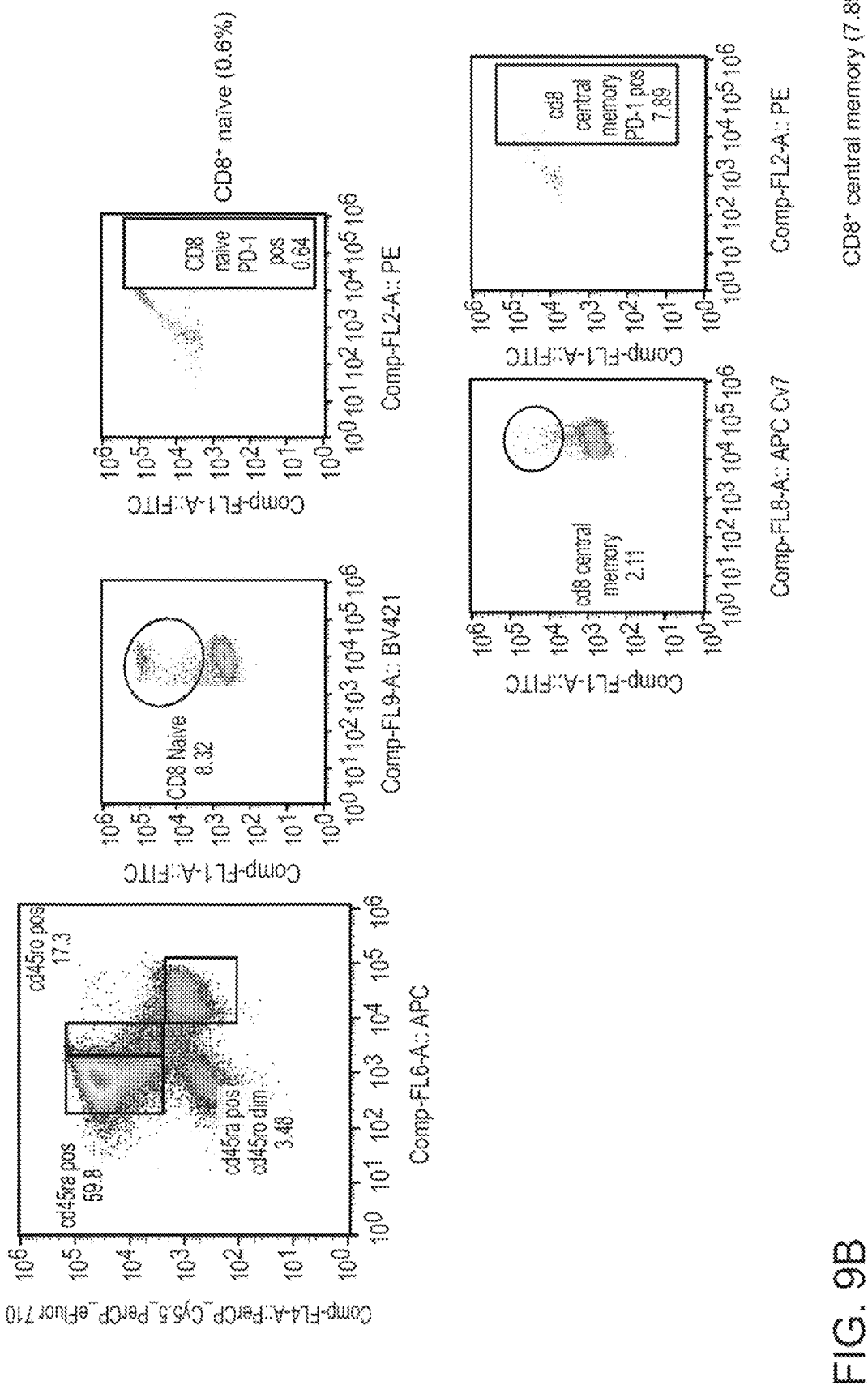
Figure 9B:
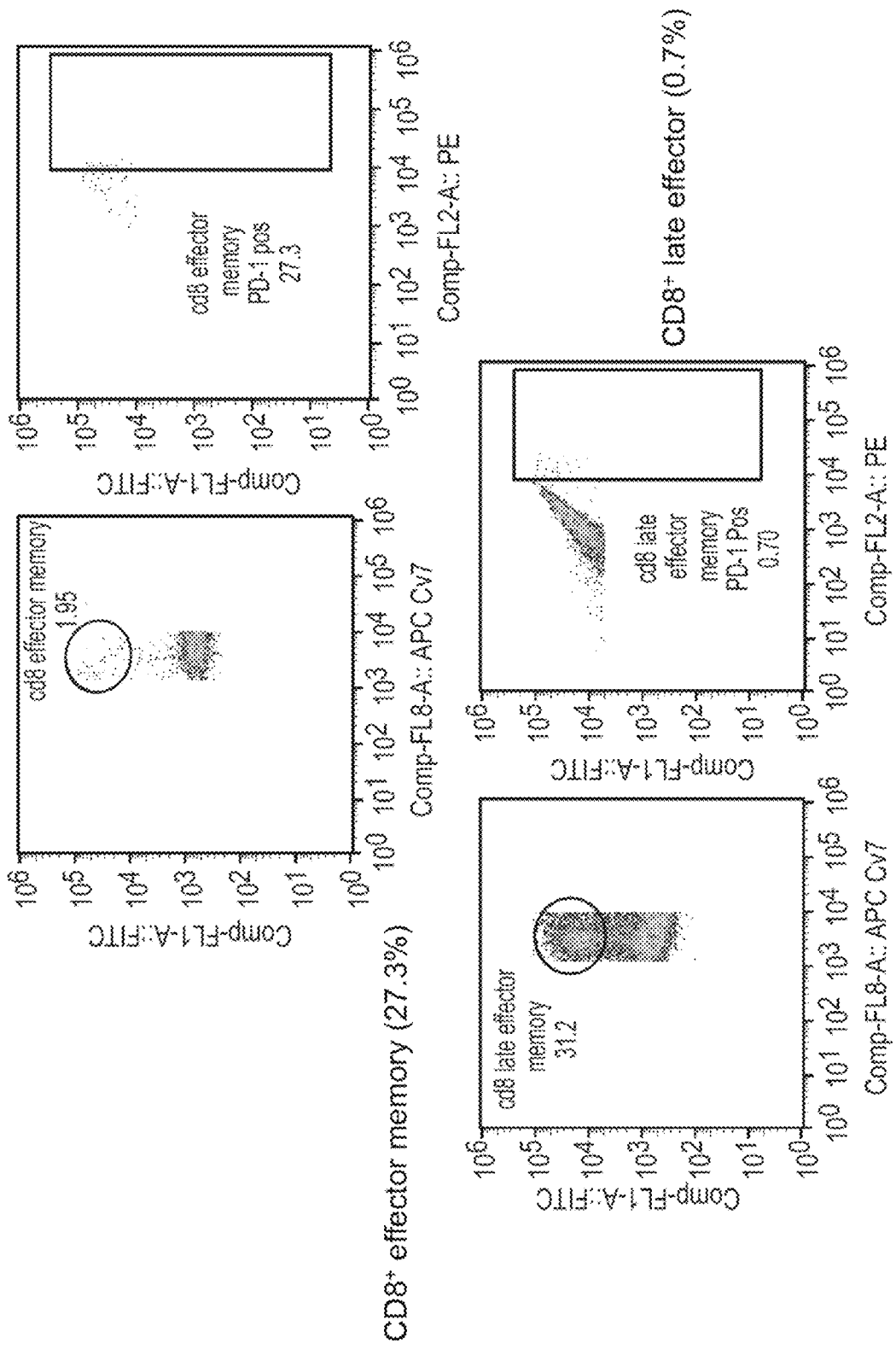
Figure 9C:
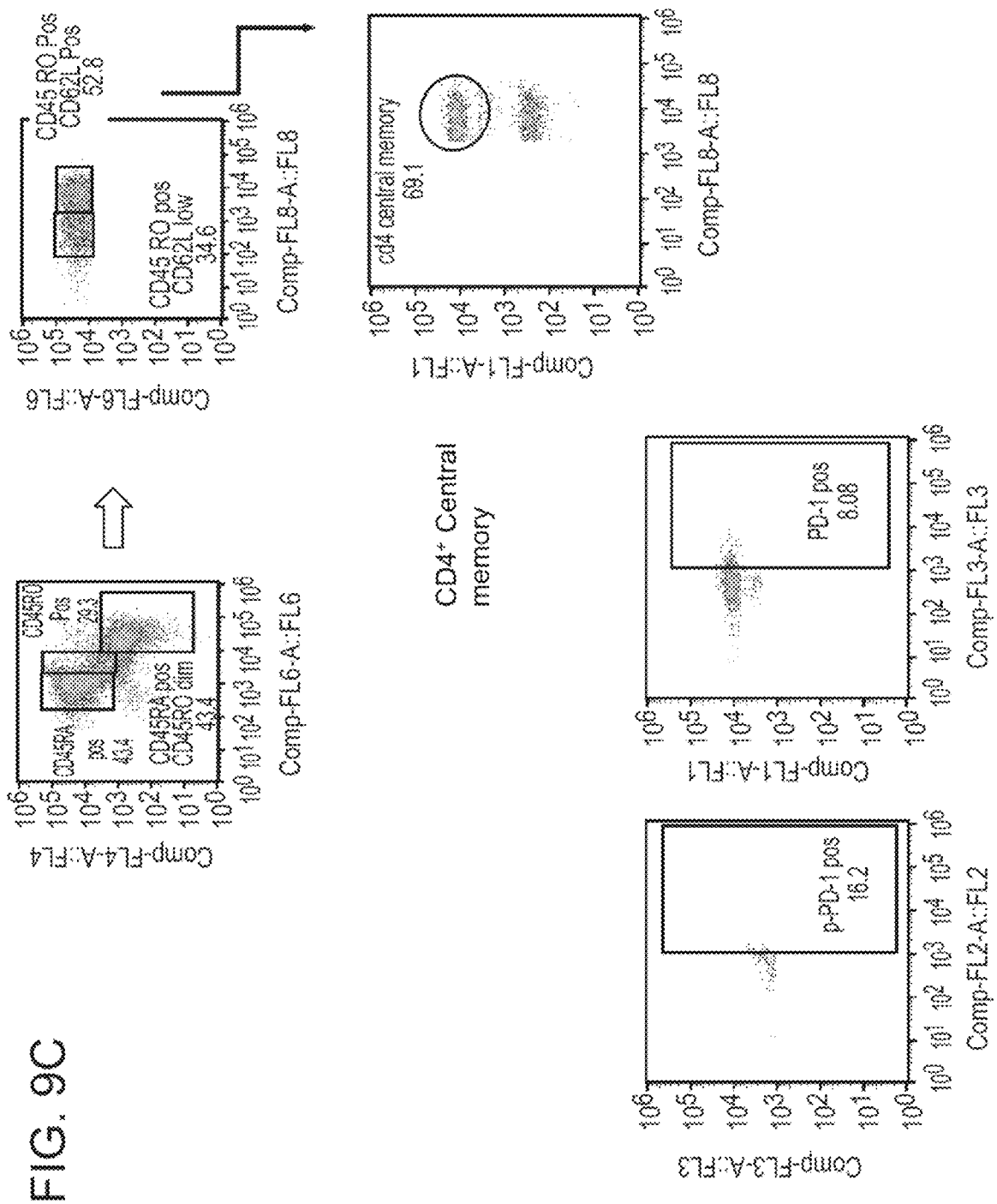
Figure 9C:
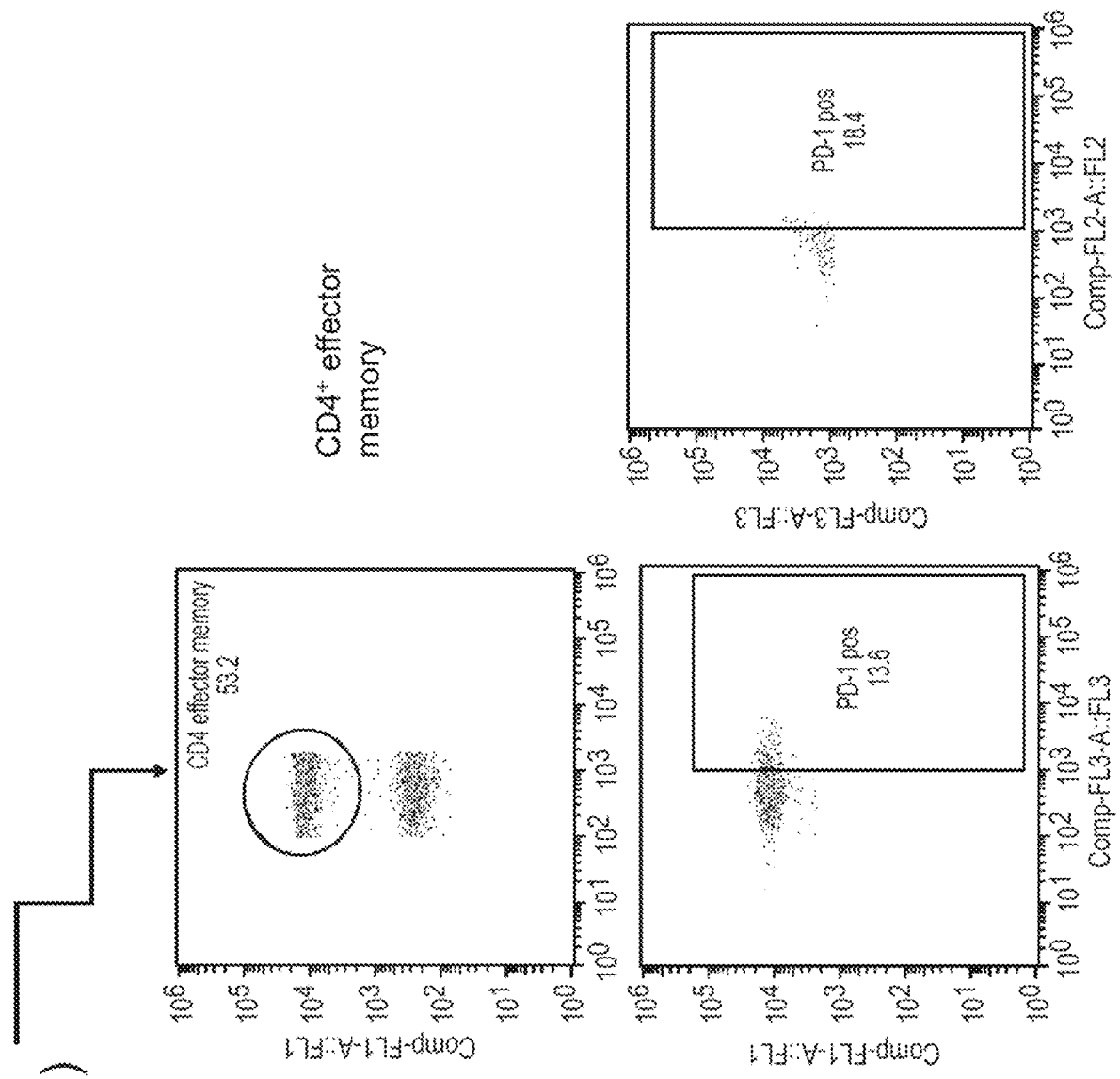
Figure 9D:
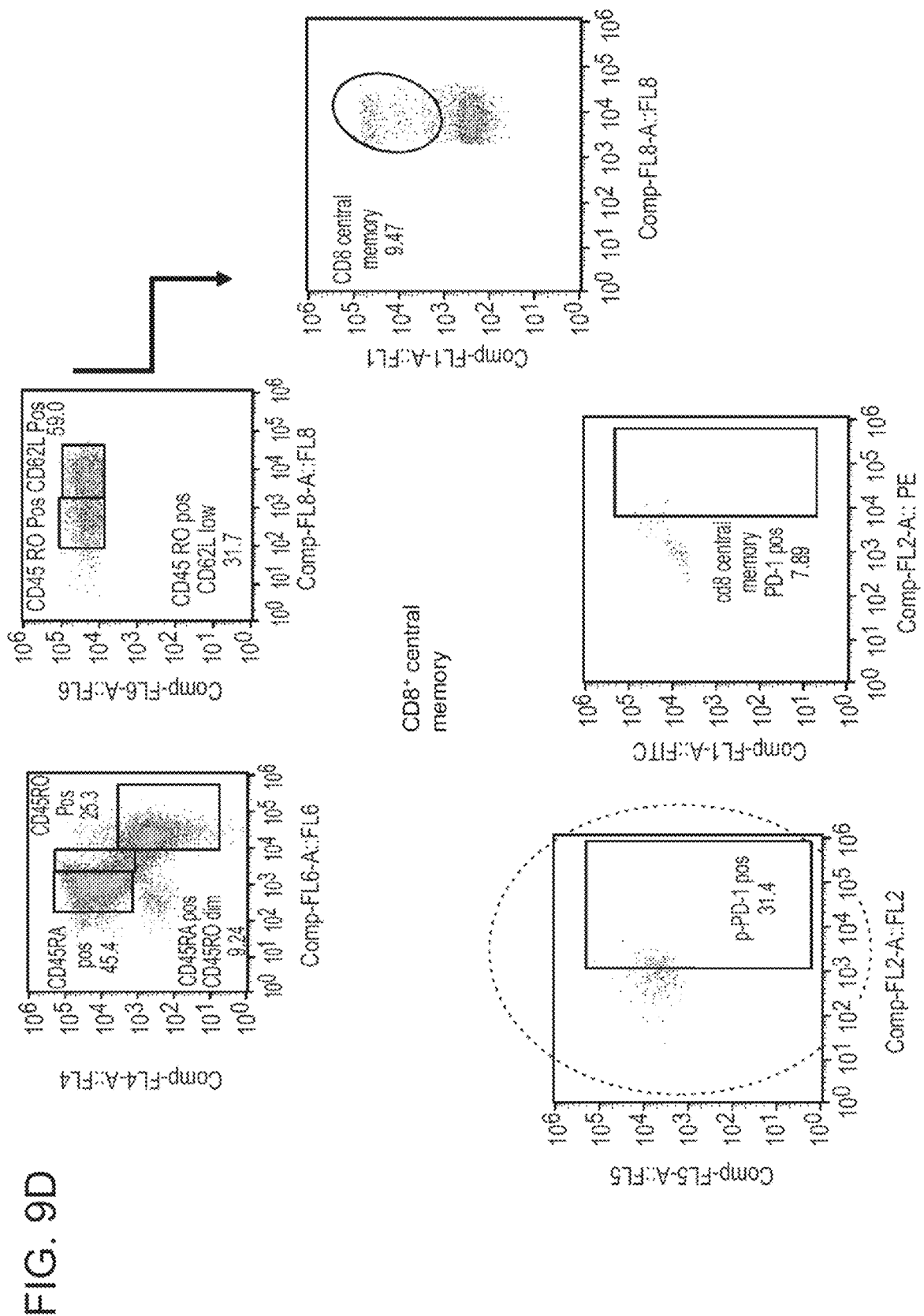
Figure 9D:
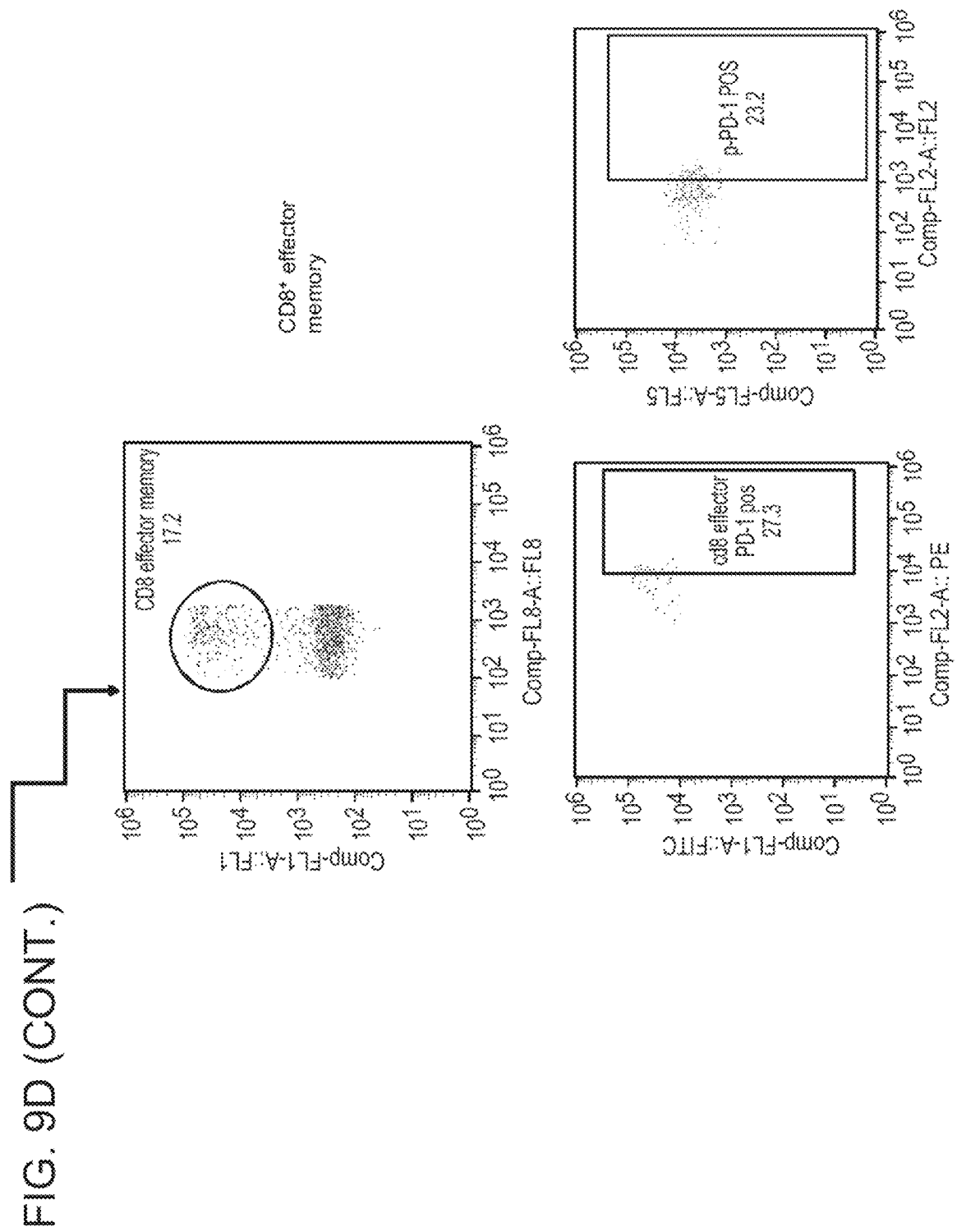
Figure 10:
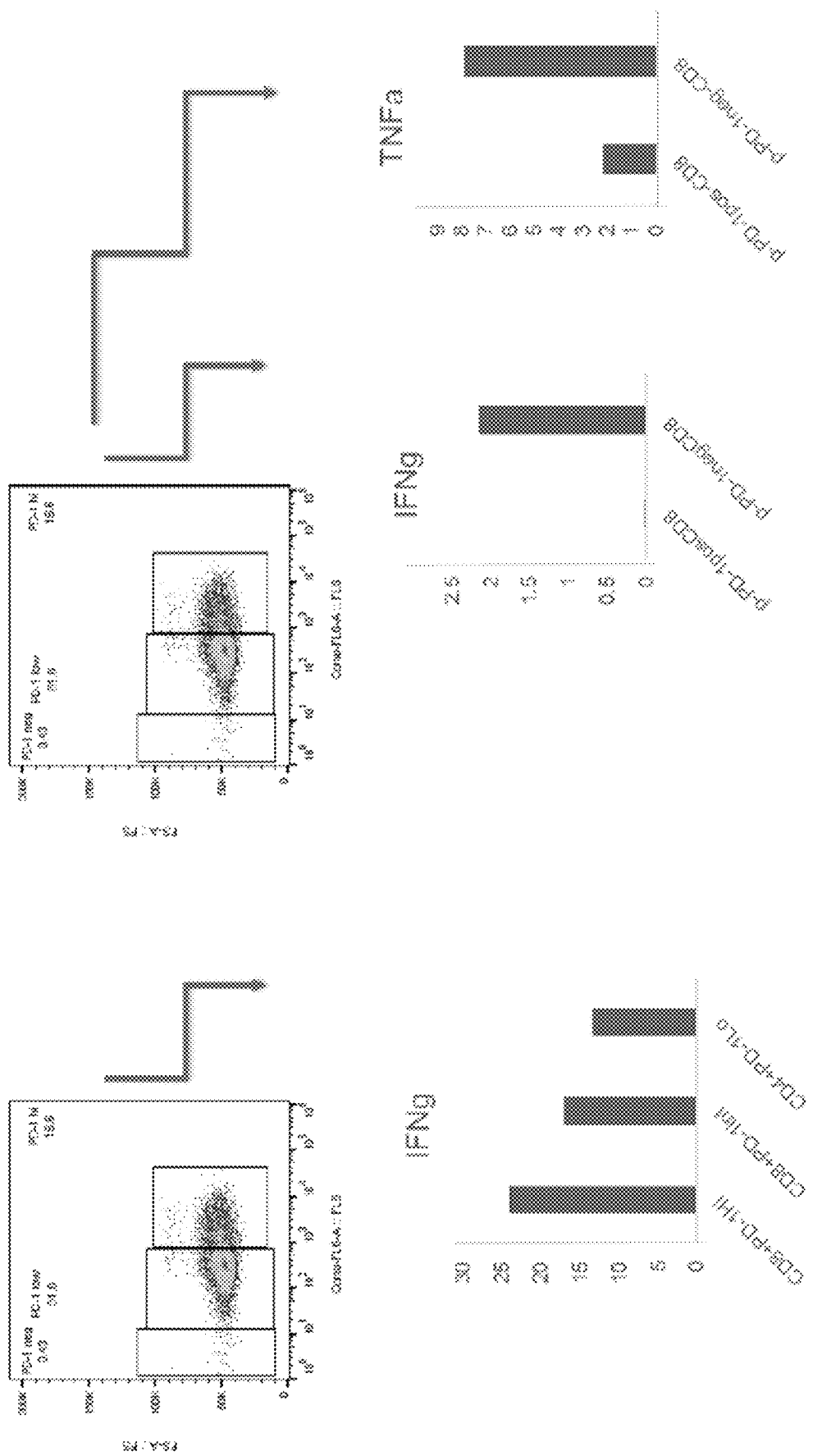
FIG. 10 shows that PD-1 Y248 phosphorylation, but not PD-1 expression level, inversely correlates with inhibition of CD8+ T cell activation and effector function.

The expression and function of PD-1pY248+ T cells (i.e., T cells expressing PD-1 which is phosphorylated on Y248) in peripheral blood from healthy humans was examined PD-1pY248+ cells were detected within the CD4 but mostly CD8 T cell populations, mainly in central memory and effector memory subsets and in much lower extent in terminally differentiated effectors (FIG. 9C-9D). Although PD-1$^{high}$ did not correlate with altered ability of CD8 T cells to produce effector cytokines, PD-1pY248+ expression correlated with impaired production of IFN-γ and TNF-α in response to TCR/CD3+CD28-mediated stimulation (FIG. 10). Thus, PD-1pY248 serves as a biomarker indicative of PD-1 mediated inhibitory signaling in patients with, e.g., chronic infections and/or cancer.

Figure 11:
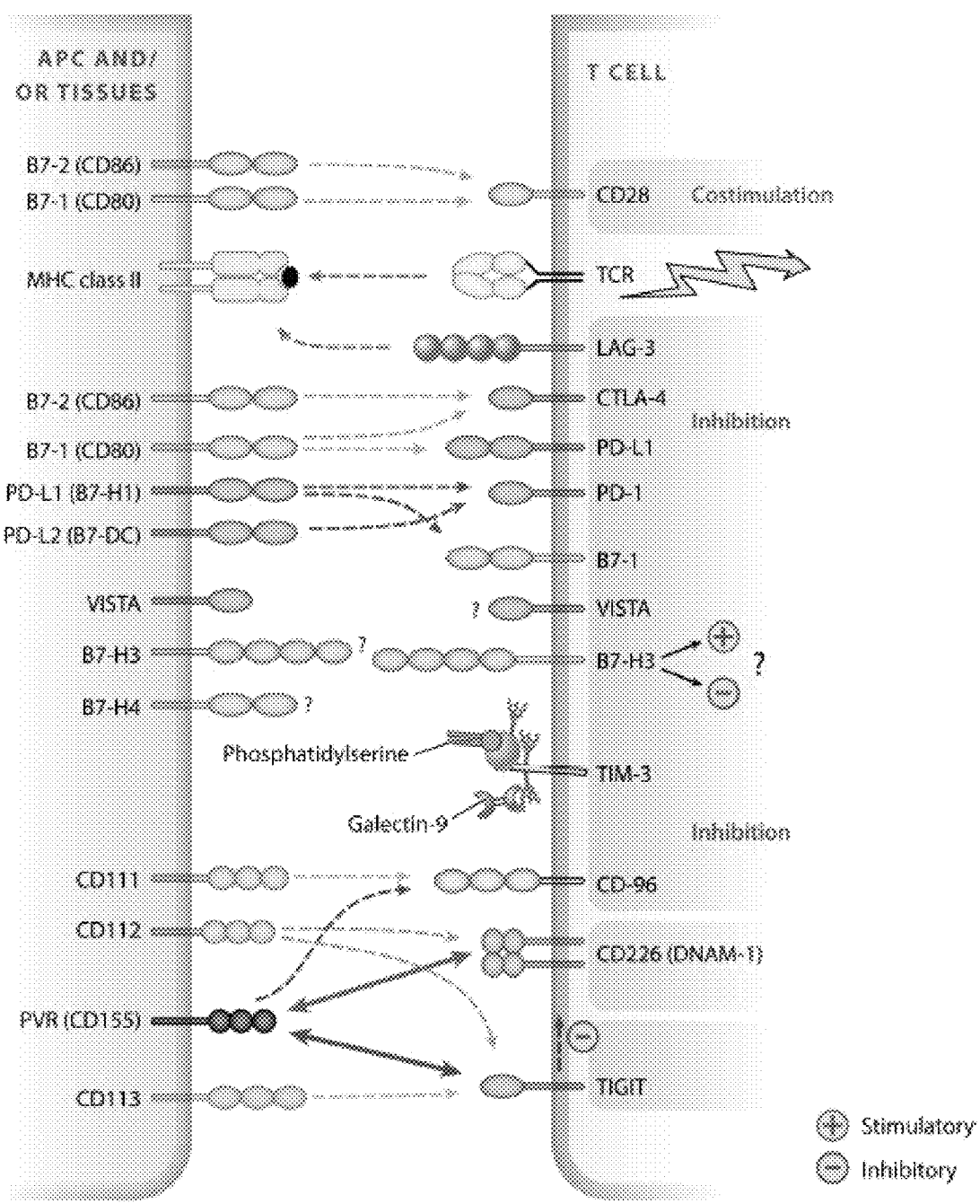
FIG. 11 summarizes multiple co-inhibitory pathways having a role in cancer immunotherapy.
Figure 12:
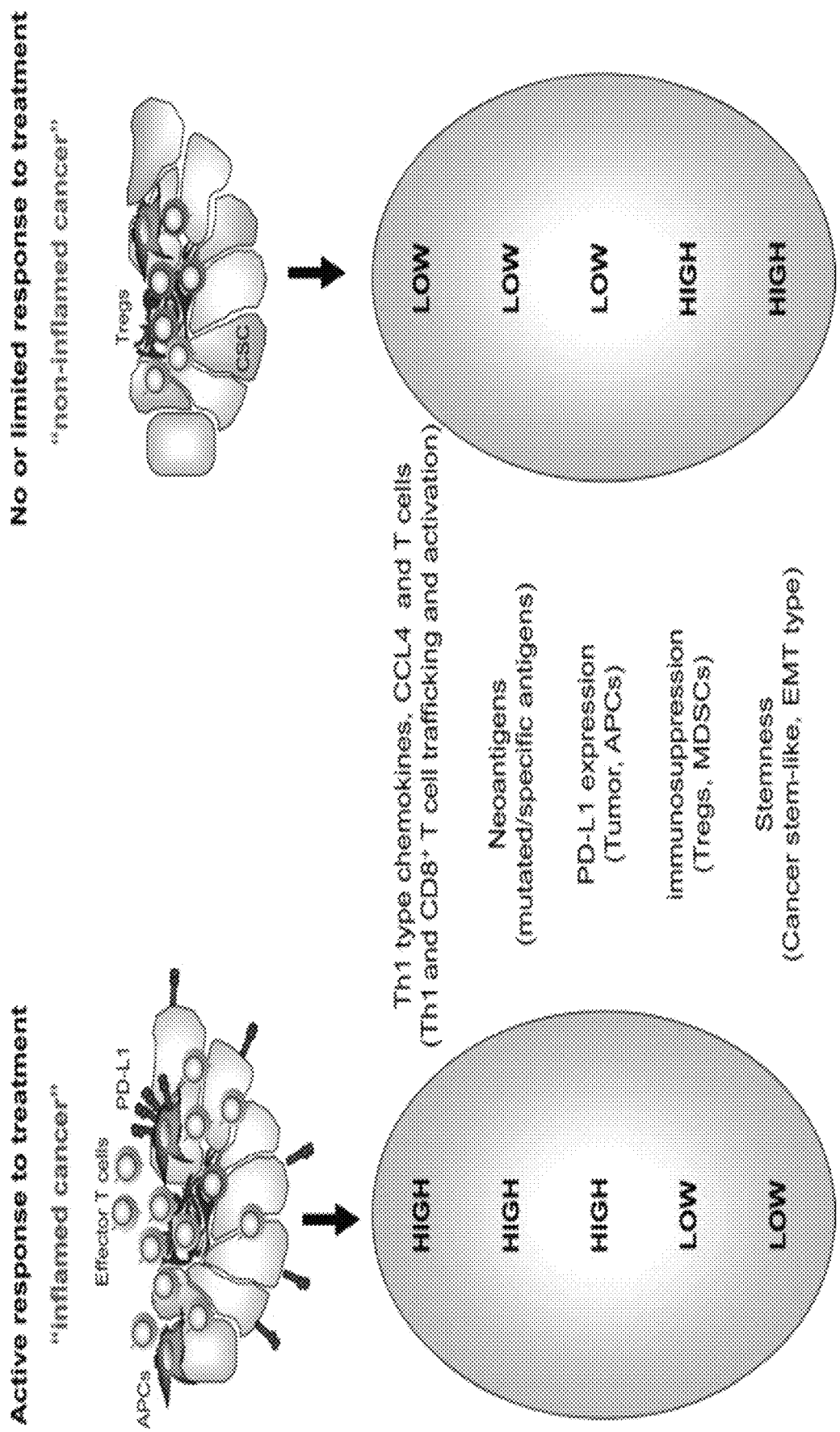
FIG. 12 compares the expression profiles of various biomarkers in various cancer scenarios.
Figures 13A, 13B, 13C:
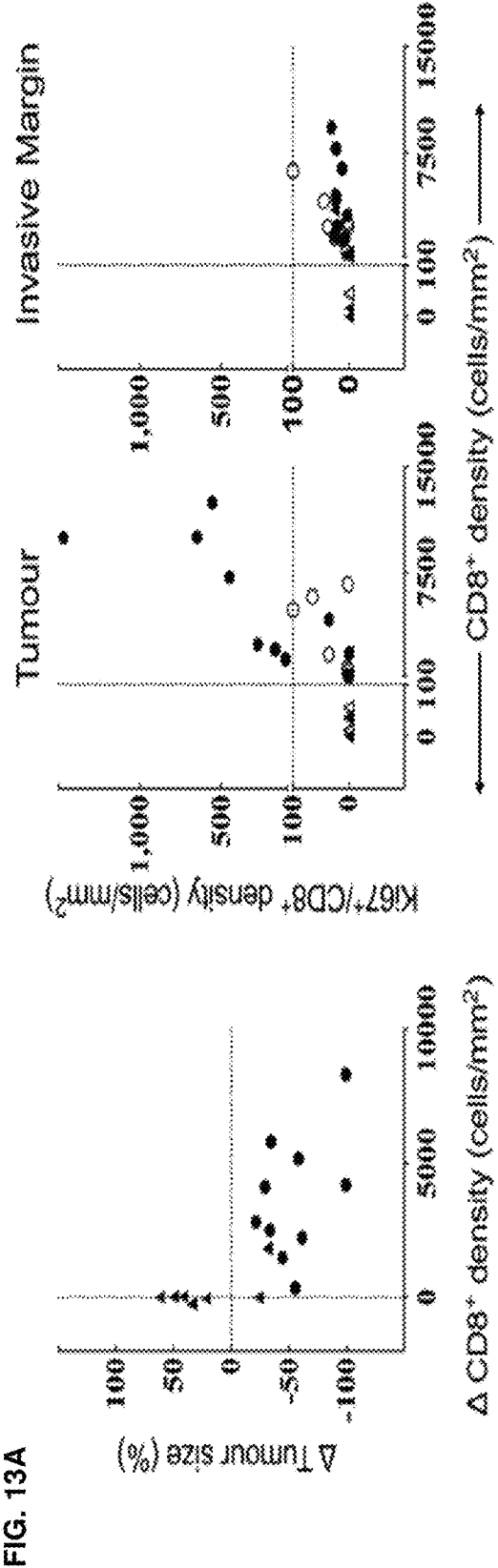
FIGS. 13A-13C show high proliferative capacity of CD8$^+$ T cells in tumors correlate with response to immunotherapy.

Multiple co-inhibitory pathways have a role in cancer immunotherapy (FIG. 11, see Baumeister et al. (2016) *Annu. Rev. Immunol.* 34:539-573). Specifically, PD-1 signaling has important implications in cancer. For example, PD-L1 expression was found in multiple breast cancer cell lines, such as MDA-231, SKBR-3, MCF-7, and BT474. PD-1-targeting therapies have best anti-tumor responses observed against melanoma, non-small cell lung cancer, and renal cancer, while several other cancers respond to PD-1-targeting therapies at a lesser extent. Durable responses have been achieved in 20-40% of patients. In order to improve the outcome of PD-1 targeting in cancer therapy, it is necessary to understand the molecular mechanisms by which PD-1 inhibits T cell responses and to develop meaningful biomarkers of patient eligibility and response to treatment. Some potential biomarkers are shown in FIG. 12. Specifically, high proliferative capacity of CD8+ T cells in tumors correlate with response to immunotherapy (FIG. 13).

With the anti-phosph-PD-1 antibodies disclosed herein, it was discovered that PD-1 Y248 phosphorylation, instead of PD-1 expression level, strongly correlates with inhibition of T cell effector function. Thus, identification of PD-1pY248+ cells serves as a biomarker for PD-1-mediated T cell inhibitory signals in cancer patients. In addition, reversal of PD-1 pY248 phosphorylation after PD-1:PD-L1 blocking immunotherapy can be used as a biomarker indicative of response to treatment.

Figure 14A:
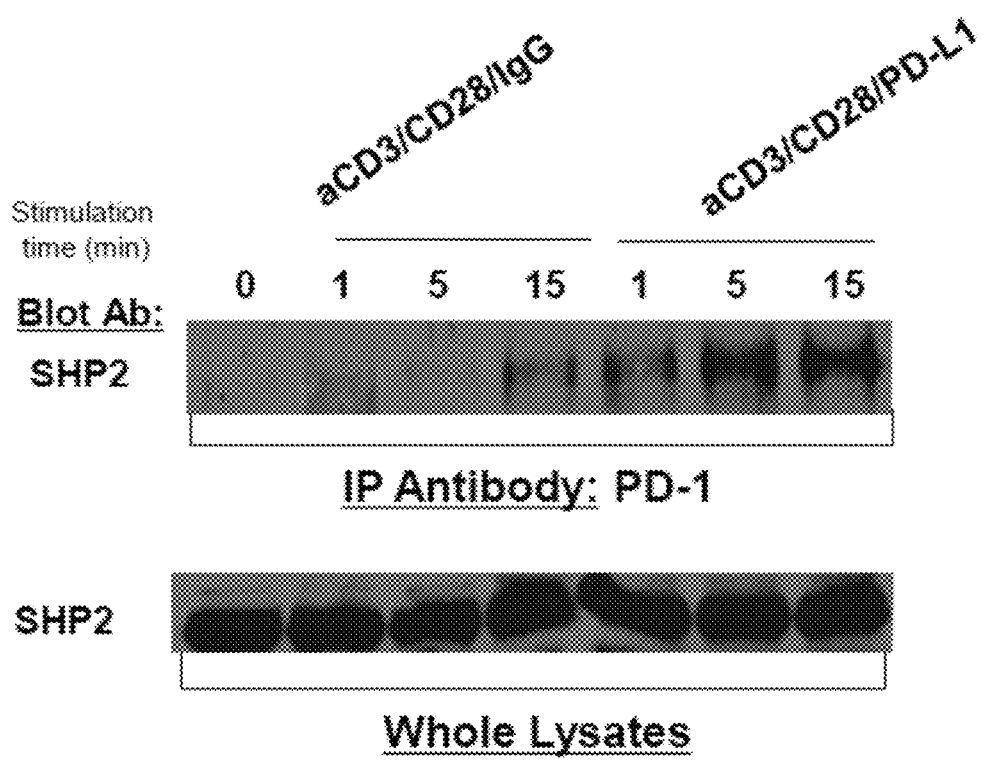
FIGS. 14A-14C show that among the TCR proximal kinases, Fyn mediates the most potent phosphorylation of PD-1 Y248.
Figure 14B:
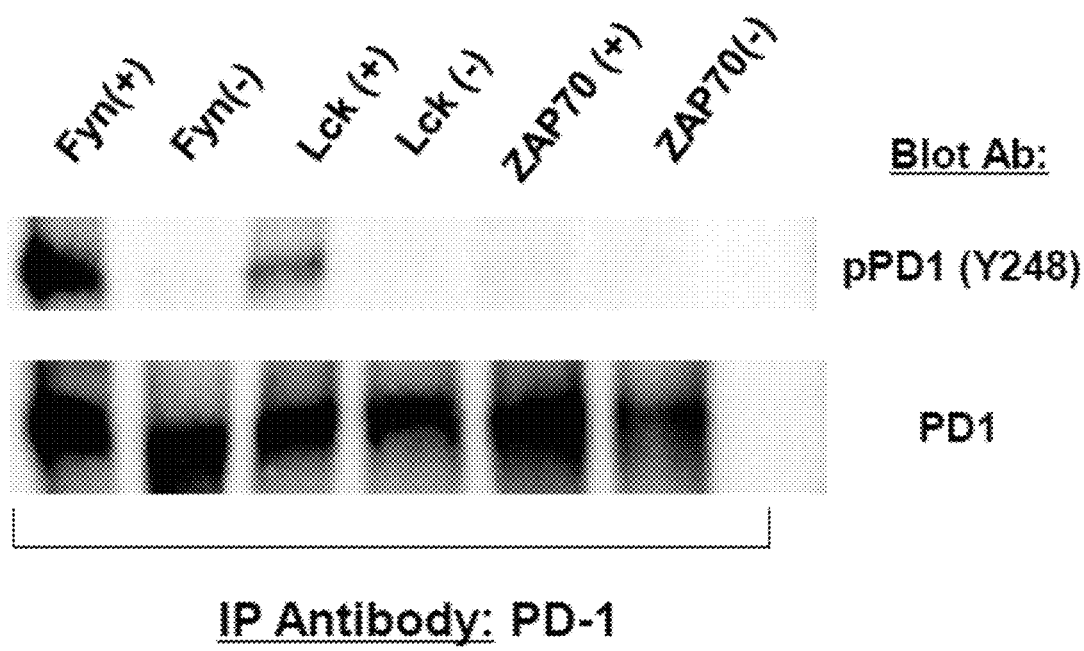
Figure 14C:
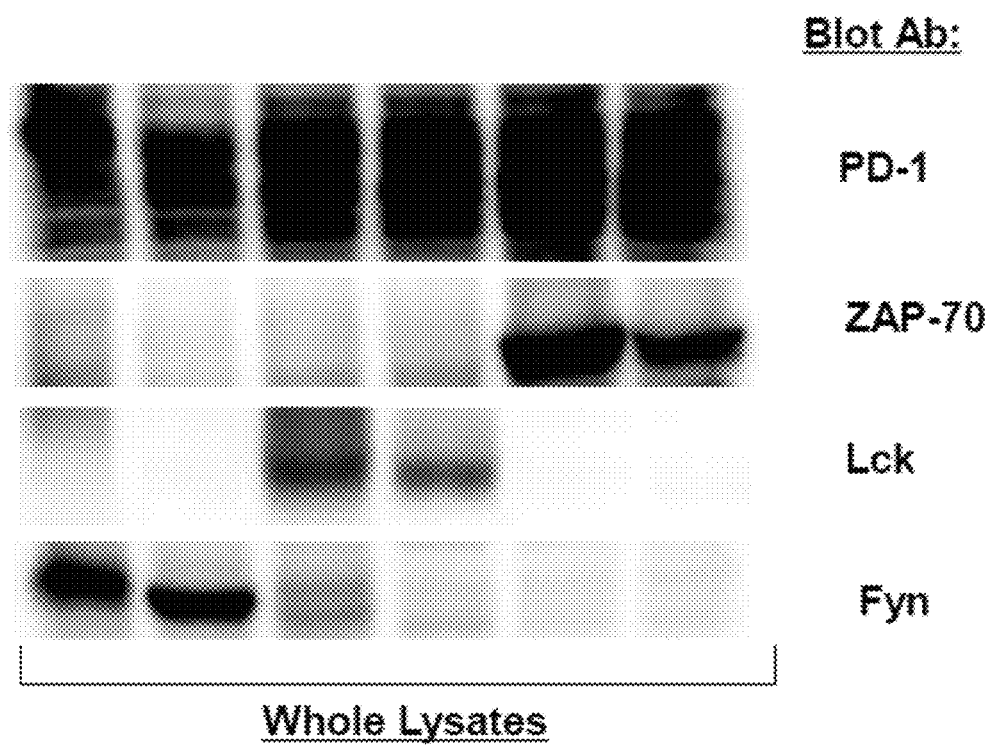
Figure 15A:
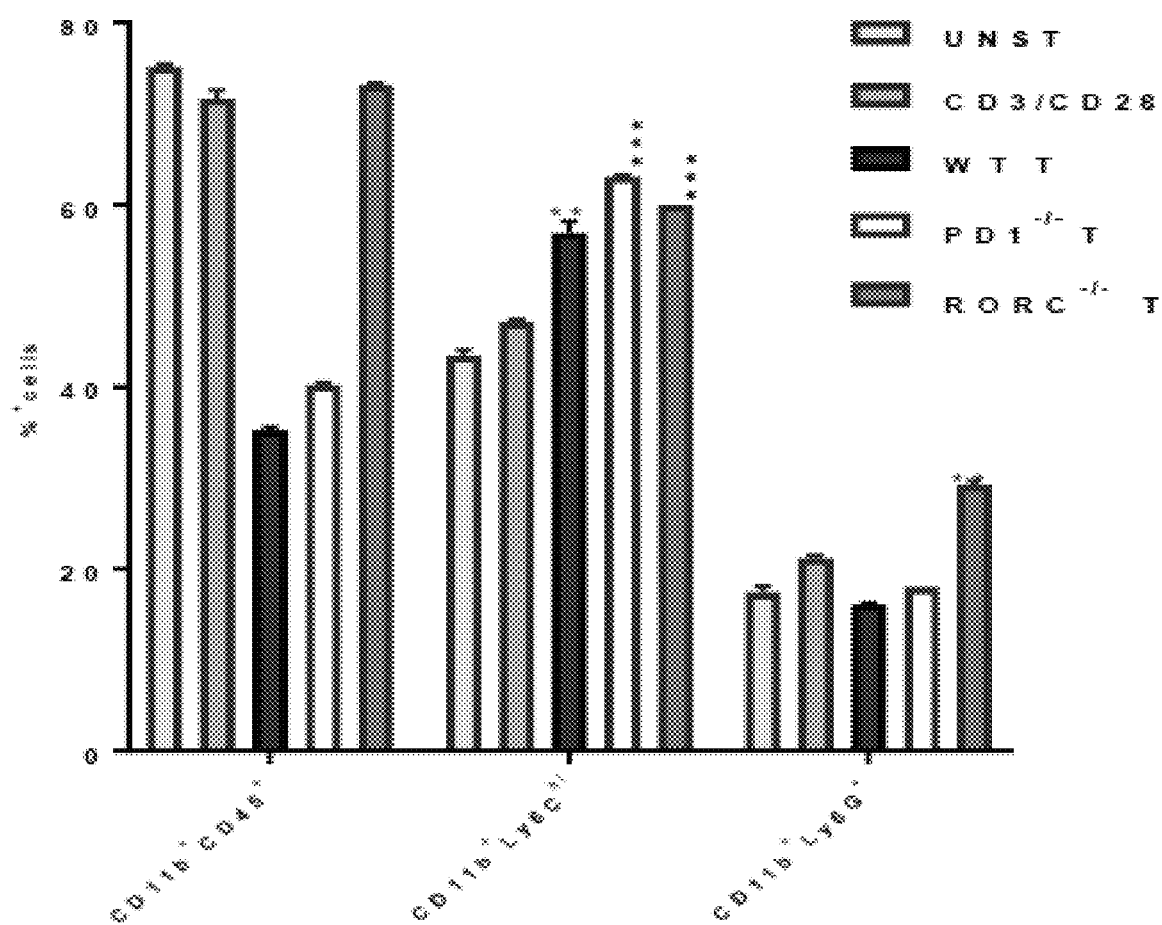
FIGS. 15A-15F show the phospho-PD-1 levels in MDSCs co-incubated with naïve T cells and CD3/CD28 stimulation for four days.
Figure 15A:
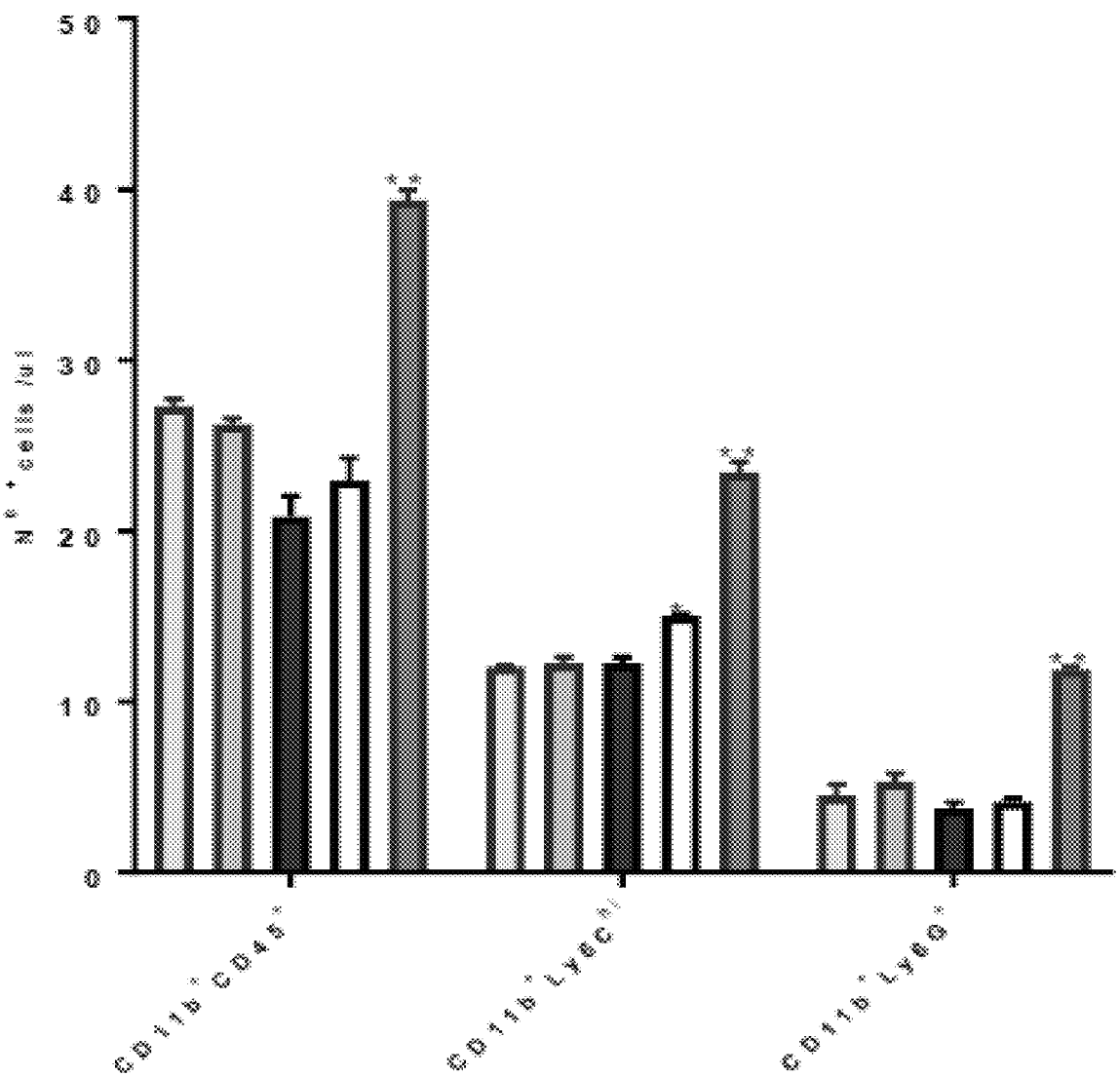
Figure 15B:
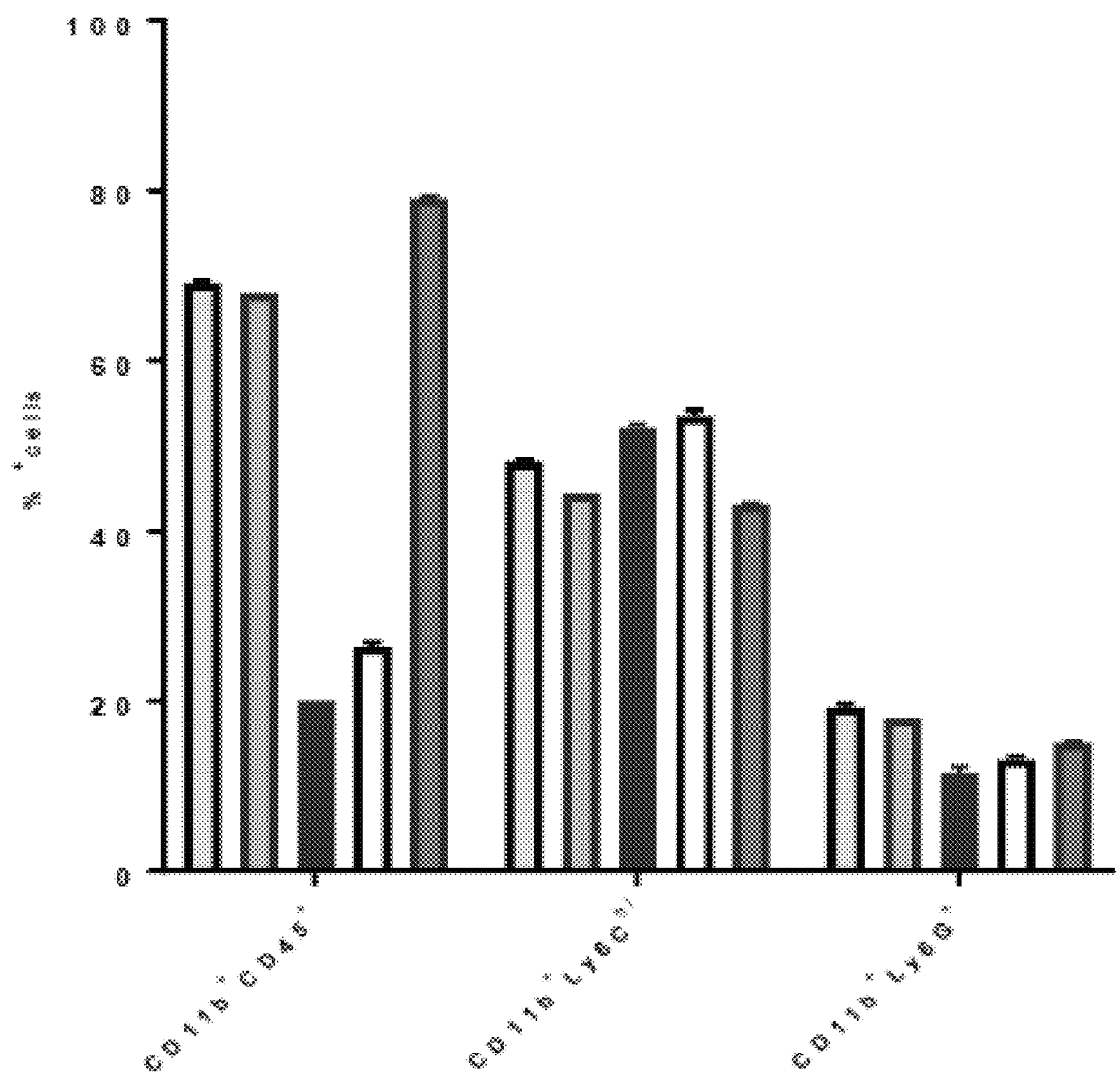
Figure 15B:
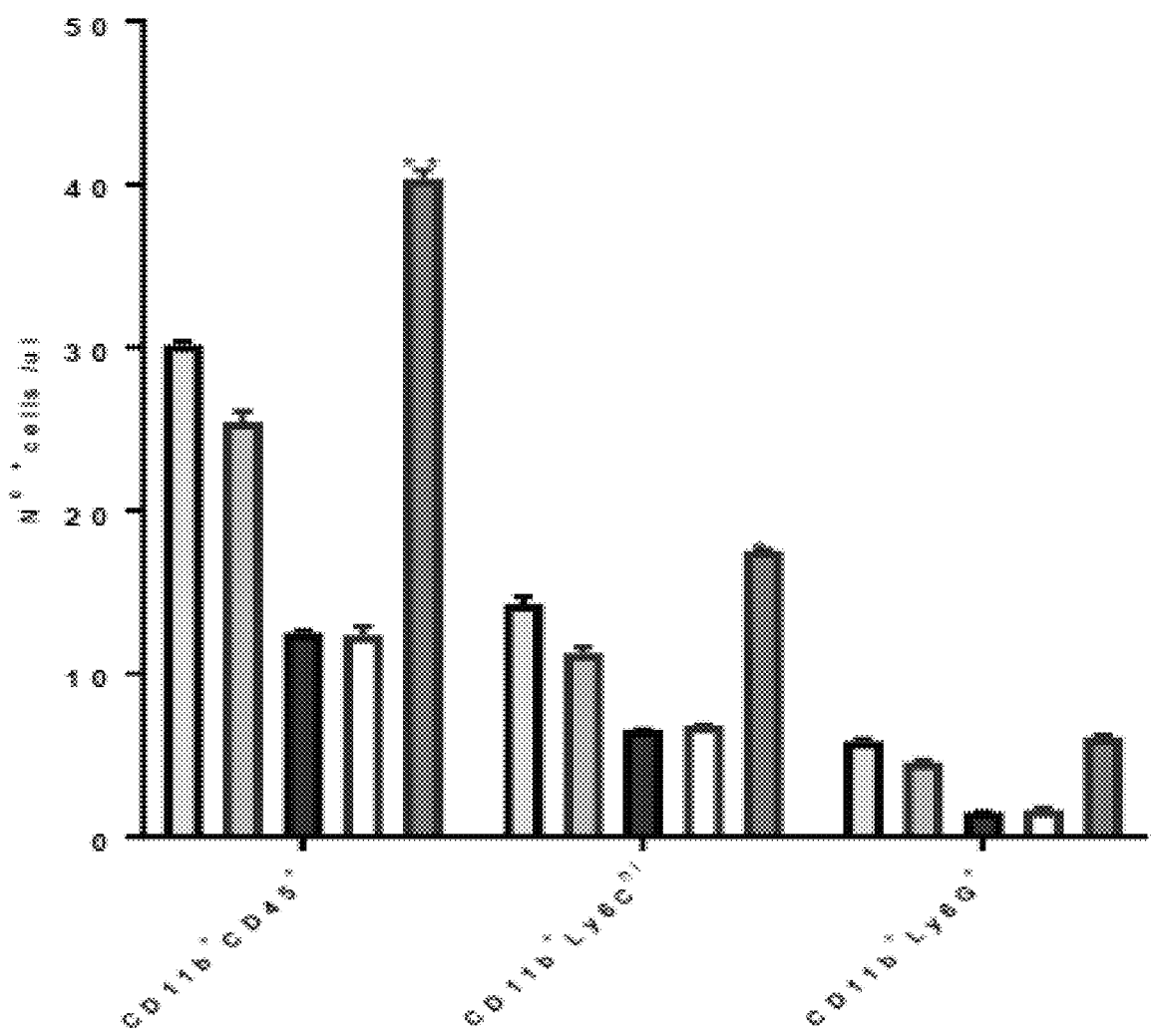
Figure 15C:
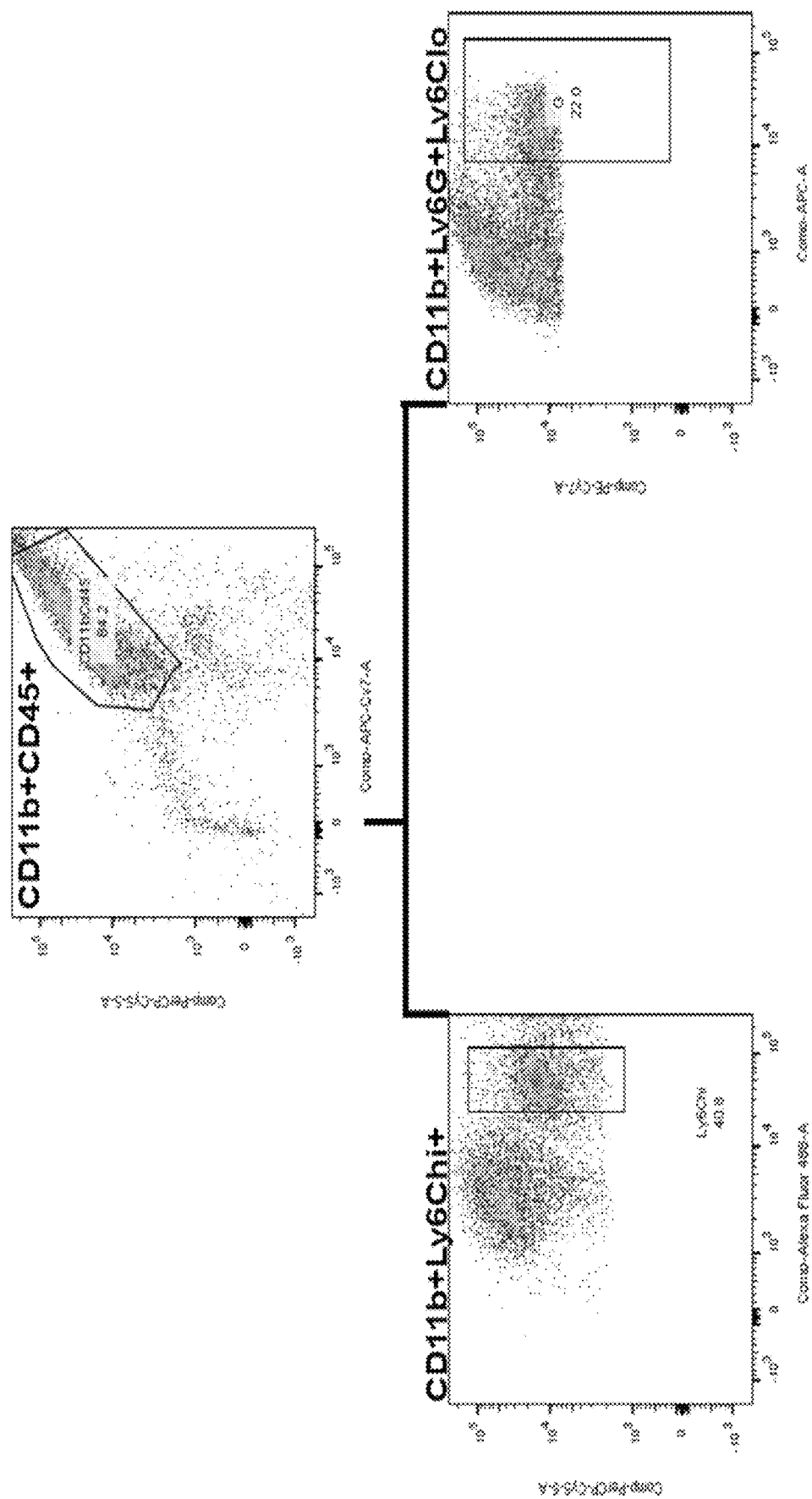
Figure 15D:
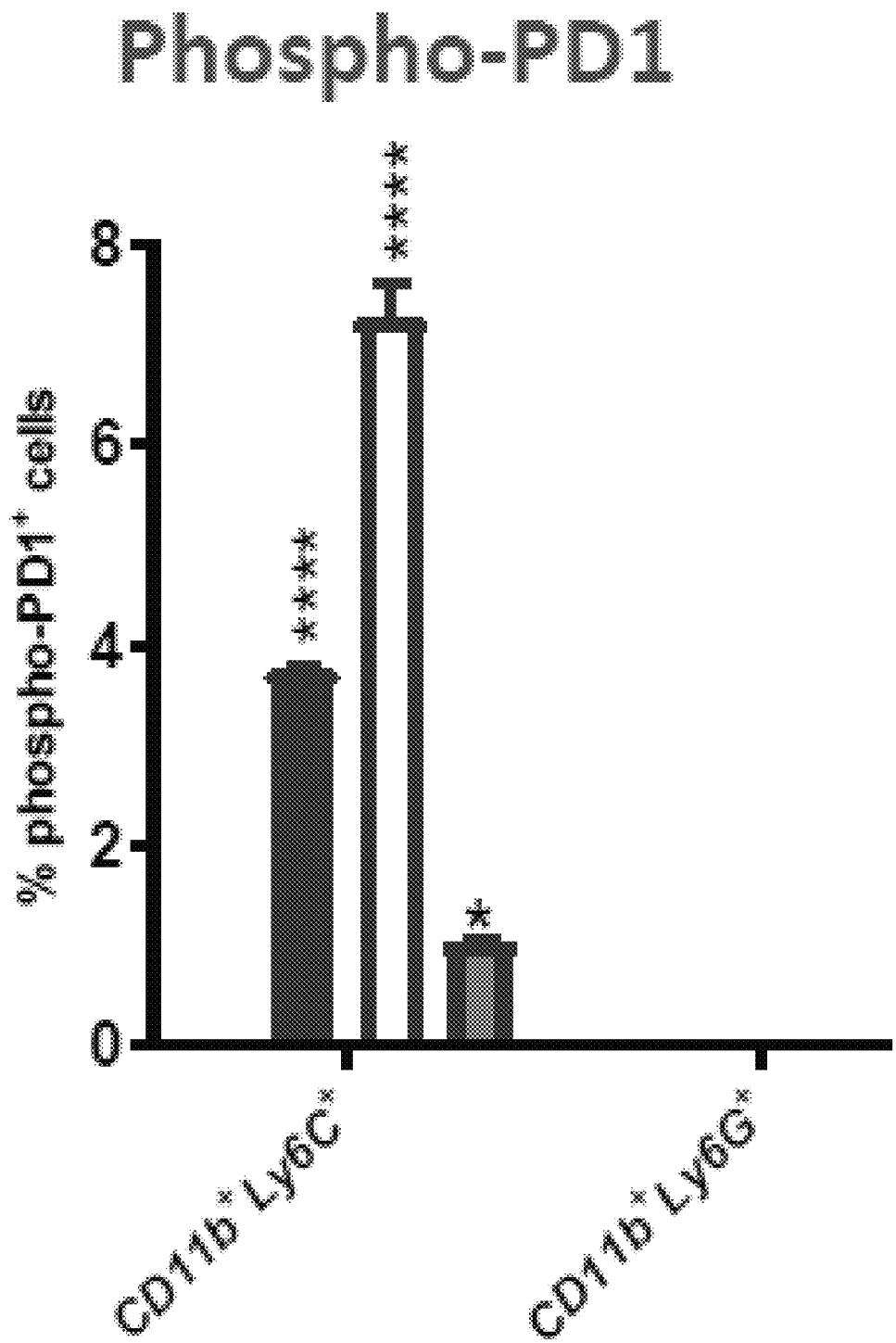
Figure 15D:
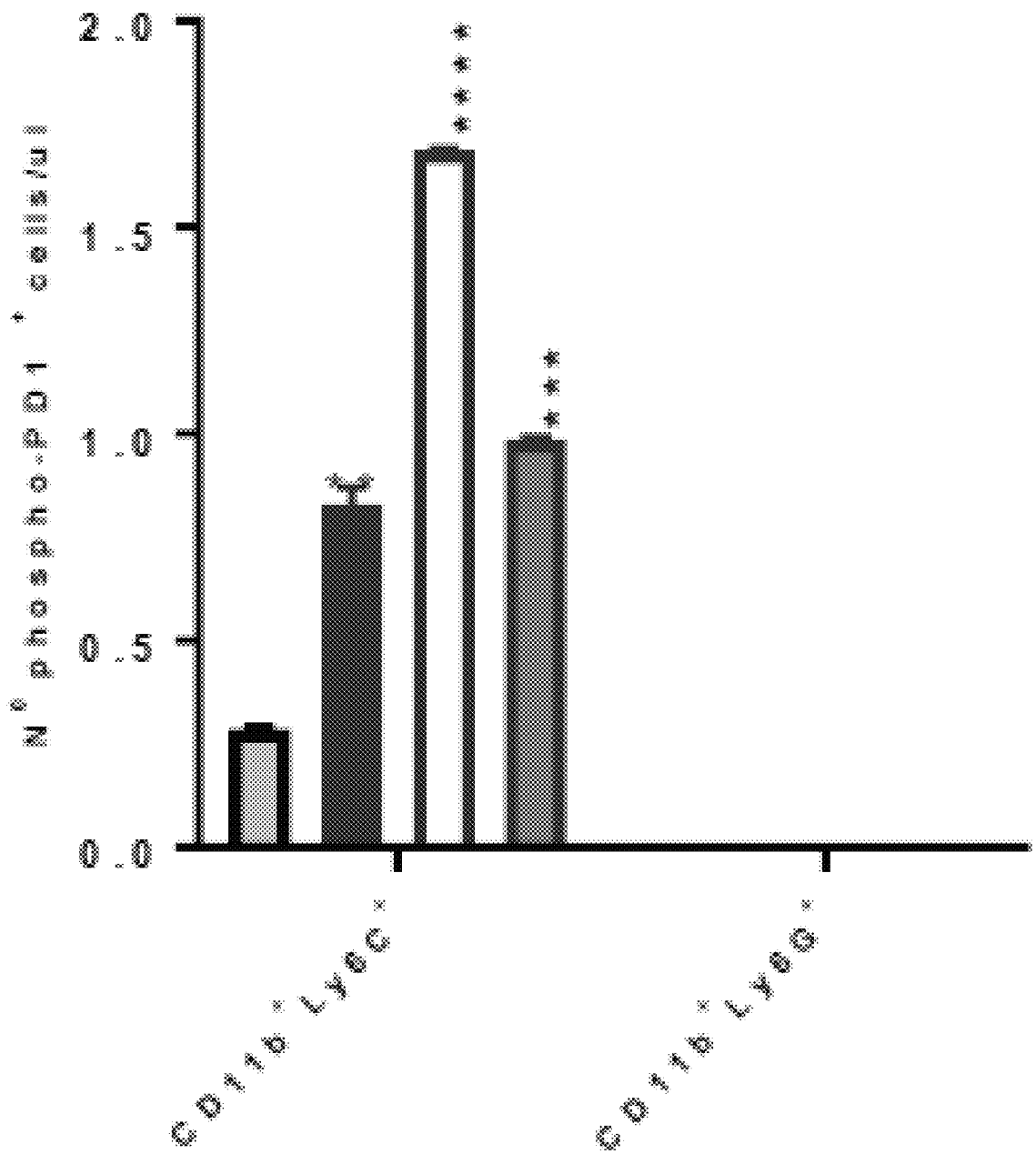
Figure 15E:
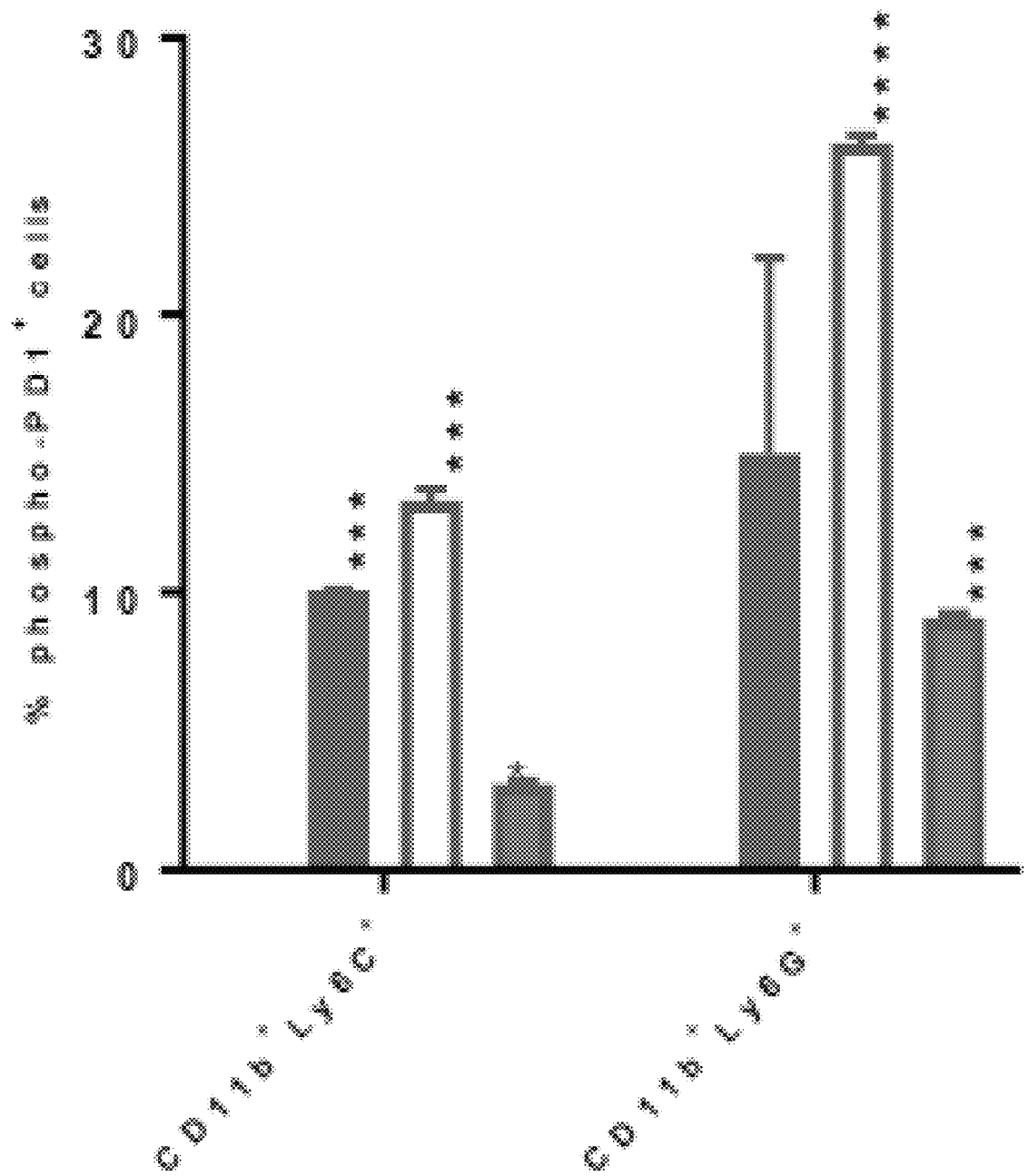
Figure 15E:
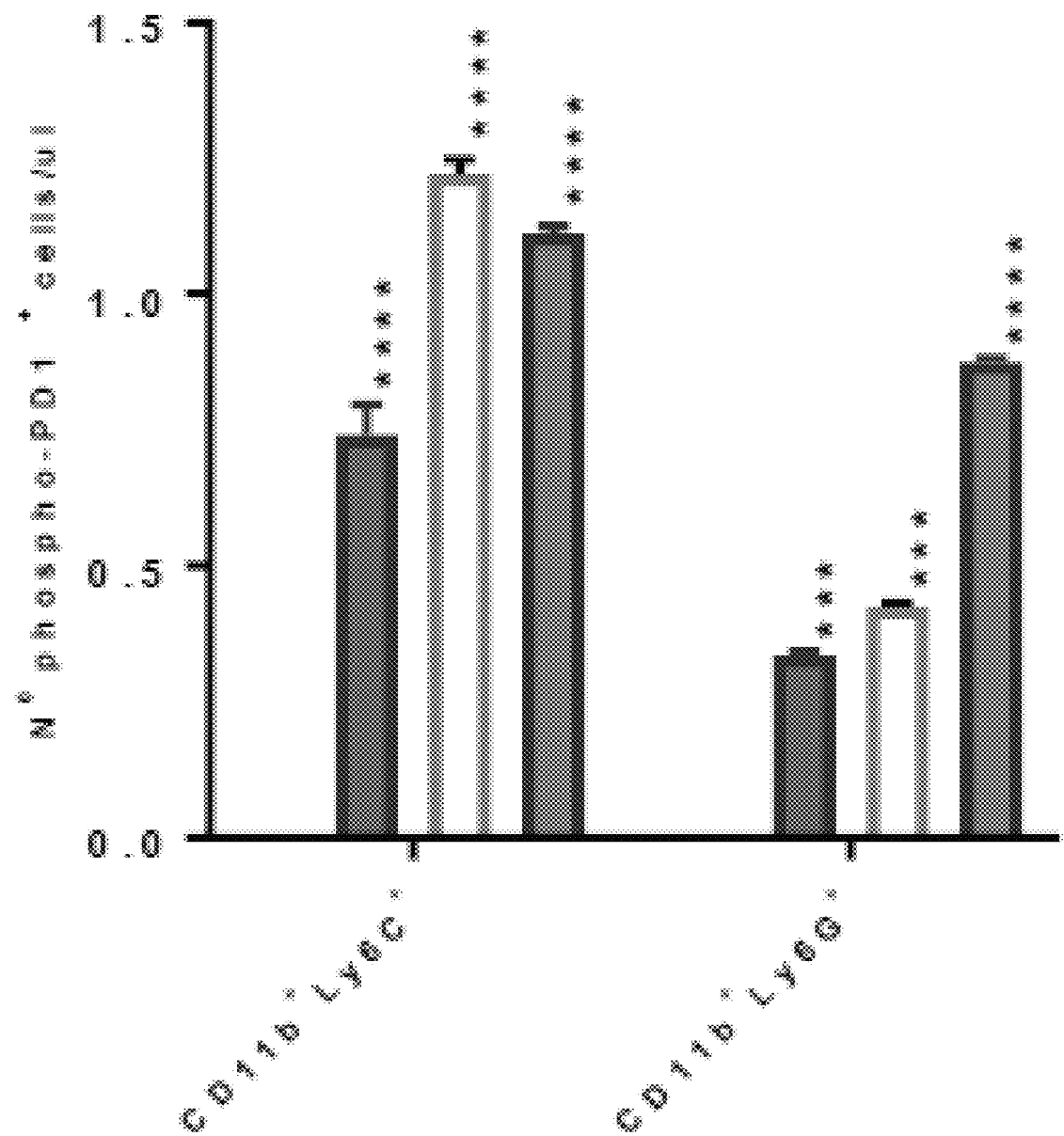
Figure 15F:
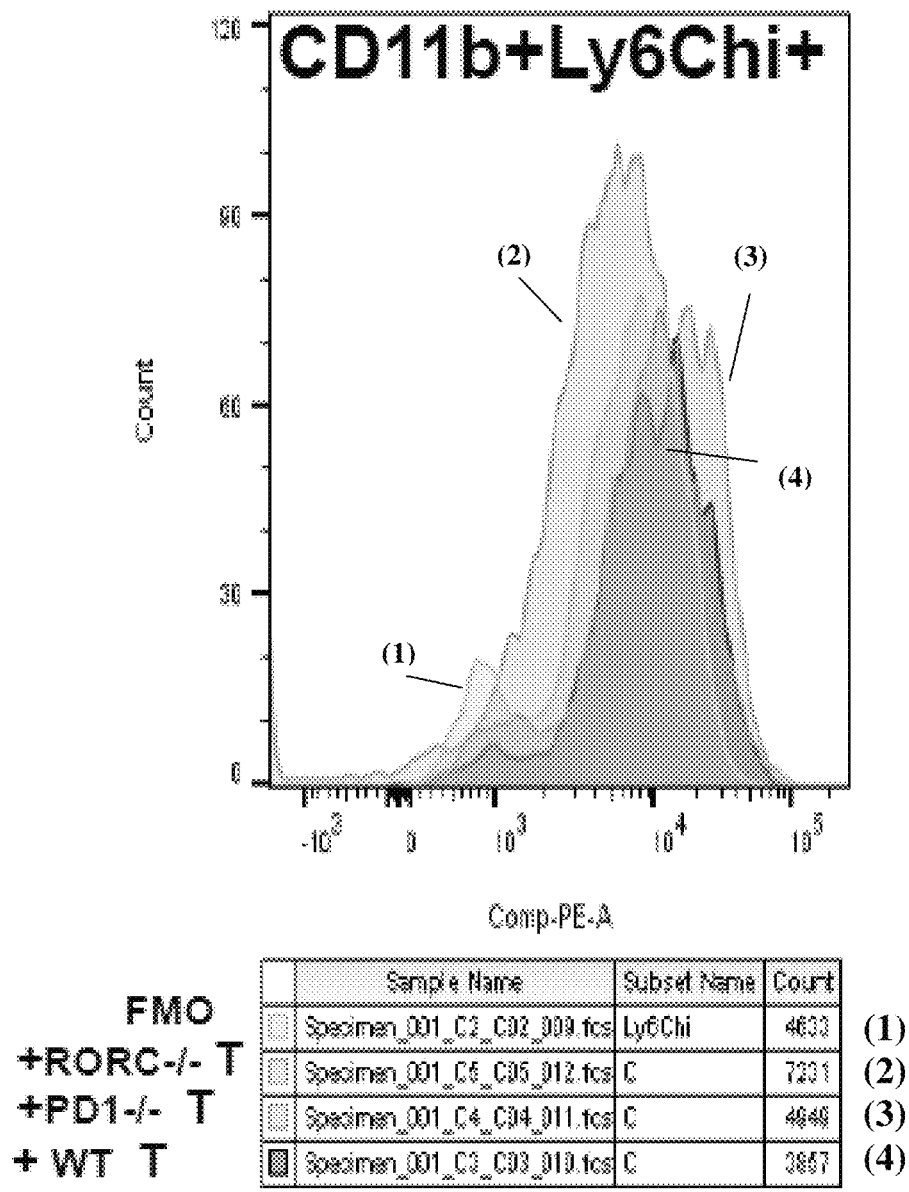

Moreover, it was determined that among T-cell receptor (TCR) proximal kinases, Fyn mediates the most potent phosphorylation of PD-1 Y248 (FIGS. 14A-14C). It was also determined that PD1 is highly phosphorylated in T cells that infiltrate tumors or reside in tumor-draining lymph nodes, but not in T cells isolated from non-tumor draining lymph nodes.

Also, it was determined that PD-1 blocked alters fate commitment of myeloid progenitors during tumor-mediated "emergency" myelopoiesis. The rapid change in hematopoietic output that occurs in response to immunologic stress is known as "emergency" myelopoiesis. This process is co-opted by tumors to enhance the generation of tumor-promoting myeloid cells, mostly undifferentiated myeloid-derived suppressor cells (MDSCs) and tumor-associated macrophages (TAMs). The myeloid compartment of tumor-bearing mice were analyzed and it was determined that myeloid cells express PD-1 and PD-L1. In particular, it was determined that PD-1 is expressed in myeloid cells isolated from bone marrow (FIGS. 15A-15F). Bone Marrow (BM) cells obtained from WT (B6) and RORC$^{-/-}$ mice were differentiated in the presence of GM-CSF, G-CSF, and IL-6 to myeloid-derived suppressor cells (MDSCs)-like myeloid cells. The expression of phospho-PD-1 in such BM-derived MDSCs-like cells were tested. Specifically, WT or RORC$^{-/-}$ BM-MDSCs-like cells were co-incubated with WT, PD-1', or RORC$^{-/-}$ T cells in the presence of anti-CD3/CD28 Ab for 4 days. Flow cytometry analysis were performed for gated CD11b+CD45+ MDSCs-like cells after 4 days of T cell co-incubation (FIGS. 15A-15F).

Using PD-1 knockout (KO) mice or wild-type (WT) mice treated with PD-1 blocking antibody in cancer-driven myelopoiesis experiments, a cell-switch fate from MDSCs to effector myeloid cells was determined. Culture of myeloid cells in vitro resulted in high levels of phosphorylated PD-1 specifically in myeloid cell subset characterized by high expression of Ly6C. Using myeloid cells from RORC1 deficient mice, it was observed that PD-1 phosphorylation in myeloid cells was preserved even when expression of RORC1, a transcription factor required for expansion of Ly6C hi myeloid cells, was abrogated. The expression and phosphorylation of PD-1 in myeloid cells required the presence and contact of T cells. PD-1 deletion or blockade, which impaired tumor growth and metastases, stimulated the differentiation of hematopoietic progenitor cells and resulted in increase of Ly6Chi monocytes and monocyte-derived DC (mo-DC). Abrogation of PD-1 signaling enhanced the maturation of MDSCs by inducing the lineage commitment transcription factors, IRF8, IRF4 and RORC1. IRF8 and IRF4 promote monocytes/macrophage and hinder granulocyte differentiation, whereas RORC1 is required for expansion of Ly6Chi monocytes and resolution of inflammation. These results reveal a role of the PD-1:PD-L1 pathway in the differentiation of myeloid progenitors, such as lineage-committed myeloid progenitors, to promote undifferentiated MDSCs and suppress effector mo-DCs. The switch of myeloid progenitor fate commitment is believed to be a key mechanism by which PD-1 blockade mediates anti-tumor function.

Taken together, these results indicate that PD-1 pathway activation can be measured using anti-phosphotyrosine PD-1 antibodies and that phosphorylation of Y248 in the ITSM of PD-1 is indicative of PD-1-mediated inhibitory function. Such antibodies allow the examination of the properties and identity of CD4+ and CD8+ human T cells that display constitutive expression of phosphorylated PD-1 in vivo without any experimental intervention to identify the molecular signature of phospho-PD-1+ T cells and analyze PD-1 phosphorylation in T cells as a physiologic event that occurs in vivo during engagement of the PD-1 receptor for prevention of autoimmunity.

The antibodies also allow confirmation of the believed correlation between phospho-PD-1 expression and other checkpoint inhibitors and/or costimulatory receptors, which engage signaling pathways parallel or merging with PD-1-mediated signals, such as through analysis of phospho-PD-1+ cells co-expressing such additional receptors display distinct functional and molecular properties as compared to those that express phospho-PD-1 alone. The expression and function of such cells can be studied in physiologic individuals and patients with cancer before and after treatment with checkpoint inhibitors.

In addition, the antibodies allow characterization of phospho-PD-1 expression in healthy human and mouse tissues, in tumor biopsies of patients with cancers which respond to PD-1-blocking immunotherapy, in patients with cancers in which PD-1-blocking immunotherapy is inefficient, and in tumor-bearing animal models, like mice, such as focusing on phospho-PD-1 expression in T cells and myeloid cells. It is believed that phospho-PD-1 expression in the appropriate microenvironments and cell types serves as an indicator of PD-1-mediated inhibitory signaling and, therefore, serves as a biomarker for selection of patients who will benefit from PD-1-based immunotherapy.

Moreover, the antibodies allow identification of PD-1: PD-L1 expression at early stages of myeloid cell differentiation from hematopoietic progenitors and determination of important role of this pathway in lineage fate commitment. For example, PD-1 phosphorylation during myeloid cell differentiation, an event that occurs in patients who receive hematopoietic stem cell transplantation, can be determined. In this patient group, it has been determined that myeloid cell engraftment and differentiation correlates with high levels of soluble PD-L1 in the patient's serum. It is believed that phospho-PD-1 expression in committed myeloid cell progenitors together with soluble PD-L1 levels serves as biomarkers indicating successful hematopoietic stem cell engraftment and differentiation after hematopoietic stem cell transplantation. These endpoints are believed to serve as indicators of engraftment versus graft failure and guide treatment decisions early after hematopoietic stem cell transplantation.

In addition, the role of phospho-PD-1 expression and function in autoimmune diseases is examined. It has been determined that phospho-PD-1 expression is detected in CD4+ and CD8+ T cells from the peripheral blood of healthy individuals. PD-1 expression and function is critical for maintenance of self-tolerance, whereas PD-1 polymorphisms have been identified in autoimmune diseases. For these reasons, it is believed that phospho-PD-1 serves as an indicator of self-tolerance and lacking or having low levels of phospho-PD-1 expression serves as a biomarker of autoimmunity. In this respect, phospho-PD-1 expression level is believed to serve as a biomarker of response to treatment, or lack of response, in patients with autoimmune diseases.

Example 4: Additional Monoclonal Antibodies (mAbs) that Detect Phosphorylation of the ITSM Domain of Human and Mouse PD-1

Additional mAbs that detect phosphorylation of the ITSM domain of human and mouse PD-1 were generated. Briefly, rabbit phospho-specific PD-1 antibodies were generated in rabbits and were screened against synthesized phospho-PD-1 peptides, PD-1 pITSM (KTPEPPVPCVPEQTE (pY) ATIVFPS) (SEQ ID NO: 142) and PD-1 pITIM (KEDP-SAVPVFSVD (pY) GELDFQWRE) (SEQ ID NO: 143). Peptide stocks were diluted in PBS 1× at a concentration 1 µg/ml and 100 µl/well was added. EIA/RIA high binding ELISA 96-well plates (Costar catalog #3361) were used for the experiments. The upper half part of the well plate was coated with the pITSM target peptide and the lower half part of the well plate was coated with the negative control pITIM peptide. The plate was incubated at 4° C. overnight. The plate was subsequently washed 4 times with wash buffer (PBS 1×, 0.05% TWEEN® 20 (polysorbate 20); 300 µl/well) followed by a blocking step (3% BSA in wash buffer; 200 µl/well blocking buffer) and incubation for 1 hour at 37° C. The plate was then washed 1 time with wash buffer (PBS 1×, 0.05% TWEEN® 20 (polysorbate 20); 300 µl/well) followed by addition of antibody supernatants (100 µl/well) in duplicate (i.e., 2 tests for binding to pITSM and 2 tests for binding on pITIM). Two wells were used for blanks by adding PBS 1× (100 µl/well) and 2 wells were used as negative controls by adding control supernatant from untransfected cells (100 µl/well). The plate was incubated at 4° C. overnight. The plate was subsequently washed 4 times with wash buffer (PBS 1×, 0.05% TWEEN® 20 (polysorbate 20); 300 µl/well) followed by addition of secondary antibody (AffiniPure™ Goat Anti-Rabbit IgG, Fc Fragment Specific (Jackson ImmunoResearch Labs, 111-035-046) diluted 1:30000 in 1% BSA in PBS 1× (100 µl/well). The plate was incubated for 30 minutes at 37° C. The plate was then washed 5 times with wash buffer (PBS 1×, 0.05% TWEEN® 20 (polysorbate 20); 300 µl/well) followed by addition of TMB reagent (GenScript Cat.No M00078; 100 µl/well). The plate was incubated 10-15 min at room temperature and the reaction as stopped by adding stop solution (1N HCl; 100 µl/well) followed by reading of absorbance at 415 nm against the blank values, which were set as zero, using a plate reader (SpectraMax® M5, Molecular Devices).

Figure 16:
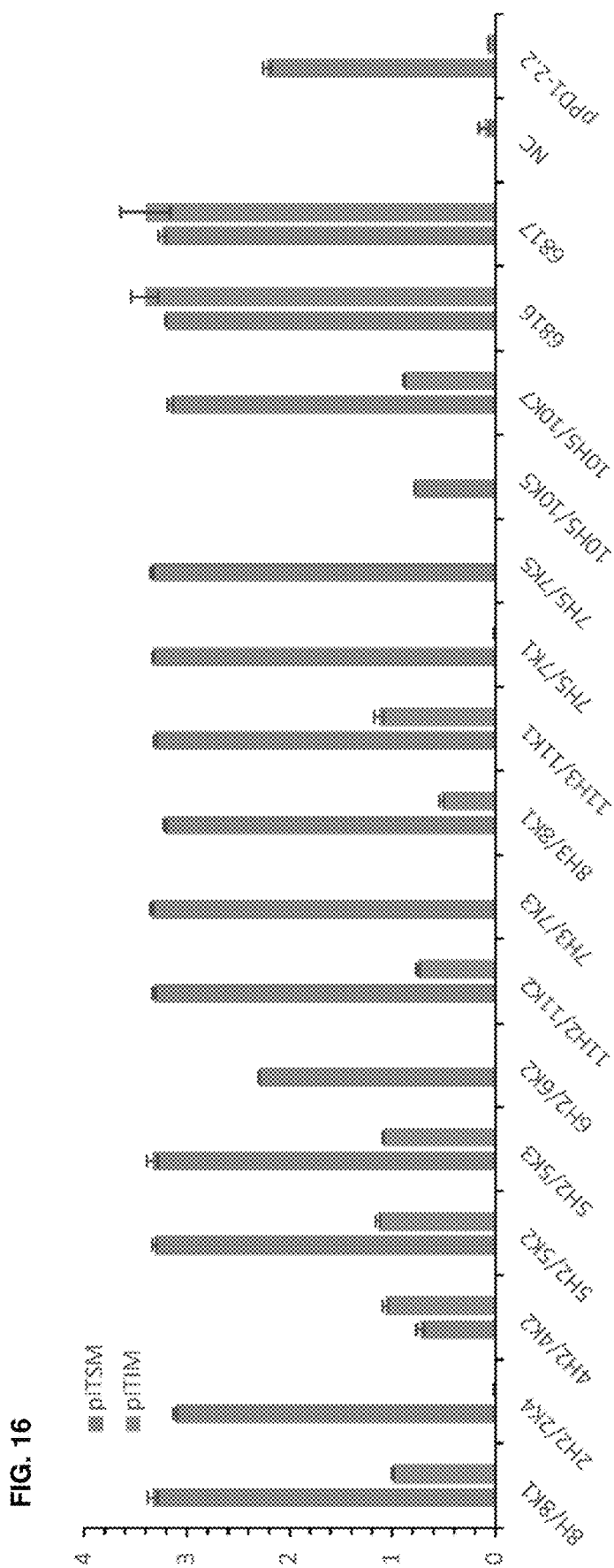
FIG. 16 shows binding results from rabbit anti-PD-1 phospho-peptide ELISA assays. The rabbit polyclonal anti-PD-1 pITSM antibody pPD1-2.2 was included as a positive control. Culture medium alone was used as a negative control (NC).

Sixteen candidate clones for production of antibody with specificity for the phosphorylated PD-1 ITSM Y248. As demonstrated in FIG. 16, six among the sixteen clones tested showed reactivity against PD-1 pITSM (KT-PEPPVPCVPEQTE(pY)ATIVFPS) (SEQ ID NO: 142) but have no reactivity against PD-1 pITIM (KEDP-SAVPVFSVD(pY)GELDFQWRE (SEQ ID NO: 143). Three clones (2H2/2K4, 6H2/6K2 and 7H5/7K1) were selected for further characterization and the variable domains of the light and heavy chain of each mAb was sequenced. The sequences are shown in Table 1 and FIG. 17.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of assessing the efficacy of a test agent for modulating PD-1 signaling, the method comprising:
  a) contacting a cell expressing PD-1 with a test agent; and
  b) determining the ability of the test agent to modulate the level of phosphorylated PD-1 using at least one monoclonal antibody, or antigen-binding fragment thereof, that binds to a phosphorylation site at tyrosine residue 248 of human PD-1, wherein the monoclonal, or antigen-binding fragment thereof, comprises:
  i) a light chain comprising CDR-L1 having the sequence of SEQ ID NO: 6, CDR-L2 having the sequence of SEQ ID NO: 9, and CDR-L3 having the sequence of SEQ ID NO: 12, and a heavy chain comprising CDR-H1 having the sequence of SEQ ID NO: 19, CDR-H2 having the sequence of SEQ ID NO: 22, and CDR-H3 having the sequence of SEQ ID NO: 25;
  ii) a light chain comprising CDR-L1 having the sequence of SEQ ID NO: 34, CDR-L2 having the sequence of SEQ ID NO: 38, and CDR-L3 having the sequence of SEQ ID NO: 43, and a heavy chain comprising CDR-H1 having the sequence of SEQ ID NO: 52, CDR-H2 having the sequence of SEQ ID NO: 56, and CDR-H3 having the sequence of SEQ ID NO: 60;
  iii) a light chain comprising CDR-L1 having the sequence of SEQ ID NO: 70, CDR-L2 having the sequence of SEQ ID NO: 74, and CDR-L3 having the sequence of SEQ ID NO: 78, and a heavy chain comprising CDR-H1 having the sequence of SEQ ID NO: 88, CDR-H2 having the sequence of SEQ ID NO: 92, and CDR-H3 having the sequence of SEQ ID NO: 96; or
  iv) a light chain comprising CDR-L1 having the sequence of SEQ ID NO: 106, CDR-L2 having the sequence of SEQ ID NO: 110, and CDR-L3 having the sequence of SEQ ID NO: 114, and a heavy chain comprising CDR-H1 having the sequence of SEQ ID NO: 124, CDR-H2 having the sequence of SEQ ID NO: 128, and CDR-H3 having the sequence of SEQ ID NO: 132;
  wherein a modulated level of phosphorylated PD-1 resulting from contacting with the test agent identifies the test agent as a modulator of PD-1 signaling.

2. The method of claim 1, wherein the monoclonal antibody, or antigen-binding fragment thereof, comprises a light chain comprising CDR-L1 having the sequence of SEQ ID NO: 6, CDR-L2 having the sequence of SEQ ID NO: 9, and CDR-L3 having the sequence of SEQ ID NO: 12, and a heavy chain comprising CDR-H1 having the sequence of SEQ ID NO: 19, CDR-H2 having the sequence of SEQ ID NO: 22, and CDR-H3 having the sequence of SEQ ID NO: 25.

3. The method of claim 2, wherein the monoclonal antibody, or antigen-binding fragment thereof, comprises a light chain comprising a sequence at least 90% identical to SEQ ID NO: 1 and a heavy chain comprising a sequence at least 90% identical to SEQ ID NO: 14.

4. The method of claim 3, wherein the monoclonal antibody, or antigen-binding fragment thereof, comprises a light chain comprising the sequence of SEQ ID NO: 1 and a heavy chain comprising the sequence of SEQ ID NO: 14.

5. The method of claim 1, wherein the monoclonal antibody, or antigen-binding fragment thereof, comprises a light chain comprising CDR-L1 having the sequence of SEQ ID NO: 34, CDR-L2 having the sequence of SEQ ID NO: 38, and CDR-L3 having the sequence of SEQ ID NO: 43, and a heavy chain comprising CDR-H1 having the sequence of SEQ ID NO: 52, CDR-H2 having the sequence of SEQ ID NO: 56, and CDR-H3 having the sequence of SEQ ID NO: 60.

6. The method of claim 5, wherein the monoclonal antibody, or antigen-binding fragment thereof, comprises a light chain comprising a sequence at least 90% identical to SEQ ID NO: 30 and a heavy chain comprising a sequence at least 90% identical to SEQ ID NO: 46.

7. The method of claim 6, wherein the monoclonal antibody, or antigen-binding fragment thereof, comprises a light chain comprising the sequence of SEQ ID NO: 30 and a heavy chain comprising the sequence of SEQ ID NO: 46.

8. The method of claim 1, wherein the monoclonal antibody, or antigen-binding fragment thereof, comprises a light chain comprising CDR-L1 having the sequence of SEQ ID NO: 70, CDR-L2 having the sequence of SEQ ID NO: 74, and CDR-L3 having the sequence of SEQ ID NO: 78, and a heavy chain comprising CDR-H1 having the sequence of SEQ ID NO: 88, CDR-H2 having the sequence of SEQ ID NO: 92, and CDR-H3 having the sequence of SEQ ID NO: 96.

9. The method of claim 8, wherein the monoclonal antibody, or antigen-binding fragment thereof, comprises a light chain comprising a sequence at least 90% identical to SEQ ID NO: 64 and a heavy chain comprising a sequence at least 90% identical to SEQ ID NO: 82.

10. The method of claim 9, wherein the monoclonal antibody, or antigen-binding fragment thereof, comprises a light chain comprising the sequence of SEQ ID NO: 64 and a heavy chain comprising the sequence of SEQ ID NO: 82.

11. The method of claim 1, wherein the monoclonal antibody, or antigen-binding fragment thereof, comprises a light chain comprising CDR-L1 having the sequence of SEQ ID NO: 106, CDR-L2 having the sequence of SEQ ID NO: 110, and CDR-L3 having the sequence of SEQ ID NO: 114, and a heavy chain comprising CDR-H1 having the sequence of SEQ ID NO: 124, CDR-H2 having the sequence of SEQ ID NO: 128, and CDR-H3 having the sequence of SEQ ID NO: 132.

12. The method of claim 11, wherein the monoclonal antibody, or antigen-binding fragment thereof, comprises a light chain comprising a sequence at least 90% identical to SEQ ID NO: 100 and a heavy chain comprising a sequence at least 90% identical to SEQ ID NO: 118.

13. The method of claim 12, wherein the monoclonal antibody, or antigen-binding fragment thereof, comprises a light chain comprising the sequence of SEQ ID NO: 100 and a heavy chain comprising the sequence of SEQ ID NO: 118.

14. The method of claim 1, wherein the monoclonal antibody, or antigen-binding fragment thereof, is chimeric, humanized, murine, or rabbit.

15. The method of claim 1, wherein the monoclonal antibody, or antigen-binding fragment thereof, is detectably labeled.

16. The method of claim 1, wherein the monoclonal antibody, or antigen-binding fragment thereof, comprises an effector domain.

17. The method of claim 1, wherein the monoclonal antibody, or antigen-binding fragment thereof, comprises an Fc domain.

18. The method of claim 1, wherein the antigen-binding fragment thereof, is selected from the group consisting of Fv, Fav, F (ab')2), Fab', dsFv, scFv, sc (Fv)2, and diabodies fragments.

* * * * *

```
                        SEQUENCE LISTING

Sequence total quantity: 147
SEQ ID NO: 1            moltype = AA   length = 127
FEATURE                 Location/Qualifiers
REGION                  1..127
                        note = /note="Description of Artificial Sequence: 6G12 vK
                          amino acidsequence"
source                  1..127
                        mol_type = protein
                        organism = synthetic construct
SEQUENCE: 1
MVSSAQFLVY MLLWLSGVDG DIVMTQSQKF MSTSVGDRVS VTCKASQNVG TNVAWYQQKP  60
GQSPKALIYS ASYRYSGVPD RFTGSGSGTD FTLTISNVHS EDLAEYFCQQ YNFYPLTFGA  120
GTKLELK                                                            127

SEQ ID NO: 2            moltype = DNA   length = 380
FEATURE                 Location/Qualifiers
misc_feature            1..380
                        note = /note="Description of Artificial Sequence: 6G12 vK
                          cDNA sequence"
source                  1..380
                        mol_type = other DNA
                        organism = synthetic construct
SEQUENCE: 2
atggtgtcct cagctcagtt ccttgtatac atgttgctgt ggttgtctgg tgttgatgga  60
gacattgtga tgacccagtc tcaaaaattc atgtccacat cagtaggaga cagggtcagc  120
gtcacctgca aggccagtca gaatgtgggt actaatgtag cctggtatca acagaaacca  180
gggcaatctc ctaaagcact gatttactcg gcatcctacc ggtacagtgg agtccctgat  240
cgcttcacag gcagtggatc gggacagatt tcactctcac catcagcaat gtgcactctg  300
aagacttggc agagtatttc tgtcagcaat ataacttcta tcctctcacg ttcggtgctg  360
ggaccaagct ggagctgaaa                                               380

SEQ ID NO: 3            moltype = DNA   length = 60
FEATURE                 Location/Qualifiers
misc_feature            1..60
                        note = /note="Description of Artificial Sequence: 6G12 vK
                          signal peptidecDNA sequence"
source                  1..60
                        mol_type = other DNA
                        organism = synthetic construct
SEQUENCE: 3
atggtgtcct cagctcagtt ccttgtatac atgttgctgt ggttgtctgg tgttgatgga  60

SEQ ID NO: 4            moltype = DNA   length = 69
FEATURE                 Location/Qualifiers
misc_feature            1..69
                        note = /note="Description of Artificial Sequence: 6G12 vK
                          framework 1cDNA sequence"
source                  1..69
                        mol_type = other DNA
                        organism = synthetic construct
SEQUENCE: 4
gacattgtga tgacccagtc tcaaaaattc atgtccacat cagtaggaga cagggtcagc  60
gtcacctgc                                                           69

SEQ ID NO: 5            moltype = DNA   length = 33
FEATURE                 Location/Qualifiers
misc_feature            1..33
                        note = /note="Description of Artificial Sequence: 6G12 vK
                          CDR-L1 cDNAsequence"
source                  1..33
                        mol_type = other DNA
                        organism = synthetic construct
SEQUENCE: 5
aaggccagtc agaatgtggg tactaatgta gcc                                33

SEQ ID NO: 6            moltype = AA   length = 11
FEATURE                 Location/Qualifiers
REGION                  1..11
                        note = /note="Description of Artificial Sequence: 6G12 vK
```

```
                         CDR-L1 aminoacid sequence"
source                   1..11
                         mol_type = protein
                         organism = synthetic construct
SEQUENCE: 6
KASQNVGTNV A                                                                 11

SEQ ID NO: 7             moltype = DNA   length = 45
FEATURE                  Location/Qualifiers
misc_feature             1..45
                         note = /note="Description of Artificial Sequence: 6G12 vK
                         framework 2cDNA sequence"
source                   1..45
                         mol_type = other DNA
                         organism = synthetic construct
SEQUENCE: 7
tggtatcaac agaaaccagg gcaatctcct aaagcactga tttac            45

SEQ ID NO: 8             moltype = DNA   length = 21
FEATURE                  Location/Qualifiers
misc_feature             1..21
                         note = /note="Description of Artificial Sequence: 6G12 vK
                         CDR-L2 cDNAsequence"
source                   1..21
                         mol_type = other DNA
                         organism = synthetic construct
SEQUENCE: 8
tcggcatcct accggtacag t                                                      21

SEQ ID NO: 9             moltype = AA    length = 7
FEATURE                  Location/Qualifiers
REGION                   1..7
                         note = /note="Description of Artificial Sequence: 6G12 vK
                         CDR-L2 aminoacid sequence"
source                   1..7
                         mol_type = protein
                         organism = synthetic construct
SEQUENCE: 9
SASYRYS                                                                       7

SEQ ID NO: 10            moltype = DNA   length = 96
FEATURE                  Location/Qualifiers
misc_feature             1..96
                         note = /note="Description of Artificial Sequence: 6G12 vK
                         framework 3cDNA sequence"
source                   1..96
                         mol_type = other DNA
                         organism = synthetic construct
SEQUENCE: 10
ggagtccctg atcgcttcac aggcagtgga tctgggacag atttcactct caccatcagc            60
aatgtgcact ctgaagactt ggcagagtat ttctgt                                      96

SEQ ID NO: 11            moltype = DNA   length = 27
FEATURE                  Location/Qualifiers
misc_feature             1..27
                         note = /note="Description of Artificial Sequence: 6G12 vK
                         CDR-L3 cDNAsequence"
source                   1..27
                         mol_type = other DNA
                         organism = synthetic construct
SEQUENCE: 11
cagcaatata acttctatcc tctcacg                                                27

SEQ ID NO: 12            moltype = AA    length = 9
FEATURE                  Location/Qualifiers
REGION                   1..9
                         note = /note="Description of Artificial Sequence: 6G12 vK
                         CDR-L3 aminoacid sequence"
source                   1..9
                         mol_type = protein
                         organism = synthetic construct
SEQUENCE: 12
QQYNFYPLT                                                                     9

SEQ ID NO: 13            moltype = DNA   length = 30
FEATURE                  Location/Qualifiers
misc_feature             1..30
                         note = /note="Description of Artificial Sequence: 6G12 vK J
                         segment cDNAsequence"
```

```
source                   1..30
                         mol_type = other DNA
                         organism = synthetic construct
SEQUENCE: 13
ttcggtgctg ggaccaagct ggagctgaaa                                      30

SEQ ID NO: 14            moltype = AA   length = 137
FEATURE                  Location/Qualifiers
REGION                   1..137
                         note = /note="Description of Artificial Sequence: 6G12 vH
                           amino acidsequence"
source                   1..137
                         mol_type = protein
                         organism = synthetic construct
SEQUENCE: 14
MLLGLKWVFF VVFYQGVRHE VQLVESGGGL VQPKGSLKLS CAASGFTFNT YAMNWVRQAP      60
GKGLEWVARI RSKSDNYATY YADSVKDRFT ISRDDSQSML YLQMNNLKTE DTAMYYCMRG     120
ITTVNVWGAG TTVTVSS                                                   137

SEQ ID NO: 15            moltype = DNA   length = 411
FEATURE                  Location/Qualifiers
misc_feature             1..411
                         note = /note="Description of Artificial Sequence: 6G12 vH
                           cDNA sequence"
source                   1..411
                         mol_type = other DNA
                         organism = synthetic construct
SEQUENCE: 15
atgctgttgg ggctgaagtg ggttttcttt gttgtttttt atcaaggtgt gcgtcatgag      60
gtgcagcttg ttgagtctgg tggaggattg gtgcagccta aagggtcatt gaaactctca     120
tgtgcagcct ctggattcac cttcaatacc tacgccatga actgggtccg ccaggctcca     180
ggaaagggtt tggaatgggt tgctcgcata agaagtaaaa gtgataatta tgcaacatat     240
tatgccgatt cagtgaaaga caggttcacc atctccagag atgattcaca agcatgctc      300
tatctgcaaa tgaacaactt gaaaactgag gacacagcca tgtattactg tatgaggggg     360
attactacgg tcaatgtctg gggcgcaggg accacggtca ccgtctcctc a              411

SEQ ID NO: 16            moltype = DNA   length = 57
FEATURE                  Location/Qualifiers
misc_feature             1..57
                         note = /note="Description of Artificial Sequence: 6G12 vH
                           signal peptidecDNA sequence"
source                   1..57
                         mol_type = other DNA
                         organism = synthetic construct
SEQUENCE: 16
atgctgttgg ggctgaagtg ggttttcttt gttgtttttt atcaaggtgt gcgtcat         57

SEQ ID NO: 17            moltype = DNA   length = 90
FEATURE                  Location/Qualifiers
misc_feature             1..90
                         note = /note="Description of Artificial Sequence: 6G12 vH
                           framework 1cDNA sequence"
source                   1..90
                         mol_type = other DNA
                         organism = synthetic construct
SEQUENCE: 17
gaggtgcagc ttgttgagtc tggtggagga ttggtgcagc ctaaagggtc attgaaactc      60
tcatgtgcag cctctggatt caccttcaat                                      90

SEQ ID NO: 18            moltype = DNA   length = 15
FEATURE                  Location/Qualifiers
misc_feature             1..15
                         note = /note="Description of Artificial Sequence: 6G12 vH
                           CDR-L1 cDNAsequence"
source                   1..15
                         mol_type = other DNA
                         organism = synthetic construct
SEQUENCE: 18
acctacgcca tgaac                                                      15

SEQ ID NO: 19            moltype = AA   length = 5
FEATURE                  Location/Qualifiers
REGION                   1..5
                         note = /note="Description of Artificial Sequence: 6G12 vH
                           CDR-L1 aminoacid sequence"
source                   1..5
                         mol_type = protein
                         organism = synthetic construct
SEQUENCE: 19
```

TYAMN                                                             5

SEQ ID NO: 20           moltype = DNA  length = 42
FEATURE                 Location/Qualifiers
misc_feature            1..42
                        note = /note="Description of Artificial Sequence: 6G12 vH
                          framework 2cDNA sequence"
source                  1..42
                        mol_type = other DNA
                        organism = synthetic construct
SEQUENCE: 20
tgggtccgcc aggctccagg aaagggtttg gaatgggttg ct                    42

SEQ ID NO: 21           moltype = DNA  length = 57
FEATURE                 Location/Qualifiers
misc_feature            1..57
                        note = /note="Description of Artificial Sequence: 6G12 vH
                          CDR-L2 cDNAsequence"
source                  1..57
                        mol_type = other DNA
                        organism = synthetic construct
SEQUENCE: 21
cgcataagaa gtaaaagtga taattatgca acatattatg ccgattcagt gaaagac    57

SEQ ID NO: 22           moltype = AA  length = 19
FEATURE                 Location/Qualifiers
REGION                  1..19
                        note = /note="Description of Artificial Sequence: 6G12 vH
                          CDR-L2 aminoacid sequence"
source                  1..19
                        mol_type = protein
                        organism = synthetic construct
SEQUENCE: 22
RIRSKSDNYA TYYADSVKD                                              19

SEQ ID NO: 23           moltype = DNA  length = 96
FEATURE                 Location/Qualifiers
misc_feature            1..96
                        note = /note="Description of Artificial Sequence: 6G12 vH
                          framework 3cDNA sequence"
source                  1..96
                        mol_type = other DNA
                        organism = synthetic construct
SEQUENCE: 23
aggttcacca tctccagaga tgattcacaa agcatgctct atctgcaaat gaacaacttg 60
aaaactgagg acacagccat gtattactgt atgagg                           96

SEQ ID NO: 24           moltype = DNA  length = 21
FEATURE                 Location/Qualifiers
misc_feature            1..21
                        note = /note="Description of Artificial Sequence: 6G12 vH
                          CDR-L3 cDNAsequence"
source                  1..21
                        mol_type = other DNA
                        organism = synthetic construct
SEQUENCE: 24
gggattacta cggtcaatgt c                                           21

SEQ ID NO: 25           moltype = AA  length = 7
FEATURE                 Location/Qualifiers
REGION                  1..7
                        note = /note="Description of Artificial Sequence: 6G12 vH
                          CDR-L3 aminoacid sequence"
source                  1..7
                        mol_type = protein
                        organism = synthetic construct
SEQUENCE: 25
GITTVNV                                                           7

SEQ ID NO: 26           moltype = DNA  length = 33
FEATURE                 Location/Qualifiers
misc_feature            1..33
                        note = /note="Description of Artificial Sequence: 6G12 vH J
                          segment cDNAsequence"
source                  1..33
                        mol_type = other DNA
                        organism = synthetic construct
SEQUENCE: 26
tggggcgcag ggaccacggt caccgtctcc tca                              33

```
SEQ ID NO: 27            moltype = DNA   length = 396
FEATURE                  Location/Qualifiers
misc_feature             1..396
                         note = /note="Description of Artificial Sequence: 2H2-2K4
                         vK cDNAsequence"
source                   1..396
                         mol_type = other DNA
                         organism = synthetic construct
SEQUENCE: 27
atggacacga gggcccccac tcagctgctg gggctcctgc tgctctggct cccaggtgcc    60
agatgtgatg ttgtgatgac ccagactcca tcttccgcgt ctgaacctgt gggaggcaca   120
gtcaccatca agtgccaggc cagtcagagc gttagtagta gattagcctg gtatcagcag   180
aaaccagggc agcctcccaa gctcctgatc tacaaggcat ccactctggc atctggggtc   240
ccatcgcggt tcaaaggcag tggatatggg acagagttca ctctcaccat cagcgacctg   300
gagtgtgccg atgctgccac ttactactgt caatgtactt atattgatag tacttatgga   360
aataatttcg gcggagggac cgaggtggtg gtcaaa                             396

SEQ ID NO: 28            moltype = AA   length = 132
FEATURE                  Location/Qualifiers
REGION                   1..132
                         note = /note="Description of Artificial Sequence: 2H2-2K4
                         vK amino acidsequence"
source                   1..132
                         mol_type = protein
                         organism = synthetic construct
SEQUENCE: 28
MDTRAPTQLL GLLLLWLPGA RCDVVMTQTP SSASEPVGGT VTIKCQASQS VSSRLAWYQQ    60
KPGQPPKLLI YKASTLASGV PSRFKGSGYG TEFTLTISDL ECADAATYYC QCTYIDSTYG   120
NNFGGGTEVV VK                                                       132

SEQ ID NO: 29            moltype = DNA   length = 66
FEATURE                  Location/Qualifiers
misc_feature             1..66
                         note = /note="Description of Artificial Sequence: 2H2-2K4
                         vK signalpeptide cDNA sequence"
source                   1..66
                         mol_type = other DNA
                         organism = synthetic construct
SEQUENCE: 29
atggacacga gggcccccac tcagctgctg gggctcctgc tgctctggct cccaggtgcc    60
agatgt                                                               66

SEQ ID NO: 30            moltype = AA   length = 22
FEATURE                  Location/Qualifiers
REGION                   1..22
                         note = /note="Description of Artificial Sequence: 2H2-2K4
                         vK signalpeptide amino acid sequence"
source                   1..22
                         mol_type = protein
                         organism = synthetic construct
SEQUENCE: 30
MDTRAPTQLL GLLLLWLPGA RC                                             22

SEQ ID NO: 31            moltype = DNA   length = 78
FEATURE                  Location/Qualifiers
misc_feature             1..78
                         note = /note="Description of Artificial Sequence: 2H2-2K4
                         vK framework 1cDNA sequence"
source                   1..78
                         mol_type = other DNA
                         organism = synthetic construct
SEQUENCE: 31
gatgttgtga tgacccagac tccatcttcc gcgtctgaac ctgtgggagg cacagtcacc    60
atcaagtgcc aggccagt                                                  78

SEQ ID NO: 32            moltype = AA   length = 26
FEATURE                  Location/Qualifiers
REGION                   1..26
                         note = /note="Description of Artificial Sequence: 2H2-2K4
                         vK framework 1amino acid sequence"
source                   1..26
                         mol_type = protein
                         organism = synthetic construct
SEQUENCE: 32
DVVMTQTPSS ASEPVGGTVT IKCQAS                                         26

SEQ ID NO: 33            moltype = DNA   length = 18
FEATURE                  Location/Qualifiers
```

```
misc_feature            1..18
                        note = /note="Description of Artificial Sequence: 2H2-2K4
                         vK CDR-L1 cDNAsequence"
source                  1..18
                        mol_type = other DNA
                        organism = synthetic construct
SEQUENCE: 33
cagagcgtta gtagtaga                                                         18

SEQ ID NO: 34           moltype = AA   length = 6
FEATURE                 Location/Qualifiers
REGION                  1..6
                        note = /note="Description of Artificial Sequence: 2H2-2K4
                         vK CDR-L1amino acid sequence"
source                  1..6
                        mol_type = protein
                        organism = synthetic construct
SEQUENCE: 34
QSVSSR                                                                       6

SEQ ID NO: 35           moltype = DNA   length = 51
FEATURE                 Location/Qualifiers
misc_feature            1..51
                        note = /note="Description of Artificial Sequence: 2H2-2K4
                         vK framework 2cDNA sequence"
source                  1..51
                        mol_type = other DNA
                        organism = synthetic construct
SEQUENCE: 35
ttagcctggt atcagcagaa accagggcag cctcccaagc tcctgatcta c                    51

SEQ ID NO: 36           moltype = AA   length = 17
FEATURE                 Location/Qualifiers
REGION                  1..17
                        note = /note="Description of Artificial Sequence: 2H2-2K4
                         vK framework 2amino acid sequence"
source                  1..17
                        mol_type = protein
                        organism = synthetic construct
SEQUENCE: 36
LAWYQQKPGQ PPKLLIY                                                          17

SEQ ID NO: 37           moltype =    length =
SEQUENCE: 37
000

SEQ ID NO: 38           moltype =    length =
SEQUENCE: 38
000

SEQ ID NO: 39           moltype = DNA   length = 108
FEATURE                 Location/Qualifiers
misc_feature            1..108
                        note = /note="Description of Artificial Sequence: 2H2-2K4
                         vK framework 3cDNA sequence"
source                  1..108
                        mol_type = other DNA
                        organism = synthetic construct
SEQUENCE: 39
actctggcat ctggggtccc atcgcggttc aaaggcagtg gatatgggac agagttcact           60
ctcaccatca gcgacctgga gtgtgccgat gctgccactt actactgt                       108

SEQ ID NO: 40           moltype = AA   length = 36
FEATURE                 Location/Qualifiers
REGION                  1..36
                        note = /note="Description of Artificial Sequence: 2H2-2K4
                         vK framework 3amino acid sequence"
source                  1..36
                        mol_type = protein
                        organism = synthetic construct
SEQUENCE: 40
TLASGVPSRF KGSGYGTEFT LTISDLECAD AATYYC                                     36

SEQ ID NO: 41           moltype = DNA   length = 36
FEATURE                 Location/Qualifiers
misc_feature            1..36
                        note = /note="Description of Artificial Sequence: 2H2-2K4
                         vK CDR-L3 cDNAsequence"
source                  1..36
```

```
                        mol_type = other DNA
                        organism = synthetic construct
SEQUENCE: 41
caatgtactt atattgatag tacttatgga aataat                              36

SEQ ID NO: 42           moltype = AA  length = 12
FEATURE                 Location/Qualifiers
REGION                  1..12
                        note = /note="Description of Artificial Sequence: 2H2-2K4
                        vK CDR-L3amino acid sequence"
source                  1..12
                        mol_type = protein
                        organism = synthetic construct
SEQUENCE: 42
QCTYIDSTYG NN                                                        12

SEQ ID NO: 43           moltype = DNA  length = 30
FEATURE                 Location/Qualifiers
misc_feature            1..30
                        note = /note="Description of Artificial Sequence: 2H2-2K4
                        vK J segmentcDNA sequence"
source                  1..30
                        mol_type = other DNA
                        organism = synthetic construct
SEQUENCE: 43
ttcggcggag ggaccgaggt ggtggtcaaa                                     30

SEQ ID NO: 44           moltype = AA  length = 10
FEATURE                 Location/Qualifiers
REGION                  1..10
                        note = /note="Description of Artificial Sequence: 2H2-2K4
                        vK J segmentamino acid sequence"
source                  1..10
                        mol_type = protein
                        organism = synthetic construct
SEQUENCE: 44
FGGGTEVVVK                                                           10

SEQ ID NO: 45           moltype = DNA  length = 417
FEATURE                 Location/Qualifiers
misc_feature            1..417
                        note = /note="Description of Artificial Sequence: 2H2-2K4
                        vH cDNAsequence"
source                  1..417
                        mol_type = other DNA
                        organism = synthetic construct
SEQUENCE: 45
atggagactg ggctgcgctg gcttctcctg gtcgctgtgc tcaaaggtgt ccagtgtcag    60
tcgttggagg agtccggggg agacctggtc aagcctgggg catccctgac actcacctgc   120
aaagcctctg gattctcctt cagtggcagc taccacatgt gctgggtccg ccaggctcca   180
gggaagggc tggagtggat cgcacacatc tatgttggta gtagtggtgg cacttactac   240
gcgagctggg cgaaaggccg attcgccatc tccaaaacct cgtcgaccac ggtgactctg   300
caaatgacca gtctgacagc cgcggacacg gccaccatt tctgtgcgag aagggatact   360
ggtgggacca gtgcttatgc cttgtggggc cagggcaccc tggtcaccgt ctcgagc     417

SEQ ID NO: 46           moltype = AA  length = 139
FEATURE                 Location/Qualifiers
REGION                  1..139
                        note = /note="Description of Artificial Sequence: 2H2-2K4
                        vH amino acidsequence"
source                  1..139
                        mol_type = protein
                        organism = synthetic construct
SEQUENCE: 46
METGLRWLLL VAVLKGVQCQ SLEESGGDLV KPGASLTLTC KASGFSFSGS YHMCWVRQAP    60
GKGLEWIAHI YVGSSGGTYY ASWAKGRFAI SKTSSTTVTL QMTSLAADT ATYFCARRDT   120
GGTSAYALWG QGTLVTVSS                                                139

SEQ ID NO: 47           moltype = DNA  length = 57
FEATURE                 Location/Qualifiers
misc_feature            1..57
                        note = /note="Description of Artificial Sequence: 2H2-2K4
                        vH signalpeptide cDNA sequence"
source                  1..57
                        mol_type = other DNA
                        organism = synthetic construct
SEQUENCE: 47
atggagactg ggctgcgctg gcttctcctg gtcgctgtgc tcaaaggtgt ccagtgt       57
```

```
SEQ ID NO: 48            moltype = AA   length = 19
FEATURE                  Location/Qualifiers
REGION                   1..19
                         note = /note="Description of Artificial Sequence: 2H2-2K4
                         vH signalpeptide amino acid sequence"
source                   1..19
                         mol_type = protein
                         organism = synthetic construct
SEQUENCE: 48
METGLRWLLL VAVLKGVQC                                                       19

SEQ ID NO: 49            moltype = DNA   length = 72
FEATURE                  Location/Qualifiers
misc_feature             1..72
                         note = /note="Description of Artificial Sequence: 2H2-2K4
                         vH framework 1cDNA sequence"
source                   1..72
                         mol_type = other DNA
                         organism = synthetic construct
SEQUENCE: 49
cagtcgttgg aggagtccgg gggagacctg gtcaagcctg ggcatccct gacactcacc    60
tgcaaagcct ct                                                       72

SEQ ID NO: 50            moltype = AA   length = 24
FEATURE                  Location/Qualifiers
REGION                   1..24
                         note = /note="Description of Artificial Sequence: 2H2-2K4
                         vH framework 1amino acid sequence"
source                   1..24
                         mol_type = protein
                         organism = synthetic construct
SEQUENCE: 50
QSLEESGGDL VKPGASLTLT CKAS                                                 24

SEQ ID NO: 51            moltype = DNA   length = 27
FEATURE                  Location/Qualifiers
misc_feature             1..27
                         note = /note="Description of Artificial Sequence: 2H2-2K4
                         vH CDR-H1 cDNAsequence"
source                   1..27
                         mol_type = other DNA
                         organism = synthetic construct
SEQUENCE: 51
ggattctcct tcagtggcag ctaccac                                       27

SEQ ID NO: 52            moltype = AA   length = 9
FEATURE                  Location/Qualifiers
REGION                   1..9
                         note = /note="Description of Artificial Sequence: 2H2-2K4
                         vH CDR-H1amino acid sequence"
source                   1..9
                         mol_type = protein
                         organism = synthetic construct
SEQUENCE: 52
GFSFSGSYH                                                                   9

SEQ ID NO: 53            moltype = DNA   length = 51
FEATURE                  Location/Qualifiers
misc_feature             1..51
                         note = /note="Description of Artificial Sequence: 2H2-2K4
                         vH framework 2cDNA sequence"
source                   1..51
                         mol_type = other DNA
                         organism = synthetic construct
SEQUENCE: 53
atgtgctggg tccgccaggc tccagggaag gggctggagt ggatcgcaca c            51

SEQ ID NO: 54            moltype = AA   length = 17
FEATURE                  Location/Qualifiers
REGION                   1..17
                         note = /note="Description of Artificial Sequence: 2H2-2K4
                         vH framework 2amino acid sequence"
source                   1..17
                         mol_type = protein
                         organism = synthetic construct
SEQUENCE: 54
MCWVRQAPGK GLEWIAH                                                         17

SEQ ID NO: 55            moltype = DNA   length = 27
```

```
FEATURE                 Location/Qualifiers
misc_feature            1..27
                        note = /note="Description of Artificial Sequence: 2H2-2K4
                          vH CDR-H2 cDNAsequence"
source                  1..27
                        mol_type = other DNA
                        organism = synthetic construct
SEQUENCE: 55
atctatgttg gtagtagtgg tggcact                                              27

SEQ ID NO: 56           moltype = AA  length = 9
FEATURE                 Location/Qualifiers
REGION                  1..9
                        note = /note="Description of Artificial Sequence: 2H2-2K4
                          vH CDR-H2amino acid sequence"
source                  1..9
                        mol_type = protein
                        organism = synthetic construct
SEQUENCE: 56
IYVGSSGGT                                                                   9

SEQ ID NO: 57           moltype = DNA  length = 111
FEATURE                 Location/Qualifiers
misc_feature            1..111
                        note = /note="Description of Artificial Sequence: 2H2-2K4
                          vH framework 3cDNA sequence"
source                  1..111
                        mol_type = other DNA
                        organism = synthetic construct
SEQUENCE: 57
tactacgcga gctgggcgaa aggccgattc gccatctcca aaacctcgtc gaccacggtg          60
actctgcaaa tgaccagtct gacagccgcg gacacggcca cctatttctg t                 111

SEQ ID NO: 58           moltype = AA  length = 37
FEATURE                 Location/Qualifiers
REGION                  1..37
                        note = /note="Description of Artificial Sequence: 2H2-2K4
                          vH framework 3amino acid sequence"
source                  1..37
                        mol_type = protein
                        organism = synthetic construct
SEQUENCE: 58
YYASWAKGRF AISKTSSTTV TLQMTSLTAA DTATYFC                                    37

SEQ ID NO: 59           moltype = DNA  length = 39
FEATURE                 Location/Qualifiers
misc_feature            1..39
                        note = /note="Description of Artificial Sequence: 2H2-2K4
                          vH CDR-H3 cDNAsequence"
source                  1..39
                        mol_type = other DNA
                        organism = synthetic construct
SEQUENCE: 59
gcgagaaggg atactggtgg gaccagtgct tatgccttg                                  39

SEQ ID NO: 60           moltype = AA  length = 13
FEATURE                 Location/Qualifiers
REGION                  1..13
                        note = /note="Description of Artificial Sequence: 2H2-2K4
                          vH CDR-H3amino acid sequence"
source                  1..13
                        mol_type = protein
                        organism = synthetic construct
SEQUENCE: 60
ARRDTGGTSA YAL                                                              13

SEQ ID NO: 61           moltype = DNA  length = 33
FEATURE                 Location/Qualifiers
misc_feature            1..33
                        note = /note="Description of Artificial Sequence: 2H2-2K4
                          vH J segmentcDNA sequence"
source                  1..33
                        mol_type = other DNA
                        organism = synthetic construct
SEQUENCE: 61
tggggccagg gcaccctggt caccgtctcg agc                                        33

SEQ ID NO: 62           moltype = AA  length = 11
FEATURE                 Location/Qualifiers
```

```
REGION                   1..11
                         note = /note="Description of Artificial Sequence: 2H2-2K4
                          vH J segmentamino acid sequence"
source                   1..11
                         mol_type = protein
                         organism = synthetic construct
SEQUENCE: 62
WGQGTLVTVS S                                                              11

SEQ ID NO: 63            moltype = DNA  length = 396
FEATURE                  Location/Qualifiers
misc_feature             1..396
                         note = /note="Description of Artificial Sequence: 6H2-6K2
                          vK cDNAsequence"
source                   1..396
                         mol_type = other DNA
                         organism = synthetic construct
SEQUENCE: 63
atggacacga gggcccccac tcagctgctg gggctcctgc tgctctggct cccaggtgcc    60
acatttgcca tcaaaatgac ccagactcca tcctccgcgg aggcagctgt gggaggcaca   120
atcaccatca attgtcaggc cagtcagagc attagtagta gcttagcctg gtatcagcag   180
aaaccagggc agcctcccaa actcctgatc tacaaggctt ccactctggc atctggggtc   240
ccgtcgcggt tcagtggcag tagatctggg acacagttca ctctcaccat cagcggcgtg   300
cagtgtgacg atgctgccac ttactactgt caacagggtt ggagtggtga taatgttgat   360
aatatttttg gcggagggac cgaggtggtg gtcaaa                             396

SEQ ID NO: 64            moltype = AA  length = 132
FEATURE                  Location/Qualifiers
REGION                   1..132
                         note = /note="Description of Artificial Sequence: 6H2-6K2
                          vK amino acidsequence"
source                   1..132
                         mol_type = protein
                         organism = synthetic construct
SEQUENCE: 64
MDTRAPTQLL GLLLLWLPGA TFAIKMTQTP SSAEAAVGGT ITINCQASQS ISSSLAWYQQ    60
KPGQPPKLLI YKASTLASGV PSRFSGSRSG TQFTLTISGV QCDDAATYYC QQGWSGDNVD   120
NIFGGGTEVV VK                                                       132

SEQ ID NO: 65            moltype = DNA  length = 66
FEATURE                  Location/Qualifiers
misc_feature             1..66
                         note = /note="Description of Artificial Sequence: 6H2-6K2
                          vK signalpeptide cDNA sequence"
source                   1..66
                         mol_type = other DNA
                         organism = synthetic construct
SEQUENCE: 65
atggacacga gggcccccac tcagctgctg gggctcctgc tgctctggct cccaggtgcc    60
acattt                                                               66

SEQ ID NO: 66            moltype = AA  length = 22
FEATURE                  Location/Qualifiers
REGION                   1..22
                         note = /note="Description of Artificial Sequence: 6H2-6K2
                          vK signalpeptide amino acid sequence"
source                   1..22
                         mol_type = protein
                         organism = synthetic construct
SEQUENCE: 66
MDTRAPTQLL GLLLLWLPGA TF                                             22

SEQ ID NO: 67            moltype = DNA  length = 78
FEATURE                  Location/Qualifiers
misc_feature             1..78
                         note = /note="Description of Artificial Sequence: 6H2-6K2
                          vK framework 1cDNA sequence"
source                   1..78
                         mol_type = other DNA
                         organism = synthetic construct
SEQUENCE: 67
gccatcaaaa tgacccagac tccatcctcc gcggaggcag ctgtgggagg cacaatcacc    60
atcaattgtc aggccagt                                                  78

SEQ ID NO: 68            moltype = AA  length = 26
FEATURE                  Location/Qualifiers
REGION                   1..26
                         note = /note="Description of Artificial Sequence: 6H2-6K2
                          vK framework 1amino acid sequence"
```

```
source                  1..26
                        mol_type = protein
                        organism = synthetic construct
SEQUENCE: 68
AIKMTQTPSS AEAAVGGTIT INCQAS                                          26

SEQ ID NO: 69           moltype = DNA  length = 18
FEATURE                 Location/Qualifiers
misc_feature            1..18
                        note = /note="Description of Artificial Sequence: 6H2-6K2
                        vK CDR-L1 cDNAsequence"
source                  1..18
                        mol_type = other DNA
                        organism = synthetic construct
SEQUENCE: 69
cagagcatta gtagtagc                                                   18

SEQ ID NO: 70           moltype = AA  length = 6
FEATURE                 Location/Qualifiers
REGION                  1..6
                        note = /note="Description of Artificial Sequence: 6H2-6K2
                        vK CDR-L1amino acid sequence"
source                  1..6
                        mol_type = protein
                        organism = synthetic construct
SEQUENCE: 70
QSISSS                                                                6

SEQ ID NO: 71           moltype = DNA  length = 51
FEATURE                 Location/Qualifiers
misc_feature            1..51
                        note = /note="Description of Artificial Sequence: 6H2-6K2
                        vK framework 2cDNA sequence"
source                  1..51
                        mol_type = other DNA
                        organism = synthetic construct
SEQUENCE: 71
ttagcctggt atcagcagaa accagggcag cctcccaaac tcctgatcta c              51

SEQ ID NO: 72           moltype = AA  length = 17
FEATURE                 Location/Qualifiers
REGION                  1..17
                        note = /note="Description of Artificial Sequence: 6H2-6K2
                        vK framework 2amino acid sequence"
source                  1..17
                        mol_type = protein
                        organism = synthetic construct
SEQUENCE: 72
LAWYQQKPGQ PPKLLIY                                                    17

SEQ ID NO: 73           moltype =   length =
SEQUENCE: 73
000

SEQ ID NO: 74           moltype =   length =
SEQUENCE: 74
000

SEQ ID NO: 75           moltype = DNA  length = 108
FEATURE                 Location/Qualifiers
misc_feature            1..108
                        note = /note="Description of Artificial Sequence: 6H2-6K2
                        vK framework 3cDNA sequence"
source                  1..108
                        mol_type = other DNA
                        organism = synthetic construct
SEQUENCE: 75
actctggcat ctggggtccc gtcgcggttc agtggcagta gatctgggac acagttcact     60
ctcaccatca gcggcgtgca gtgtgacgat gctgccactt actactgt                 108

SEQ ID NO: 76           moltype = AA  length = 36
FEATURE                 Location/Qualifiers
REGION                  1..36
                        note = /note="Description of Artificial Sequence: 6H2-6K2
                        vK framework 3amino acid sequence"
source                  1..36
                        mol_type = protein
                        organism = synthetic construct
SEQUENCE: 76
```

```
TLASGVPSRF SGSRSGTQFT LTISGVQCDD AATYYC                           36

SEQ ID NO: 77           moltype = DNA   length = 36
FEATURE                 Location/Qualifiers
misc_feature            1..36
                        note = /note="Description of Artificial Sequence: 6H2-6K2
                        vK CDR-L3 cDNAsequence"
source                  1..36
                        mol_type = other DNA
                        organism = synthetic construct
SEQUENCE: 77
caacagggtt ggagtggtga taatgttgat aatatt                           36

SEQ ID NO: 78           moltype = AA   length = 12
FEATURE                 Location/Qualifiers
REGION                  1..12
                        note = /note="Description of Artificial Sequence: 6H2-6K2
                        vK CDR-L3amino acid sequence"
source                  1..12
                        mol_type = protein
                        organism = synthetic construct
SEQUENCE: 78
QQGWSGDNVD NI                                                     12

SEQ ID NO: 79           moltype = DNA   length = 30
FEATURE                 Location/Qualifiers
misc_feature            1..30
                        note = /note="Description of Artificial Sequence: 6H2-6K2
                        vK J segmentcDNA sequence"
source                  1..30
                        mol_type = other DNA
                        organism = synthetic construct
SEQUENCE: 79
tttggcggag ggaccgaggt ggtggtcaaa                                  30

SEQ ID NO: 80           moltype = AA   length = 10
FEATURE                 Location/Qualifiers
REGION                  1..10
                        note = /note="Description of Artificial Sequence: 6H2-6K2
                        vK J segmentamino acid sequence"
source                  1..10
                        mol_type = protein
                        organism = synthetic construct
SEQUENCE: 80
FGGGTEVVVK                                                        10

SEQ ID NO: 81           moltype = DNA   length = 408
FEATURE                 Location/Qualifiers
misc_feature            1..408
                        note = /note="Description of Artificial Sequence: 6H2-6K2
                        vH cDNAsequence"
source                  1..408
                        mol_type = other DNA
                        organism = synthetic construct
SEQUENCE: 81
atggagactg ggctgcgctg gcttctcctg gtcgctgtgc tcaaaggtgt ccagtgtcag   60
tcggtggagg agtccggggg tcgcctggtc acgcctggga caccctgac actcacctgc   120
acagtctctg gaatcgacct caattactat gcaatgggct gggtccgcca ggctccaggg   180
aagggggctgg aatacatcgg atggattaaa agtagtggta gcgcatacta tcgcgaggtgg   240
gtgaatggtc gattcaccat ctccaaaacc tcgtcgaca cggtggatct gaaaatgact   300
agtccgacaa ccgaggacac ggccacctat ttctgtgcca gagatggcca caatataatt   360
gaatattatg atttgtgggg ccagggcacc ctggtcaccg tctcgagc               408

SEQ ID NO: 82           moltype = AA   length = 136
FEATURE                 Location/Qualifiers
REGION                  1..136
                        note = /note="Description of Artificial Sequence: 6H2-6K2
                        vH amino acidsequence"
source                  1..136
                        mol_type = protein
                        organism = synthetic construct
SEQUENCE: 82
METGLRWLLL VAVLKGVQCQ SVEESGGRLV TPGTPLTLTC TVSGIDLNYY AMGWVRQAPG   60
KGLEYIGWIK SSGSAYYARW VNGRFTISKT SSTTVDLKMT SPTTEDTATY FCARDGHNII   120
EYYDLWGQGT LVTVSS                                                 136

SEQ ID NO: 83           moltype = DNA   length = 51
FEATURE                 Location/Qualifiers
misc_feature            1..51
```

```
                        note = /note="Description of Artificial Sequence: 6H2-6K2
                            vH signalpeptide cDNA sequence"
source                  1..51
                        mol_type = other DNA
                        organism = synthetic construct
SEQUENCE: 83
atggagactg ggctgcgctg gcttctcctg gtcgctgtgc tcaaaggtgt c            51

SEQ ID NO: 84           moltype = AA   length = 17
FEATURE                 Location/Qualifiers
REGION                  1..17
                        note = /note="Description of Artificial Sequence: 6H2-6K2
                            vH signalpeptide amino acid sequence"
source                  1..17
                        mol_type = protein
                        organism = synthetic construct
SEQUENCE: 84
METGLRWLLL VAVLKGV                                                  17

SEQ ID NO: 85           moltype = DNA   length = 78
FEATURE                 Location/Qualifiers
misc_feature            1..78
                        note = /note="Description of Artificial Sequence: 6H2-6K2
                            vH framework 1cDNA sequence"
source                  1..78
                        mol_type = other DNA
                        organism = synthetic construct
SEQUENCE: 85
cagtgtcagt cggtggagga gtccgggggt cgcctggtca cgcctgggac acccctgaca   60
ctcacctgca cagtctct                                                 78

SEQ ID NO: 86           moltype = AA   length = 26
FEATURE                 Location/Qualifiers
REGION                  1..26
                        note = /note="Description of Artificial Sequence: 6H2-6K2
                            vH framework 1amino acid sequence"
source                  1..26
                        mol_type = protein
                        organism = synthetic construct
SEQUENCE: 86
QCQSVEESGG RLVTPGTPLT LTCTVS                                        26

SEQ ID NO: 87           moltype = DNA   length = 24
FEATURE                 Location/Qualifiers
misc_feature            1..24
                        note = /note="Description of Artificial Sequence: 6H2-6K2
                            vH CDR-H1 cDNAsequence"
source                  1..24
                        mol_type = other DNA
                        organism = synthetic construct
SEQUENCE: 87
ggaatcgacc tcaattacta tgca                                          24

SEQ ID NO: 88           moltype = AA   length = 8
FEATURE                 Location/Qualifiers
REGION                  1..8
                        note = /note="Description of Artificial Sequence: 6H2-6K2
                            vH CDR-H1amino acid sequence"
source                  1..8
                        mol_type = protein
                        organism = synthetic construct
SEQUENCE: 88
GIDLNYYA                                                            8

SEQ ID NO: 89           moltype = DNA   length = 51
FEATURE                 Location/Qualifiers
misc_feature            1..51
                        note = /note="Description of Artificial Sequence: 6H2-6K2
                            vH framework 2cDNA sequence"
source                  1..51
                        mol_type = other DNA
                        organism = synthetic construct
SEQUENCE: 89
atgggctggg tccgccaggc tccagggaag gggctggaat acatcggatg g            51

SEQ ID NO: 90           moltype = AA   length = 17
FEATURE                 Location/Qualifiers
REGION                  1..17
                        note = /note="Description of Artificial Sequence: 6H2-6K2
```

```
                        vH framework 2amino acid sequence"
source                  1..17
                        mol_type = protein
                        organism = synthetic construct
SEQUENCE: 90
MGWVRQAPGK GLEYIGW                                                       17

SEQ ID NO: 91           moltype = DNA  length = 21
FEATURE                 Location/Qualifiers
misc_feature            1..21
                        note = /note="Description of Artificial Sequence: 6H2-6K2
                        vH CDR-H2 cDNAsequence"
source                  1..21
                        mol_type = other DNA
                        organism = synthetic construct
SEQUENCE: 91
attaaaagta gtggtagcgc a                                                  21

SEQ ID NO: 92           moltype = AA  length = 7
FEATURE                 Location/Qualifiers
REGION                  1..7
                        note = /note="Description of Artificial Sequence: 6H2-6K2
                        vH CDR-H2amino acid sequence"
source                  1..7
                        mol_type = protein
                        organism = synthetic construct
SEQUENCE: 92
IKSSGSA                                                                   7

SEQ ID NO: 93           moltype = DNA  length = 111
FEATURE                 Location/Qualifiers
misc_feature            1..111
                        note = /note="Description of Artificial Sequence: 6H2-6K2
                        vH framework 3cDNA sequence"
source                  1..111
                        mol_type = other DNA
                        organism = synthetic construct
SEQUENCE: 93
tactacgcga ggtgggtgaa tggtcgattc accatctcca aaacctcgtc gaccacggtg         60
gatctgaaaa tgaccagtcc gacaaccgag gacacggcca cctatttctg t                111

SEQ ID NO: 94           moltype = AA  length = 37
FEATURE                 Location/Qualifiers
REGION                  1..37
                        note = /note="Description of Artificial Sequence: 6H2-6K2
                        vH framework 3amino acid sequence"
source                  1..37
                        mol_type = protein
                        organism = synthetic construct
SEQUENCE: 94
YYARWVNGRF TISKTSSTTV DLKMTSPTTE DTATYFC                                 37

SEQ ID NO: 95           moltype = DNA  length = 39
FEATURE                 Location/Qualifiers
misc_feature            1..39
                        note = /note="Description of Artificial Sequence: 6H2-6K2
                        vH CDR-H3 cDNAsequence"
source                  1..39
                        mol_type = other DNA
                        organism = synthetic construct
SEQUENCE: 95
gccagagatg gccacaatat aattgaatat tatgatttg                               39

SEQ ID NO: 96           moltype = AA  length = 13
FEATURE                 Location/Qualifiers
REGION                  1..13
                        note = /note="Description of Artificial Sequence: 6H2-6K2
                        vH CDR-H3amino acid sequence"
source                  1..13
                        mol_type = protein
                        organism = synthetic construct
SEQUENCE: 96
ARDGHNIIEY YDL                                                           13

SEQ ID NO: 97           moltype = DNA  length = 33
FEATURE                 Location/Qualifiers
misc_feature            1..33
                        note = /note="Description of Artificial Sequence: 6H2-6K2
                        vH J segmentcDNA sequence"
```

```
source                  1..33
                        mol_type = other DNA
                        organism = synthetic construct
SEQUENCE: 97
tggggccagg gcaccctggt caccgtctcg agc                                  33

SEQ ID NO: 98           moltype = AA   length = 11
FEATURE                 Location/Qualifiers
REGION                  1..11
                        note = /note="Description of Artificial Sequence: 6H2-6K2
                        vH J segmentamino acid sequence"
source                  1..11
                        mol_type = protein
                        organism = synthetic construct
SEQUENCE: 98
WGQGTLVTVS S                                                          11

SEQ ID NO: 99           moltype = DNA   length = 396
FEATURE                 Location/Qualifiers
misc_feature            1..396
                        note = /note="Description of Artificial Sequence: 7H5-7K1
                        vK cDNAsequence"
misc_feature            180
                        note = n is a, c, g, or t
source                  1..396
                        mol_type = other DNA
                        organism = synthetic construct
SEQUENCE: 99
atggacacga gggcccccac tcagctgctg gggctcctgc tgctctggct cccaggtgcc     60
aaatgtgatg ttgtgatgac ccaaactcca gcctccctgt ctgaacctgt gggaggcaca    120
gtcaccatca agtgccaggc cagtgagagc attagtagta gattagcctg gtatcagcan    180
aaaccagggc agcctcccaa gctcctgatc tacaaggcat ccactctggc atctggggtc    240
ccatcgcggt tcaaaggcag tggatatggg acagagttca ctctcaccat cagcgacctg    300
gagtgtgccg atgctgccac ttactactgt caatgtactt atattgctag tagttatgga    360
aataatttcg gcggagggac cgaggtggtg gtcaaa                              396

SEQ ID NO: 100          moltype = AA   length = 132
FEATURE                 Location/Qualifiers
REGION                  1..132
                        note = /note="Description of Artificial Sequence: 7H5-7K1
                        vK amino acidsequence"
SITE                    60
                        note = misc_feature - Xaa can be any naturally occurring
                        amino acid
source                  1..132
                        mol_type = protein
                        organism = synthetic construct
SEQUENCE: 100
MDTRAPTQLL GLLLLWLPGA KCDVVMTQTP ASVSEPVGGT VTIKCQASES ISSRLAWYQX     60
KPGQPPKLLI YKASTLASGV PSRFKGSGYG TEFTLTISDL ECADAATYYC QCTYIASSYG    120
NNFGGGTEVV VK                                                        132

SEQ ID NO: 101          moltype = DNA   length = 75
FEATURE                 Location/Qualifiers
misc_feature            1..75
                        note = /note="Description of Artificial Sequence: 7H5-7K1
                        vK signalpeptide cDNA sequence"
source                  1..75
                        mol_type = other DNA
                        organism = synthetic construct
SEQUENCE: 101
atggacacga gggcccccac tcagctgctg gggctcctgc tgctctggct cccaggtgcc     60
aaatgtgatg ttgtg                                                     75

SEQ ID NO: 102          moltype = AA   length = 25
FEATURE                 Location/Qualifiers
REGION                  1..25
                        note = /note="Description of Artificial Sequence: 7H5-7K1
                        vK signalpeptide amino acid sequence"
source                  1..25
                        mol_type = protein
                        organism = synthetic construct
SEQUENCE: 102
MDTRAPTQLL GLLLLWLPGA KCDVV                                           25

SEQ ID NO: 103          moltype = DNA   length = 69
FEATURE                 Location/Qualifiers
misc_feature            1..69
                        note = /note="Description of Artificial Sequence: 7H5-7K1
```

```
                            vK framework 1cDNA sequence"
source                  1..69
                        mol_type = other DNA
                        organism = synthetic construct
SEQUENCE: 103
atgacccaaa ctccagcctc cgtgtctgaa cctgtgggag gcacagtcac catcaagtgc   60
caggccagt                                                            69

SEQ ID NO: 104          moltype = AA   length = 23
FEATURE                 Location/Qualifiers
REGION                  1..23
                        note = /note="Description of Artificial Sequence: 7H5-7K1
                            vK framework 1amino acid sequence"
source                  1..23
                        mol_type = protein
                        organism = synthetic construct
SEQUENCE: 104
MTQTPASVSE PVGGTVTIKC QAS                                            23

SEQ ID NO: 105          moltype = DNA   length = 18
FEATURE                 Location/Qualifiers
misc_feature            1..18
                        note = /note="Description of Artificial Sequence: 7H5-7K1
                            vK CDR-L1 cDNAsequence"
source                  1..18
                        mol_type = other DNA
                        organism = synthetic construct
SEQUENCE: 105
gagagcatta gtagtaga                                                  18

SEQ ID NO: 106          moltype = AA   length = 6
FEATURE                 Location/Qualifiers
REGION                  1..6
                        note = /note="Description of Artificial Sequence: 7H5-7K1
                            vK CDR-L1amino acid sequence"
source                  1..6
                        mol_type = protein
                        organism = synthetic construct
SEQUENCE: 106
ESISSR                                                                6

SEQ ID NO: 107          moltype = DNA   length = 51
FEATURE                 Location/Qualifiers
misc_feature            1..51
                        note = /note="Description of Artificial Sequence: 7H5-7K1
                            vK framework 2cDNA sequence"
misc_feature            18
                        note = n is a, c, g, or t
source                  1..51
                        mol_type = other DNA
                        organism = synthetic construct
SEQUENCE: 107
ttagcctggt atcagcanaa accagggcag cctcccaagc tcctgatcta c             51

SEQ ID NO: 108          moltype = AA   length = 17
FEATURE                 Location/Qualifiers
REGION                  1..17
                        note = /note="Description of Artificial Sequence: 7H5-7K1
                            vK framework 2amino acid sequence"
SITE                    6
                        note = misc_feature - Xaa can be any naturally occurring
                            amino acid
source                  1..17
                        mol_type = protein
                        organism = synthetic construct
SEQUENCE: 108
LAWYQXKPGQ PPKLLIY                                                   17

SEQ ID NO: 109          moltype =   length =
SEQUENCE: 109
000

SEQ ID NO: 110          moltype =   length =
SEQUENCE: 110
000

SEQ ID NO: 111          moltype = DNA   length = 108
FEATURE                 Location/Qualifiers
misc_feature            1..108
```

```
                        note = /note="Description of Artificial Sequence: 7H5-7K1
                         vK framework 3cDNA sequence"
source                  1..108
                        mol_type = other DNA
                        organism = synthetic construct
SEQUENCE: 111
actctggcat ctggggtccc atcgcggttc aaaggcagtg gatatgggac agagttcact   60
ctcaccatca gcgacctgga gtgtgccgat gctgccactt actactgt              108

SEQ ID NO: 112          moltype = AA   length = 36
FEATURE                 Location/Qualifiers
REGION                  1..36
                        note = /note="Description of Artificial Sequence: 7H5-7K1
                         vK framework 3amino acid sequence"
source                  1..36
                        mol_type = protein
                        organism = synthetic construct
SEQUENCE: 112
TLASGVPSRF KGSGYGTEFT LTISDLECAD AATYYC                             36

SEQ ID NO: 113          moltype = DNA   length = 36
FEATURE                 Location/Qualifiers
misc_feature            1..36
                        note = /note="Description of Artificial Sequence: 7H5-7K1
                         vK CDR-L3 cDNAsequence"
source                  1..36
                        mol_type = other DNA
                        organism = synthetic construct
SEQUENCE: 113
caatgtactt atattgctag tagttatgga aataat                             36

SEQ ID NO: 114          moltype = AA   length = 12
FEATURE                 Location/Qualifiers
REGION                  1..12
                        note = /note="Description of Artificial Sequence: 7H5-7K1
                         vK CDR-L3amino acid sequence"
source                  1..12
                        mol_type = protein
                        organism = synthetic construct
SEQUENCE: 114
QCTYIASSYG NN                                                       12

SEQ ID NO: 115          moltype = DNA   length = 30
FEATURE                 Location/Qualifiers
misc_feature            1..30
                        note = /note="Description of Artificial Sequence: 7H5-7K1
                         vK J segmentcDNA sequence"
source                  1..30
                        mol_type = other DNA
                        organism = synthetic construct
SEQUENCE: 115
ttcggcggag ggaccgaggt ggtggtcaaa                                    30

SEQ ID NO: 116          moltype = AA   length = 10
FEATURE                 Location/Qualifiers
REGION                  1..10
                        note = /note="Description of Artificial Sequence: 7H5-7K1
                         vK J segmentamino acid sequence"
source                  1..10
                        mol_type = protein
                        organism = synthetic construct
SEQUENCE: 116
FGGGTEVVVK                                                          10

SEQ ID NO: 117          moltype = DNA   length = 420
FEATURE                 Location/Qualifiers
misc_feature            1..420
                        note = /note="Description of Artificial Sequence: 7H5-7K1
                         vH cDNAsequence"
misc_feature            146
                        note = n is a, c, g, or t
source                  1..420
                        mol_type = other DNA
                        organism = synthetic construct
SEQUENCE: 117
atggagactg gctgcgctg gcttctcctg gtcgctgtgc tcaaaggtgt ccagtgtcag    60
gagcagctgg tggagtccgg gggagacctg gtcaagcctg ggcatccct gacactcacc   120
tgcacagcct ctggattctc cttcantagc agctaccaca tgtgctgggt ccgccaggct  180
ccagggaagg ggctggagtg gatcgcatac atttatgcta gtaatagcgg tggcacttac  240
```

```
tacgcgagtt gggcgaaagg ccgattcacc atctccaaag cctcgtcgac cacggtgact   300
ctgcaaatga ccagtctgac agccgcggac acgccacct  atttctgtgc gagaagggat   360
actggtggga ccagtgctta tgccttgtgg ggccagggca ccctggtcac cgtctcgagc   420
```

```
SEQ ID NO: 118           moltype = AA   length = 140
FEATURE                  Location/Qualifiers
REGION                   1..140
                         note = /note="Description of Artificial Sequence: 7H5-7K1
                         vH amino acidsequence"
SITE                     49
                         note = misc_feature - Xaa can be any naturally occurring
                         amino acid
source                   1..140
                         mol_type = protein
                         organism = synthetic construct
SEQUENCE: 118
METGLRWLLL VAVLKGVQCQ EQLVESGGDL VKPGASLTLT CTASGFSFXS SYHMCWVRQA   60
PGKGLEWIAY IYAGNSGGTY YASWAKGRFT ISKASSTTVT LQMTSLTAAD TATYFCARRD  120
TGGTSAYALW GQGTLVTVSS                                              140

SEQ ID NO: 119           moltype = DNA   length = 57
FEATURE                  Location/Qualifiers
misc_feature             1..57
                         note = /note="Description of Artificial Sequence: 7H5-7K1
                         vH signalpeptide cDNA sequence"
source                   1..57
                         mol_type = other DNA
                         organism = synthetic construct
SEQUENCE: 119
atggagactg ggctgcgctg gcttctcctg gtcgctgtgc tcaaaggtgt ccagtgt     57

SEQ ID NO: 120           moltype = AA   length = 19
FEATURE                  Location/Qualifiers
REGION                   1..19
                         note = /note="Description of Artificial Sequence: 7H5-7K1
                         vH signalpeptide amino acid sequence"
source                   1..19
                         mol_type = protein
                         organism = synthetic construct
SEQUENCE: 120
METGLRWLLL VAVLKGVQC                                                19

SEQ ID NO: 121           moltype = DNA   length = 75
FEATURE                  Location/Qualifiers
misc_feature             1..75
                         note = /note="Description of Artificial Sequence: 7H5-7K1
                         vH framework 1cDNA sequence"
source                   1..75
                         mol_type = other DNA
                         organism = synthetic construct
SEQUENCE: 121
caggagcagc tggtggagtc cggggggagac ctggtcaagc ctggggcatc cctgacactc  60
acctgcacag cctct                                                   75

SEQ ID NO: 122           moltype = AA   length = 25
FEATURE                  Location/Qualifiers
REGION                   1..25
                         note = /note="Description of Artificial Sequence: 7H5-7K1
                         vH framework 1amino acid sequence"
source                   1..25
                         mol_type = protein
                         organism = synthetic construct
SEQUENCE: 122
QEQLVESGGD LVKPGASLTL TCTAS                                        25

SEQ ID NO: 123           moltype = DNA   length = 27
FEATURE                  Location/Qualifiers
misc_feature             1..27
                         note = /note="Description of Artificial Sequence: 7H5-7K1
                         vH CDR-H1 cDNAsequence"
misc_feature             14
                         note = n is a, c, g, or t
source                   1..27
                         mol_type = other DNA
                         organism = synthetic construct
SEQUENCE: 123
ggattctcct tcantagcag ctaccac                                      27

SEQ ID NO: 124           moltype = AA   length = 9
```

```
FEATURE                 Location/Qualifiers
REGION                  1..9
                        note = /note="Description of Artificial Sequence: 7H5-7K1
                        vH CDR-H1amino acid sequence"
SITE                    5
                        note = misc_feature - Xaa can be any naturally occurring
                        amino acid
source                  1..9
                        mol_type = protein
                        organism = synthetic construct
SEQUENCE: 124
GFSFXSSYH                                                                    9

SEQ ID NO: 125          moltype = DNA  length = 51
FEATURE                 Location/Qualifiers
misc_feature            1..51
                        note = /note="Description of Artificial Sequence: 7H5-7K1
                        vH framework 2cDNA sequence"
source                  1..51
                        mol_type = other DNA
                        organism = synthetic construct
SEQUENCE: 125
atgtgctggg tccgccaggc tccagggaag gggctggagt ggatcgcata c             51

SEQ ID NO: 126          moltype = AA  length = 17
FEATURE                 Location/Qualifiers
REGION                  1..17
                        note = /note="Description of Artificial Sequence: 7H5-7K1
                        vH framework 2amino acid sequence"
source                  1..17
                        mol_type = protein
                        organism = synthetic construct
SEQUENCE: 126
MCWVRQAPGK GLEWIAY                                                          17

SEQ ID NO: 127          moltype = DNA  length = 27
FEATURE                 Location/Qualifiers
misc_feature            1..27
                        note = /note="Description of Artificial Sequence: 7H5-7K1
                        vH CDR-H2 cDNAsequence"
source                  1..27
                        mol_type = other DNA
                        organism = synthetic construct
SEQUENCE: 127
atttatgctg gtaatagcgg tggcact                                               27

SEQ ID NO: 128          moltype = AA  length = 9
FEATURE                 Location/Qualifiers
REGION                  1..9
                        note = /note="Description of Artificial Sequence: 7H5-7K1
                        vH CDR-H2amino acid sequence"
source                  1..9
                        mol_type = protein
                        organism = synthetic construct
SEQUENCE: 128
IYAGNSGGT                                                                    9

SEQ ID NO: 129          moltype = DNA  length = 111
FEATURE                 Location/Qualifiers
misc_feature            1..111
                        note = /note="Description of Artificial Sequence: 7H5-7K1
                        vH framework 3cDNA sequence"
source                  1..111
                        mol_type = other DNA
                        organism = synthetic construct
SEQUENCE: 129
tactacgcga gttgggcgaa aggccgattc accatctcca agcctcgtc gaccacggtg    60
actctgcaaa tgaccagtct gacagccgcg gacacggcca cctatttctg t           111

SEQ ID NO: 130          moltype = AA  length = 37
FEATURE                 Location/Qualifiers
REGION                  1..37
                        note = /note="Description of Artificial Sequence: 7H5-7K1
                        vH framework 3amino acid sequence"
source                  1..37
                        mol_type = protein
                        organism = synthetic construct
SEQUENCE: 130
YYASWAKGRF TISKASSTTV TLQMTSLTAA DTATYFC                                    37
```

-continued

```
SEQ ID NO: 131         moltype = DNA  length = 39
FEATURE                Location/Qualifiers
misc_feature           1..39
                       note = /note="Description of Artificial Sequence: 7H5-7K1
                       vH CDR-H3 cDNAsequence"
source                 1..39
                       mol_type = other DNA
                       organism = synthetic construct
SEQUENCE: 131
gcgagaaggg atactggtgg gaccagtgct tatgccttg                             39

SEQ ID NO: 132         moltype = AA  length = 13
FEATURE                Location/Qualifiers
REGION                 1..13
                       note = /note="Description of Artificial Sequence: 7H5-7K1
                       vH CDR-H3amino acid sequence"
source                 1..13
                       mol_type = protein
                       organism = synthetic construct
SEQUENCE: 132
ARRDTGGTSA YAL                                                        13

SEQ ID NO: 133         moltype = DNA  length = 33
FEATURE                Location/Qualifiers
misc_feature           1..33
                       note = /note="Description of Artificial Sequence: 7H5-7K1
                       vH J segmentcDNA sequence"
source                 1..33
                       mol_type = other DNA
                       organism = synthetic construct
SEQUENCE: 133
tggggccagg gcaccctggt caccgtctcg agc                                  33

SEQ ID NO: 134         moltype = AA  length = 11
FEATURE                Location/Qualifiers
REGION                 1..11
                       note = /note="Description of Artificial Sequence: 7H5-7K1
                       vH J segmentamino acid sequence"
source                 1..11
                       mol_type = protein
                       organism = synthetic construct
SEQUENCE: 134
WGQGTLVTVS S                                                          11

SEQ ID NO: 135         moltype = DNA  length = 2115
FEATURE                Location/Qualifiers
source                 1..2115
                       mol_type = other DNA
                       organism = Homo sapiens
CDS                    69..935
SEQUENCE: 135
agtttccctt ccgctcacct ccgcctgagc agtggagaag gcggcactct ggtgggctg      60
ctccaggcat gcagatccca caggcgccct ggcagtcgt ctgggcggtg ctacaactgg     120
gctgcgggcc aggatggttc ttagactccc cagacagcc ctggaacccc ccaccttct      180
ccccagccct gctcgtggtg accgaagggg acaacgccac cttcacctgc agcttctcca    240
acacatcgga gagcttggtg ctaaaactgg accgcatgag cccagcaac cagacggaca     300
agctggccgc cttccccgag gaccgcagcc agcccggcca ggactgccgc ttccgtgtca    360
cacaactgcc caacgggcgt gacttccaca tgagcgtggt ggggcccgg cgcaatgaca     420
gcggcaccta cctctgtggg gccatctccc tggcccccaa ggcgcagatc aaagagagcc    480
tgcgggcaga gctcagggtg acagagagaa gggcagaagt gcccacagcc caccccagcc    540
cctcacccag gccagccggc cagttccaaa ccctggtggt tggtgtcgtg gcggcctgc     600
tgggcagcct ggtgctgcta gtctgggtcc tggccgtcat ctgctcccgg gccgcacgag    660
ggacaatagg agccaggcgc accggccagc ccctgaaggg ggacccctca gccgtgcctg    720
tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc ccccgcccgc agggggctcag ctgacggccc tcggagtgcc cagccactga    900
ggcctgagga tggacactgc tcttggcccc tctgaccggc ttccttggcc accagtgttc     960
tgcagaccct ccaccatgag cccgggtcag cgcatttcct caggagaagc aggcagggtg    1020
caggccattg caggccgtcc aggggctgag ctgcctgggg gcgaccgggg ctccagcctg    1080
cacctgcacc aggcacagcc ccaccacagg actcatgtct caatgccac agtgagccca     1140
ggcagcaggt gtcaccgtcc cctacaggga gggccagatg cagtcactgc ttcaggtcct    1200
gccagcacag agctgcctgc gtccagctcc ctgaatctct gctgctgctg ctgctgctgc    1260
tgctgctgcc tgcctgccgg ggctgaaggc gccgtggcctg tgctgacgc tgcgagagcct    1320
cctgcctgaa cttgggggct ggttggagat ggccttggag cagccaaggt gccctggca     1380
gtggcatccc gaaacgccct ggacgcaggg cccaagactg gcacaggag tgggaggtac     1440
atggggctgg ggactcccca ggagttatct gctccctgca ggcctagaga gtttcaggg    1500
aaggtcgaaa gagctcctgg ctgtggtggg caggcagga aaccccctcca cctttacaca    1560
tgcccaggca gcacctcagg ccctttgtgg ggcaggaag ctgaggcagt aagcgggcag     1620
```

```
gcagagctgg aggcctttca ggcccagcca gcactctggc ctcctgccgc cgcattccac   1680
cccagcccct cacaccactc gggagaggga catcctacgg tcccaaggtc aggagggcag   1740
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggca tggtgggaa ggtacaggcg   1920
ttcccccggg gcctagtacc ccgccgtgg cctatccact cctcacatcc acacactgca   1980
ccccactcc tggggcaggg ccaccagcat ccaggcggcc agcaggcacc tgagtggctg   2040
ggacaaggga tcccccttcc ctgtggttct attatattat aattataatt aaatatgaga   2100
gcatgctaag gaaaa                                                   2115

SEQ ID NO: 136          moltype = AA   length = 288
FEATURE                 Location/Qualifiers
source                  1..288
                        mol_type = protein
                        organism = Homo sapiens
SEQUENCE: 136
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL               288

SEQ ID NO: 137          moltype = AA   length = 288
FEATURE                 Location/Qualifiers
source                  1..288
                        mol_type = protein
                        organism = Homo sapiens
SEQUENCE: 137
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL               288

SEQ ID NO: 138          moltype = DNA   length = 1972
FEATURE                 Location/Qualifiers
source                  1..1972
                        mol_type = other DNA
                        organism = Mus musculus
CDS                     64..930
SEQUENCE: 138
tgagcagcgg ggaggaggaa gaggagactg ctactgaagg cgacactgcc aggggctctg     60
ggcatgtggg tccggcaggt accctggtca ttcacttggg ctgtgctgca gttgagctgg    120
caatcagggt ggcttctaga ggtccccaat gggccctgga ggtccctcac cttctaccca    180
gcctggctca cagtgtcaga gggagcaaat gccaccttca cctgcagctt gtccaactgg    240
tcggaggatc ttatgctgaa ctggaaccgc ctgagtccca gcaaccagac tgaaaaacag    300
gccgccttct gtaatggttt gagccaaacc gtccaggatg cgccttcca gatcatacag    360
ctgcccaaca gcatgacttt ccacatgaac atccttgaca cacggcgcaa tgacagtggc    420
atctacctct gtggggccat ctccctgcac ccaaggcaa aaatcgagga gagccctgga    480
gcagagctcg tggtaacaga gagaatcctg gagacctcaa caagatatcc cagccctcg    540
cccaaaccag aaggccggtt tcaaggcatg gtcattggta tcatgagtgc cctagtaggt    600
atccctgtat tgctgctgct ggcctggggc ctagctgtct tctgctcaac aagtatgtca    660
gaggccagag gagctggaag caaggacgac actctgaagg aggagccttc agcagcacct    720
gtccctagtg tggcctatga ggagctggac ttccagggac gagagaagac accagagctc    780
cctaccgcct gtgtgcacac agaatatgcc accattgtct tctgaagg gctgggtgcc    840
tcggccatgg gacgtagggg ctcagctgat ggcctgcagg gtcctcggcc tccaagacat    900
gaggatggac attgttcttg gcctctttga ccagattctt cagccattag catgctgcag    960
accctccaca gagagcaccg gtccgtccct cagtcaagag gagcatgcag gctacagttc   1020
agccaaggct cccagggtct gagctagctg gagtgacagc ccagcgcctg caccaattcc   1080
agcacatgca ctgttgagtg agagctcact tcaggtttac cacaagctgg gagcagcagg   1140
cttcccggtt tcctattgtc acaaggtgca gagctgggc ctaagccta gtctcctgaa    1200
tcctactgtt gggcacttct agggacttga gacactatag ccaatggcct ctgtgggttc   1260
tgtgcctgga aatggagaga tctgagtaca gcctgctttg aatggccctg tgaggcaacc   1320
ccaaagtcaa ggggtccagg tatactatgg gcccagcaac taaagccacc cttgggagat   1380
gatactcagg tgggaaattc gtagactggg ggactgaacc aatcccaaga tctgaaaaag   1440
ttttgatgaa gacttgaaaa gctcctagct tcggggtct gggaagcatg agcacttacc   1500
aggcaaaagc tccgtgagcg tatctgctgt ccttctgcat gcccaggtac ctcagttttt    1560
ttcaacagca aggaaactag gcaataaaag ggaaccagca gagctagagc cacccacaca   1620
tccaggggc acttgactct ccctactcct cctaggaacc aaaaggacaa agtccatgtt   1680
gacagcaggg aaggaaaggg ggatataacc ttgacgcaaa ccaacactgg ggtgttagaa   1740
tctcctcatt cactctgtcc tggagttggg ttctggctct ccttcacacc taggactctg   1800
aaaatgagca agcacttcaga cagtcagggt agcaagagtc tagctgtctg gtgggcaccc   1860
aaaatgacca gggcttaagt ccccttttcctt tggttttaagc ccgttataat taaatggtac    1920
caaaagcttt aaaaaaaaaa aaaaaaaaaa aaaaaaaaaa aaaaaaaaa aa             1972

SEQ ID NO: 139          moltype = AA   length = 288
FEATURE                 Location/Qualifiers
source                  1..288
                        mol_type = protein
```

```
                        organism = Mus musculus
SEQUENCE: 139
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERILE TSTRYPSPSP KPEGRFQGMV IGIMSALVGI   180
PVLLLLAWAL AVFCSTSMSE ARGAGSKDDT LKEEPSAAPV PSVAYEELDF QGREKTPELP   240
TACVHTEYAT IVFTEGLGAS AMGRRGSADG LQGPRPPRHE DGHCSWPL               288

SEQ ID NO: 140          moltype = AA  length = 288
FEATURE                 Location/Qualifiers
source                  1..288
                        mol_type = protein
                        organism = Mus musculus
SEQUENCE: 140
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERILE TSTRYPSPSP KPEGRFQGMV IGIMSALVGI   180
PVLLLLAWAL AVFCSTSMSE ARGAGSKDDT LKEEPSAAPV PSVAYEELDF QGREKTPELP   240
TACVHTEYAT IVFTEGLGAS AMGRRGSADG LQGPRPPRHE DGHCSWPL               288

SEQ ID NO: 141          moltype = AA  length = 17
FEATURE                 Location/Qualifiers
REGION                  1..17
                        note = /note="Description of Artificial Sequence:
                        mPD-L1kappa/mPD-L1-hIgG1 fusion protein linker sequence"
source                  1..17
                        mol_type = protein
                        organism = synthetic construct
SEQUENCE: 141
GGSGGTGGSG GTGGSGG                                                  17

SEQ ID NO: 142          moltype = AA  length = 23
FEATURE                 Location/Qualifiers
REGION                  1..23
                        note = /note="Description of Artificial Sequence: PD-1
                        pITSM peptidesequence"
MOD_RES                 16
                        note = PHOSPHORYLATION
source                  1..23
                        mol_type = protein
                        organism = synthetic construct
SEQUENCE: 142
KTPEPPVPCV PEQTEYATIV FPS                                           23

SEQ ID NO: 143          moltype = AA  length = 24
FEATURE                 Location/Qualifiers
REGION                  1..24
                        note = /note="Description of Artificial Sequence: PD-1
                        pITIM peptidesequence"
MOD_RES                 14
                        note = PHOSPHORYLATION
source                  1..24
                        mol_type = protein
                        organism = synthetic construct
SEQUENCE: 143
KEDPSAVPVF SVDPYGELDF QWRE                                          24

SEQ ID NO: 144          moltype = AA  length = 12
FEATURE                 Location/Qualifiers
source                  1..12
                        mol_type = protein
                        organism = Homo sapiens
SEQUENCE: 144
VPEQTEYATI VF                                                       12

SEQ ID NO: 145          moltype = AA  length = 12
FEATURE                 Location/Qualifiers
source                  1..12
                        mol_type = protein
                        organism = Mus musculus
SEQUENCE: 145
ACVHTEYATI VF                                                       12

SEQ ID NO: 146          moltype = AA  length = 12
FEATURE                 Location/Qualifiers
REGION                  1..12
                        note = /note="Description of Artificial Sequence: Synthetic
                        PD-1 ITSMpeptide equence"
MOD_RES                 7
```

```
                        note = PHOSPHORYLATION
source                  1..12
                        mol_type = protein
                        organism = synthetic construct
SEQUENCE: 146
VPEQTEYATI VF                                                              12

SEQ ID NO: 147          moltype = AA  length = 12
FEATURE                 Location/Qualifiers
REGION                  1..12
                        note = /note="Description of Artificial Sequence: Synthetic
                         PD-1 ITSMpeptide equence"
MOD_RES                 7
                        note = PHOSPHORYLATION
source                  1..12
                        mol_type = protein
                        organism = synthetic construct
SEQUENCE: 147
ACVHTEYATI VF                                                              12
```